(12) United States Patent
Srivastava et al.

(10) Patent No.: US 7,537,896 B2
(45) Date of Patent: May 26, 2009

(54) ANDROGEN-REGULATED PMEPA1 GENE AND POLYPEPTIDES

(75) Inventors: Shiv Srivastava, Potomac, MD (US); Judd W. Moul, Bethesda, MD (US); Linda L. Xu, Rockville, MD (US)

(73) Assignee: Henry M. Jackson Foundation for the Advancement of Military Medicine, Rockville, MD (US)

(*) Notice: Subject to any disclaimer, the term of this patent is extended or adjusted under 35 U.S.C. 154(b) by 162 days.

(21) Appl. No.: 11/452,925

(22) Filed: Jun. 15, 2006

(65) Prior Publication Data

US 2006/0269546 A1 Nov. 30, 2006

Related U.S. Application Data

(60) Continuation of application No. 10/434,479, filed on May 9, 2003, now abandoned, which is a continuation-in-part of application No. 10/390,045, filed on Mar. 18, 2003, now abandoned, which is a division of application No. 09/769,482, filed on Jan. 26, 2001, now Pat. No. 6,556,130.

(60) Provisional application No. 60/378,949, filed on May 10, 2002, provisional application No. 60/179,045, filed on Jan. 31, 2000, provisional application No. 60/178,772, filed on Jan. 28, 2000.

(51) Int. Cl.
*C12Q 1/68* (2006.01)

(52) U.S. Cl. .......................................... 435/6; 435/7.23

(58) Field of Classification Search ....................... None
See application file for complete search history.

(56) References Cited

U.S. PATENT DOCUMENTS

| | | | |
|---|---|---|---|
| 5,676,945 | A | 10/1997 | Reddy et al. |
| 5,677,144 | A | 10/1997 | Ullrich et al. |
| 5,695,937 | A | 12/1997 | Kinzler et al. |
| 5,744,305 | A | 4/1998 | Fodor et al. |
| 5,837,832 | A | 11/1998 | Chee et al. |
| 5,861,242 | A | 1/1999 | Chee et al. |
| 5,866,330 | A | 2/1999 | Kinzler et al. |
| 6,268,377 | B1 | 7/2001 | Waldstreicher et al. |
| 6,303,324 | B1 | 10/2001 | Fruehauf |
| 6,312,922 | B1 | 11/2001 | Edwards et al. |
| 6,566,130 | B1 | 5/2003 | Srivastava et al. |
| 6,897,018 | B1 * | 5/2005 | Yuan et al. ............ 435/6 |
| 7,071,303 | B2 | 7/2006 | Lin |
| 2003/0027998 | A1 | 2/2003 | Holtzman et al. |
| 2003/0108963 | A1 | 6/2003 | Schlegel et al. |
| 2003/0148314 | A1 | 8/2003 | Berger et al. |
| 2003/0148410 | A1 | 8/2003 | Berger et al. |
| 2005/0191673 | A1 | 9/2005 | Schlegel et al. |
| 2005/0266493 | A1 | 12/2005 | Berger et al. |

FOREIGN PATENT DOCUMENTS

| | | |
|---|---|---|
| WO | WO 00/34477 | 6/2000 |
| WO | WO 00/50454 | 8/2000 |
| WO | WO 00/52022 | 9/2000 |
| WO | WO 01/53312 | 7/2001 |
| WO | WO 02/16416 | 2/2002 |
| WO | WO 02/30268 | 4/2002 |
| WO | WO 02/083876 | 10/2002 |
| WO | WO 03/024392 | 3/2003 |
| WO | WO 03/042661 | 5/2003 |
| WO | WO 03/048202 | 6/2003 |
| WO | WO 03/072827 | 9/2003 |

OTHER PUBLICATIONS

Hittelman et al, Curr Opin Urology, 2004, 14:163-170.*
Xu, Linda L., et al., "PMEPA1, an Androgen-regulated NEDD4-binding Protein, Exhibits Cell Growth Inhibitory Function and Decreased Expression during Prostate Cancer Progression," Cancer Research, 63:4299-4304, 2003.
Rae, Fiona K., et al., "Characterization of a Novel Gene, *STAG1/PMEPA1*, Upregulated in Renal Cell Carcinoma and Other Solid Tumors," Molecular Carcinogenesis, 32:44-53, 2001.
Itoh, Susumu, et al., "Elucidation of Smad Requirement in Transforming Growth Factor-β Type I Receptor-induced Responses," The Journal of Biological Chemistry, 278(6):3751-3761, 2003.
Brunschwig, Elaine B., et al., "*PMEPA1*, a Transforming Growth Factor-β-induced Marker of Terminal Colonocyte Differentiation Whose Expression Is Maintained in Primary and Metastatic Colon Cancer," Cancer Research, 63:1568-1575, 2003.
International Search Report in PCT/US03/13401, mailed Jun. 29, 2004.

(Continued)

*Primary Examiner*—Misook Yu
*Assistant Examiner*—Mark Halvorson
(74) *Attorney, Agent, or Firm*—Latimer, Mayberry & Matthews IP Law

(57) ABSTRACT

This invention relates to the androgen-regulated gene, PMEPA1, and proteins encoded by this gene, including variants and analogs thereof. Also provided are other androgen-regulated nucleic acids, a polynucleotide array containing these androgen-regulated nucleic acids, and methods of using the polynucleotide array in the diagnosis and prognosis of prostate cancer.

11 Claims, 12 Drawing Sheets

OTHER PUBLICATIONS

Hillier et al., GenBank Accession No. AA088767, Oct. 24, 1996.
Supplementary Partial European Search Report from related application EP 03 72 4331.
Velculescu, V.E., et al., "Serial Analysis of Gene Expression," Science, 270:484-487, 1995.
Xu, L., et al., "Quantitative Expression Profile of Androgen-Regulated Genes in Prostate Cancer Cells and Identification of Prostate-Specific Genes," Int. J. Cancer, 92:322-328, 2001.
Xu et al., "A Novel Androgen-Related Gene, PMEPA1 Located on Chromosome 20q13 Exhibits High Level Expression in Prostate," Genomics, 66:257-263, 2000.
Banerjee et al., Identification of Downstream Targets of the Putative Tumor Suppressor Gene on 8p by Differential Gene Expression Analysis, Proc. American Assoc. for Cancer Research, 42:2299, Mar. 2001.
Segawa, T., et al., "Androgen-induced Expression of Endoplasmic Reticulum (ER) Stress Response Genes in Prostate Cancer Cells," Oncogene, 21:8749-8758, 2002.
Supplementary Partial European Search Report from related application EP 03 72 4331, mail date Jan. 12, 2005.

* cited by examiner

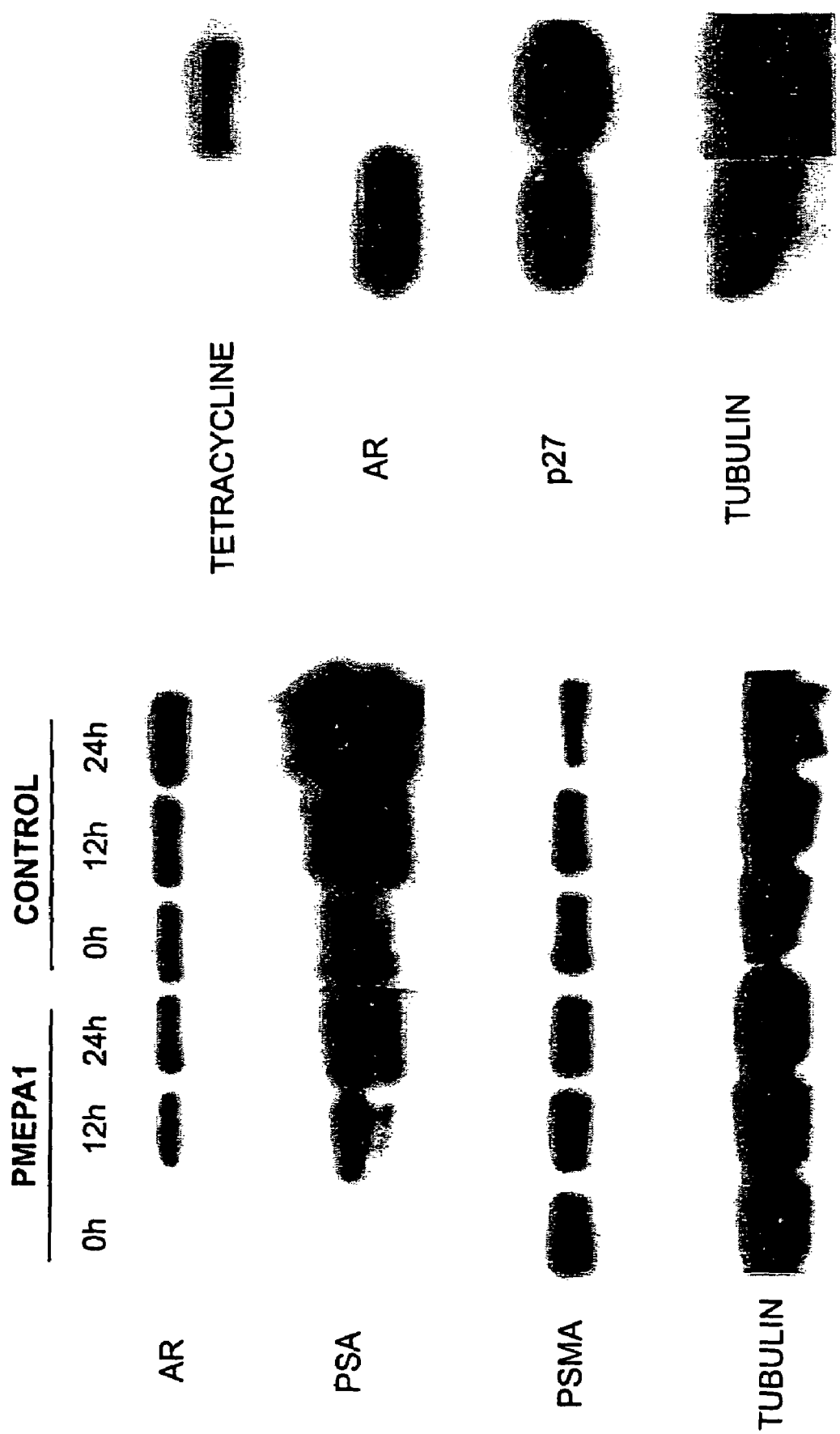

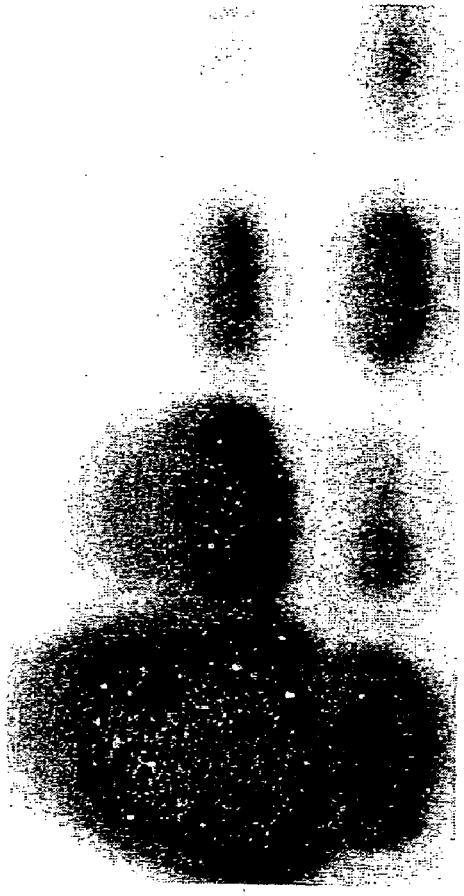
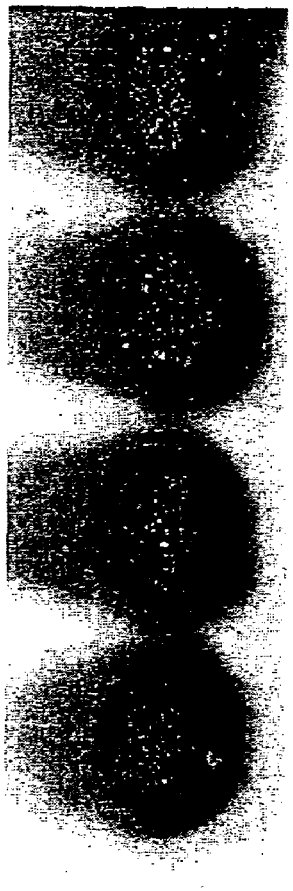
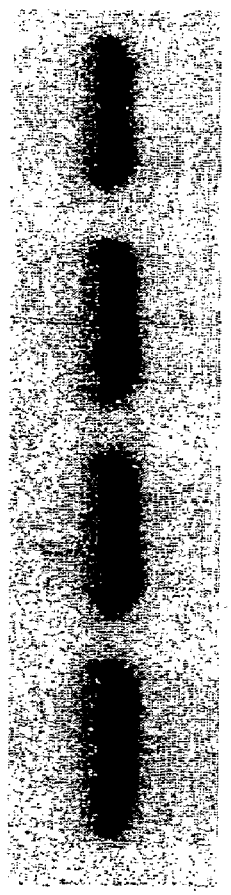
FIG. 7

SEQUENCE LISTING

<160> NUMBER OF SEQ ID NOS: 81

<210> SEQ ID NO 1
<211> LENGTH: 1140
<212> TYPE: DNA
<213> ORGANISM: Homo sapiens
<220> FEATURE:
<221> NAME/KEY: CDS
<222> LOCATION: (95)..(850)

<400> SEQUENCE: 1

```
tccttgggtt cgggtgaaag cgcctggggg ttcgtggcca tgatccccga gctgctggag       60
aactgaaggc ggacagtctc ctgcgaaaca ggca atg gcg gag ctg gag ttt gtt      115
                                     Met Ala Glu Leu Glu Phe Val
                                       1               5 cag atc atc atc atc gtg gtg gtg atg atg gtg atg gtg gtg gtg atc        163
Gln Ile Ile Ile Ile Val Val Val Met Met Val Met Val Val Val Ile
         10                  15                  20 acg tgc ctg ctg agc cac tac aag ctg tct gca cgg tcc ttc atc agc        211
Thr Cys Leu Leu Ser His Tyr Lys Leu Ser Ala Arg Ser Phe Ile Ser
     25                  30                  35 cgg cac agc cag ggg cgg agg aga gaa gat gcc ctg tcc tca gaa gga        259
Arg His Ser Gln Gly Arg Arg Arg Glu Asp Ala Leu Ser Ser Glu Gly
 40                  45                  50                  55 tgc ctg tgg ccc tcg gag agc aca gtg tca ggc aac gga atc cca gag        307
Cys Leu Trp Pro Ser Glu Ser Thr Val Ser Gly Asn Gly Ile Pro Glu
                 60                  65                  70 ccg cag gtc tac gcc ccg cct cgg ccc acc gac cgc ctg gcc gtg ccg        355
Pro Gln Val Tyr Ala Pro Pro Arg Pro Thr Asp Arg Leu Ala Val Pro
             75                  80                  85 ccc ttc gcc cag cgg gag cgc ttc cac cgc ttc cag ccc acc tat ccg        403
Pro Phe Ala Gln Arg Glu Arg Phe His Arg Phe Gln Pro Thr Tyr Pro
         90                  95                 100 tac ctg cag cac gag atc gac ctg cca ccc acc atc tcg ctg tca gac        451
Tyr Leu Gln His Glu Ile Asp Leu Pro Pro Thr Ile Ser Leu Ser Asp
     105                 110                 115 ggg gag gag ccc cca ccc tac cag ggc ccc tgc acc ctc cag ctt cgg        499
Gly Glu Glu Pro Pro Pro Tyr Gln Gly Pro Cys Thr Leu Gln Leu Arg
120                 125                 130                 135 gac ccc gag cag cag ctg gaa ctg aac cgg gag tcg gtg cgc gca ccc        547
Asp Pro Glu Gln Gln Leu Glu Leu Asn Arg Glu Ser Val Arg Ala Pro
                 140                 145                 150 cca aac aga acc atc ttc gac agt gac ctg atg gat agt gcc agg ctg        595
Pro Asn Arg Thr Ile Phe Asp Ser Asp Leu Met Asp Ser Ala Arg Leu
             155                 160                 165 ggc ggc ccc tgc ccc ccc agc agt aac tcg ggc atc agc gcc acg tgc        643
Gly Gly Pro Cys Pro Pro Ser Ser Asn Ser Gly Ile Ser Ala Thr Cys
         170                 175                 180 tac ggc agc ggc ggg cgc atg gag ggg ccg ccg ccc acc tac agc gag        691
Tyr Gly Ser Gly Gly Arg Met Glu Gly Pro Pro Pro Thr Tyr Ser Glu
     185                 190                 195 gtc atc ggc cac tac ccg ggg tcc tcc ttc cag cac cag cag agc agt        739
Val Ile Gly His Tyr Pro Gly Ser Ser Phe Gln His Gln Gln Ser Ser
200                 205                 210                 215 ggg ccg ccc tcc ttg ctg gag ggg acc cgg ctc cac cac aca cac atc        787
Gly Pro Pro Ser Leu Leu Glu Gly Thr Arg Leu His His Thr His Ile
                 220                 225                 230 gcg ccc cta gag agc gca gcc atc tgg agc aaa gag aag gat aaa cag        835
Ala Pro Leu Glu Ser Ala Ala Ile Trp Ser Lys Glu Lys Asp Lys Gln
```

```
                235                 240                 245
aaa gga cac cct ctc tagggtcccc agggggggccg ggctggggct gcgtaggtga       890
Lys Gly His Pro Leu
        250 aaaggcagaa cactccgcgc ttcttagaag aggagtgaga ggaaggcggg gggcgcagca      950 acgcatcgtg tggccctccc ctcccacctc cctgtgtata aatatttaca tgtgatgtct     1010 ggtctgaatg cacaagctaa gagagcttgc aaaaaaaaaa agaaaaaaga aaaaaaaaa      1070 ccacgtttct tgttgagct gtgtcttgaa ggcaaaagaa aaaaaatttc tacagtaaaa      1130 aaaaaaaaaa                                                           1140

<210> SEQ ID NO 2
<211> LENGTH: 759
<212> TYPE: DNA
<213> ORGANISM: Homo sapiens

<400> SEQUENCE: 2
atggcggagc tggagtttgt tcagatcatc atcatcgtgg tggtgatgat ggtgatggtg       60
gtggtgatca cgtgcctgct gagccactac aagctgtctg cacggtcctt catcagccgg      120
cacagccagg ggcggaggag agaagatgcc ctgtcctcag aaggatgcct gtggccctcg      180
gagagcacag tgtcaggcaa cggaatccca gagccgcagg tctacgcccc gcctcggccc      240
accgaccgcc tggccgtgcc gcccttcgcc cagcgggagc gcttccaccg cttccagccc      300
acctatccgt acctgcagca cgagatcgac ctgccacccca ccatctcgct gtcagacggg      360
gaggagcccc cacccctacca gggcccctgc accctccagc ttcgggaccc cgagcagcag      420
ctggaactga accgggagtc ggtgcgcgca ccccccaaaca gaaccatctt cgacagtgac      480
ctgatggata gtgccaggct gggcggcccc tgccccccca gcagtaactc gggcatcagc      540
gccacgtgct acggcagcgg cgggcgcatg gaggggccgc cgcccaccta cagcgaggtc      600
atcggccact acccggggtc ctccttccag caccagcaga gcagtgggcc gccctccttg      660
ctggagggga cccggctcca ccacacacac atcgcgcccc tagagagcgc agccatctgg      720
agcaaagaga aggataaaca gaaaggacac cctctctag                             759

<210> SEQ ID NO 3
<211> LENGTH: 252
<212> TYPE: PRT
<213> ORGANISM: Homo sapiens

<400> SEQUENCE: 3

Met Ala Glu Leu Glu Phe Val Gln Ile Ile Ile Ile Val Val Val Met
 1               5                  10                  15

Met Val Met Val Val Val Ile Thr Cys Leu Leu Ser His Tyr Lys Leu
                20                  25                  30

Ser Ala Arg Ser Phe Ile Ser Arg His Ser Gln Gly Arg Arg Arg Glu
        35                  40                  45

Asp Ala Leu Ser Ser Glu Gly Cys Leu Trp Pro Ser Glu Ser Thr Val
    50                  55                  60

Ser Gly Asn Gly Ile Pro Glu Pro Gln Val Tyr Ala Pro Pro Arg Pro
65                  70                  75                  80

Thr Asp Arg Leu Ala Val Pro Pro Phe Ala Gln Arg Glu Arg Phe His
                85                  90                  95

Arg Phe Gln Pro Thr Tyr Pro Tyr Leu Gln His Glu Ile Asp Leu Pro
                100                 105                 110
```

```
Pro Thr Ile Ser Leu Ser Asp Gly Glu Glu Pro Pro Tyr Gln Gly
        115                 120                 125

Pro Cys Thr Leu Gln Leu Arg Asp Pro Glu Gln Gln Leu Glu Leu Asn
    130                 135                 140

Arg Glu Ser Val Arg Ala Pro Pro Asn Arg Thr Ile Phe Asp Ser Asp
145                 150                 155                 160

Leu Met Asp Ser Ala Arg Leu Gly Gly Pro Cys Pro Pro Ser Ser Asn
                165                 170                 175

Ser Gly Ile Ser Ala Thr Cys Tyr Ser Gly Gly Arg Met Glu Gly
            180                 185                 190

Pro Pro Thr Tyr Ser Glu Val Ile Gly His Tyr Pro Gly Ser Ser
        195                 200                 205

Phe Gln His Gln Gln Ser Ser Gly Pro Ser Leu Leu Glu Gly Thr
    210                 215                 220

Arg Leu His His Thr His Ile Ala Pro Leu Glu Ser Ala Ala Ile Trp
225                 230                 235                 240

Ser Lys Glu Lys Asp Lys Gln Lys Gly His Pro Leu
                245                 250
```

```
<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: FLAG
      peptide

<400> SEQUENCE: 4

Asp Tyr Lys Asp Asp Asp Asp Lys
  1               5

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
ggcagaacac tccgcgcttc ttag                                          24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 6
caagctctct tagcttgtgc attc                                          24

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 7
cttgggttcg ggtgaaagcg cc                                            22

<210> SEQ ID NO 8
```

```
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
ggtgggtggc aggtcgatct cg                                          22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
ccttcgccca gcgggagcgc                                             20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
caagctctct tagcttgtgc attc                                        24

<210> SEQ ID NO 11
<211> LENGTH: 249
<212> TYPE: PRT
<213> ORGANISM: Homo sapiens

<400> SEQUENCE: 11
```

Ala Glu Leu Glu Phe Val Gln Ile Ile Ile Val Val Val Met Met
 1               5                  10                  15

Val Met Val Val Val Ile Thr Cys Leu Leu Ser His Tyr Lys Leu Ser
                20                  25                  30

Ala Arg Ser Phe Ile Ser Arg His Ser Gln Gly Arg Arg Arg Glu Asp
            35                  40                  45

Ala Leu Ser Ser Glu Gly Cys Leu Trp Pro Ser Glu Ser Thr Val Ser
        50                  55                  60

Gly Asn Gly Ile Pro Glu Pro Gln Val Tyr Ala Pro Pro Arg Pro Thr
    65                  70                  75                  80

Asp Arg Leu Ala Val Pro Pro Phe Ala Gln Arg Glu Arg Phe His Arg
                85                  90                  95

Phe Gln Pro Thr Tyr Pro Tyr Leu Gln His Glu Ile Asp Leu Pro Pro
            100                 105                 110

Thr Ile Ser Leu Ser Asp Gly Glu Glu Pro Pro Tyr Gln Gly Pro
        115                 120                 125

Cys Thr Leu Gln Leu Arg Asp Pro Glu Gln Gln Leu Glu Leu Asn Arg
    130                 135                 140

Glu Ser Val Arg Ala Pro Asn Arg Thr Ile Phe Asp Ser Asp Leu
145                 150                 155                 160

Met Asp Ser Ala Arg Leu Gly Gly Pro Cys Pro Pro Ser Ser Asn Ser
                165                 170                 175

Gly Ile Ser Ala Thr Cys Tyr Gly Ser Gly Arg Met Glu Gly Pro
            180                 185                 190

Pro Pro Thr Tyr Ser Glu Val Ile Gly His Tyr Pro Gly Ser Ser Phe

-continued

```
            195                 200                 205
Gln His Gln Gln Ser Ser Gly Pro Pro Ser Leu Leu Glu Gly Thr Arg
    210                 215                 220

Leu His His Thr His Ile Ala Pro Leu Glu Ser Ala Ala Ile Trp Ser
225                 230                 235                 240

Lys Glu Lys Asp Lys Gln Lys Gly His
                245

<210> SEQ ID NO 12
<211> LENGTH: 244
<212> TYPE: PRT
<213> ORGANISM: Homo sapiens

<400> SEQUENCE: 12

Ala Glu Leu Glu Phe Ala Gln Ile Ile Ile Val Val Val Val Thr
  1               5                  10                  15

Val Met Val Val Ile Val Cys Leu Leu Asn His Tyr Lys Val Ser
                 20                  25                  30

Thr Arg Ser Phe Ile Asn Arg Pro Asn Gln Ser Arg Arg Glu Asp
             35                  40                  45

Gly Leu Pro Gln Glu Gly Cys Leu Trp Pro Ser Asp Ser Ala Ala Pro
     50                  55                  60

Arg Leu Gly Ala Ser Glu Ile Met His Ala Pro Arg Ser Arg Asp Arg
 65                  70                  75                  80

Phe Thr Ala Pro Ser Phe Ile Gln Arg Asp Arg Phe Ser Arg Phe Gln
                 85                  90                  95

Pro Thr Tyr Pro Tyr Val Gln His Glu Ile Asp Leu Pro Pro Thr Ile
                100                 105                 110

Ser Leu Ser Asp Gly Glu Glu Pro Pro Tyr Gln Gly Pro Cys Thr
            115                 120                 125

Leu Gln Leu Arg Asp Pro Glu Gln Gln Met Glu Leu Asn Arg Glu Ser
    130                 135                 140

Val Arg Ala Pro Pro Asn Arg Thr Ile Phe Asp Ser Asp Leu Ile Asp
145                 150                 155                 160

Ile Ala Met Tyr Ser Gly Gly Pro Cys Pro Ser Ser Asn Ser Gly
                165                 170                 175

Ile Ser Ala Ser Thr Cys Ser Ser Asn Gly Arg Met Glu Gly Pro Pro
            180                 185                 190

Pro Thr Tyr Ser Glu Val Met Gly His His Pro Gly Ala Ser Phe Leu
                195                 200                 205

His His Gln Arg Ser Asn Ala His Arg Gly Ser Arg Leu Gln Phe Gln
    210                 215                 220

Gln Asn Asn Ala Glu Ser Thr Ile Val Pro Ile Lys Gly Lys Asp Arg
225                 230                 235                 240

Lys Pro Gly Asn

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gccagcccag                                                            10
```

```
<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtgcagggag                                                              10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gacaaacatt                                                              10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atgactcaag                                                              10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gaaaagaagg                                                              10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cctgtacccc                                                              10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cctgaactgg                                                              10
```

```
<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgacagccca                                                          10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tacaaaacca                                                          10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aattctccta                                                          10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgcatatcat                                                          10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cttgacacac                                                          10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tgtctaacta                                                          10

<210> SEQ ID NO 26
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtggacccca                                                          10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ataaagtaac                                                          10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tacattttca                                                          10

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tcagaacagt                                                          10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
caacttcaac                                                          10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gataggtcgg                                                          10

<210> SEQ ID NO 32
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctaaaaggag                                                              10

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gtggtgcgtg                                                              10

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tccccgtggc                                                              10

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
attgatcttg                                                              10

<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
agctggtttc                                                              10

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cctcccccgt                                                              10

<210> SEQ ID NO 38
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 38
atgtactctg                                                          10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gatgaaatac                                                          10

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtgcatcccg                                                          10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gaaattaggg                                                          10

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tttctagggg                                                          10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cccagggaga                                                          10

<210> SEQ ID NO 44
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 44
gtggcgcaca                                                                  10

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ttgcttttgt                                                                  10

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
atgtcctttc                                                                  10

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tgtttatcct                                                                  10

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gctttgtatc                                                                  10

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gttccagtga                                                                  10

<210> SEQ ID NO 50
<211> LENGTH: 10
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 50
tagcagaggc                                                                10

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
acaaattatg                                                                10

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cagtttgtac                                                                10

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gattacttgc                                                                10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggccagccct                                                                10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
caattgtaaa                                                                10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 56
aaagccaaga                                                                10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
caactaattc                                                                10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aagagctaat                                                                10

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cttttcaaga                                                                10

<210> SEQ ID NO 60
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gtgtgtaaaa                                                                10

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
acaaaatgta                                                                10

<210> SEQ ID NO 62
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 62
aaggtagcag                                                          10

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ggcggggcca                                                          10

<210> SEQ ID NO 64
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ggccagtaac                                                          10

<210> SEQ ID NO 65
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
aacttaagag                                                          10

<210> SEQ ID NO 66
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
agggatggcc                                                          10

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cttaaggatt                                                          10

<210> SEQ ID NO 68
<211> LENGTH: 243
<212> TYPE: PRT
<213> ORGANISM: Mus sp.

<400> SEQUENCE: 68

Ile Thr Glu Leu Glu Phe Val Gln Ile Val Val Ile Val Val Val Met
```

```
  1               5               10              15
Met Val Met Val Val Met Ile Thr Cys Leu Leu Ser His Tyr Lys Leu
                20              25              30

Ser Ala Arg Ser Phe Ile Ser Arg His Ser Gln Ala Arg Arg Arg Asp
        35              40              45

Asp Gly Leu Ser Ser Glu Gly Cys Leu Trp Pro Ser Glu Ser Thr Val
    50              55              60

Ser Gly Gly Met Pro Glu Pro Gln Val Tyr Ala Pro Pro Arg Pro Thr
65              70              75              80

Asp Arg Leu Ala Val Pro Pro Phe Ile Gln Arg Ser Arg Phe Gln Pro
                85              90              95

Thr Tyr Pro Tyr Leu Gln His Glu Ile Ala Leu Pro Pro Thr Ile Ser
                100             105             110

Leu Ser Asp Gly Glu Glu Pro Pro Tyr Gln Gly Pro Cys Thr Leu
        115             120             125

Gln Leu Arg Asp Pro Glu Gln Gln Leu Glu Leu Asn Arg Glu Ser Val
    130             135             140

Arg Ala Pro Pro Asn Arg Thr Ile Phe Asp Ser Asp Leu Ile Asp Ser
145             150             155             160

Thr Met Leu Gly Gly Pro Cys Pro Pro Ser Ser Asn Ser Gly Ile Ser
                165             170             175

Ala Thr Cys Tyr Ser Ser Gly Gly Arg Met Glu Gly Pro Pro Pro Thr
                180             185             190

Tyr Ser Glu Val Ile Gly His Tyr Pro Gly Ser Ser Phe Gln His Gln
                195             200             205

Gln Ser Asn Gly Pro Ser Ser Leu Leu Glu Gly Thr Arg Leu His His
    210             215             220

Ser His Ile Ala Pro Leu Glu Asn Lys Glu Lys Glu Lys Gln Lys Gly
225             230             235             240

His Pro Leu

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 69
gctgctggag aactgaaggc g                                          21

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 70
gtgtcctttc tgtttatcct tc                                         22

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 71
```

-continued

```
aagcttgctg ctggagaact gaaggcg                                          27

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 72
gaattcggtg tcctttctgt ttatc                                            25

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 73
gcaggatccc aaccagatgc tgcttgc                                          27

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 74
gcagaattct tttgtaatcc ctggagta                                         28

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 75
gcaaagcttg tccggtttgc tggaagc                                          27

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 76
gcagaattcc cttttgttc ttattggtga c                                      31

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 77
catgatcccc gagctgct                                                    18

<210> SEQ ID NO 78
<211> LENGTH: 23
<212> TYPE: DNA
```

```
<213> ORGANISM: Artificial Sequence
<220> FEATURE:
<223> OTHER INFORMATION: Description of Artificial Sequence: Primer

<400> SEQUENCE: 78
tgatctgaac aaactccagc tcc                                              23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 79
aggcggacag tctcctgcga aac                                              23

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 80

Pro Pro Pro Tyr
  1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 81

Pro Pro Thr Tyr
  1
```

ANDROGEN-REGULATED PMEPA1 GENE AND POLYPEPTIDES

CROSS REFERENCE TO RELATED APPLICATIONS

The present application is a continuation of application Ser. No. 10/434,479, filed May 9, 2003, now abandoned which is a continuation-in-part of U.S. application Ser. No. 10/390, 045, filed Mar. 18, 2003, now abandoned which is a divisional of U.S. application Ser. No. 09/769,482, filed Jan. 26, 2001, now U.S. Pat. No. 6,566,130, which is based upon U.S. Provisional Application Nos. 60/378,949, 60/178,772, and 60/179,045, filed May 10, 2002, Jan. 28, 2000, and Jan. 31, 2000, respectively, priority to which is claimed under 35 U.S.C. § 119(e). The entire disclosures of these applications are expressly incorporated herein by reference.

GOVERNMENT INTEREST

The invention described herein may be manufactured, licensed, and used for governmental purposes without payment of royalties to us thereon.

FIELD OF THE INVENTION

The present invention relates to tumor suppressor genes, and in particular, PMEPA1 genes, and the proteins encoded by these genes, including variants and/or analogs thereof. More particularly, the present invention is based in part on the discovery that PMEPA1 polypeptides inhibit cancer cell growth. The present invention also relates to novel, androgen-regulated nucleic acids, polynucleotide arrays containing androgen-regulated nucleic acids, such as PMEPA1, and methods of using the array in the evaluation of hormone-related cancers, such as prostate cancer.

BACKGROUND

Prostate cancer (CaP) is the most common malignancy in American men and second leading cause of cancer mortality (1). Serum-prostate specific antigen (PSA) tests have revolutionized the early detection of CaP (2). Although PSA has revolutionized early detection of prostate cancer, there is still a very high false positive rate. The increasing incidence of CaP has translated into wider use of radical prostatectomy as well as other therapies for localized disease (3-5). The wide spectrum of biologic behavior (6) exhibited by prostatic neoplasms poses a difficult problem in predicting the clinical course for the individual patient (3-5). Traditional prognostic markers such as grade, clinical stage, and pretreatment PSA have limited prognostic value for individual men (3-5). A more reliable technique for the evaluation and prognosis of CaP is desirable.

Molecular studies have shown a significant heterogeneity between multiple cancer foci present in a cancerous prostate gland (7,8). These studies have also documented that the metastatic lesion can arise from cancer foci other than those present in dominant tumors (7). Approximately 50-60% of patients treated with radical prostatectomy for localized prostate carcinomas are found to have microscopic disease that is not organ-confined, and a significant portion of these patients relapse (9). Therefore, identification and characterization of genetic alterations defining CaP onset and progression is crucial in understanding the biology and clinical course of the disease.

Despite recent intensive research investigations, much remains to be learned about specific molecular defects associated with CaP onset and progression (6, 10-15). Alterations of the tumor suppressor gene p53, bcl-2 and the androgen receptor (AR), are frequently reported in advanced CaP (6, 10-15). However, the exact role of these genetic defects in the genesis and progression of CaP is poorly understood (6, 10-15). Recent studies have shown that the "focal p53 immunostaining" or bcl-2 immunostaining in radical prostatectomy specimens were independent prognostic markers for cancer recurrence after surgery (16-19). Furthermore, the combination of p53 and bcl-2 alterations was a stronger predictor of cancer recurrence after radical prostatectomy (18).

The roles of several new chromosome loci harboring putative proto-oncogenes or tumor suppressor genes are being currently evaluated in CaP (7-13). High frequency of allelic losses on 8p21-22, 7q31.1, 10q23-25 and 16q24 loci have been shown in CaP (6, 10-15). PTEN1/MMAC1, a recently discovered tumor suppressor gene on chromosome 10q25, is frequently altered in advanced CaP (20, 21). Gains of chromosome 8q24 harboring c-myc and prostate stem-cell antigen (PSCA) genes have also been shown in prostate cancer (22, 23). Studies utilizing comparative genomic hybridization (CGH) have shown frequent losses of novel chromosomal loci including 2q, 5q and 6q and gains of 11p, 12q, 3q, 4q and 2p in CaP (24, 25). The inventors have recently mapped a 1.5 megabase interval at 6q16-21 which may contain the putative tumor suppressor gene involved in a subset of prostate tumors. The risk for 6q LOH to non-organ confined disease was five fold higher than for organ confined disease (26). Chromosome regions, 1q24-25 and Xq27-28 have been linked to familial CaP (27, 28).

It is evident that multiple molecular approaches need to be explored to identify CaP- associated genetic alterations. Emerging strategies for defining cancer specific genetic alterations and characterizing androgen regulated genes in rat prostate and LNCaP human prostate cancer cell models include, among others, the study of global gene expression profiles in cancer cells and corresponding normal cells by differential display (DD) (29) and more recent techniques, such as serial amplification of gene expression (SAGE) (30) and DNA micro-arrays (31; U.S. Pat. Nos. 5,744,305 and 5,837,832 which are herein incorporated by reference) followed by targeted analyses of promising candidates. Our laboratory has also employed DD, SAGE and DNA microarrays to study CaP associated gene expression alterations (32-33). Each of these techniques, however, is limited. The number of transcripts that can be analyzed is the major limitation encountered in subtractive hybridization and differential display approaches. Furthermore, while cDNA microarray approaches can determine expression of a large number of genes in a high throughput manner, the current limitations of cDNA arrays include the presence of specific arrays used for analyses and the inability to discover novel genes.

While alterations of critical tumor-suppressor genes and oncogenes are important in prostate tumorogenesis, it is also recognized that hormonal mechanisms play equally important roles in prostate tumorogenesis. The cornerstone of therapy in patients with metastatic disease is androgen ablation, commonly referred to as "hormonal therapy (34)," which is dependent on the inhibition of androgen signaling in prostate cancer cells. Androgen ablation can be achieved, for example, by orchiectomy, by the administration of estrogen, or more recently by one of the luteinizing hormone-releasing hormone agonists. Recent clinical trials have demonstrated the efficacy of combining an antiandrogen to orchiectomy or a luteinizing hormone-releasing hormone to block the remaining androgens produced by the adrenal glands. Although approximately 80% of patients initially respond to hormonal ablation, the vast majority of patients eventually relapse (35), presumably due to neoplastic clones of cells which become refractory to this therapy.

Alterations of the androgen receptor gene by mutations in the hormone binding domain of the AR or by amplification of the AR gene have been reported in advanced stages of CaP. Much remains to be learned, however, about the molecular mechanisms of the AR-mediated cell signaling in prostate growth and tumorogenesis (36-43). Our earlier studies have also described mutations of the AR in a subset of CaP (40). Mutations of the AR are reported to modify the ligand (androgen) binding of the AR by making the receptor promiscuous, so that it may bind to estrogen, progesterone, and related molecules, in addition to the androgens (36,38,42). Altered ligand binding specificity of the mutant AR may provide one of the mechanisms for increased function in cancer cells. Amplifications of the AR gene in hormone-refractory CaP represent yet another scenario where increase in AR function is associated with tumor progression (44,45).

Several growth factors commonly involved in cell proliferation and tumorogenesis, e.g., IGF1, EGF, and others, have been shown to activate the transcription transactivation functions of the AR (46). The co-activator of the AR transcription factor functions may also play a role in prostate cancer (47). Recent studies analyzing expression of the androgen-regulated genes (ARGs) in hormone sensitive and refractory CWR22 nude mice xenograft models (48) have also shown expression of several androgen regulated genes in AR positive recurrent tumors following castration, suggesting activation of AR in these tumors (49).

In addition to the alterations of the androgen signaling pathway(s) in prostate tumor progression, androgen mechanisms are suspected to play a role in the predisposition to CaP. Prolonged administration of high levels of testosterone has been shown to induce CaP in rats (50-52). Although recent evidence suggests an association of androgen levels and risk of CaP, this specific observation remains to be established. (53). An independent line of investigations addressing the length of inherited polyglutamine (CAG) repeat sequence in the AR gene and CaP risk have shown that men with shorter repeats were at high risk of distant metastasis and fatal CaP (54,55). Moreover, the size distribution of AR CAG repeats in various ethnic groups has also suggested a possible relationship of shorter CAG repeats and increased prostate cancer risks in African-American men (56,57). Biochemical experiments evaluating AR-CAG repeat length and in vitro transcription transactivation functions of the AR revealed that AR with shorter CAG repeats possessed a more potent transcription trans-activation activity (58). Thus, molecular epidemiologic studies and biochemical experimentation suggest that gain of AR function, consequently resulting in transcriptional transactivation of downstream targets of the AR gene, may play an important role in CaP initiation. However, downstream targets of AR must be defined in order to understand the biologic basis of these observations.

The biologic effects of androgen on target cells, e.g., prostatic epithelial cell proliferation and differentiation as well as the androgen ablation-induced cell death, are likely mediated by transcriptional regulation of ARGs by the androgen receptor (reviewed in 59). Abrogation of androgen signaling resulting from structural changes in the androgen gene or functional alterations of AR due to modulation of AR functions by other proteins would have profound effects on transcriptional regulation of genes regulated by AR and, thus, on the growth and development of the prostate gland, including abnormal growth characterized by benign prostatic hyperplasia and prostatic cancer. The nature of ARGs in the context of CaP initiation and progression, however, remains largely unknown. Since forced proliferation of the AR prostate cancer cells lacking AR induces cell-death related phenotypes (60), the studies utilizing AR expression via heterologous promoters in cell cultures have failed to address the observations relating to gain of AR functions and prostate cancer progression. Moreover, suitable animal models to assess gain of AR functions do not exist. Therefore, the expression profile of androgen responsive genes (ARGs) has potential to serve as read-out of the AR signaling status. Such a read-out may also define potential biomarkers for onset and progression of those prostate cancers which may involve abrogation of the androgen signaling pathway. Furthermore, functional analysis of androgen regulated genes will help understand the biochemical components of the androgen signaling pathways.

SUMMARY OF THE INVENTION

The present invention relates to the identification and characterization of a novel androgen-regulated gene that exhibits abundant expression in prostate tissue. The novel gene has been designated PMEPA1. Our work with PMEPA1 is further described in U.S. Provisional Application No. 60/378,949, filed May 10, 2002, and PCT Application No. PCT/US03/13401, filed May 9, 2003, the entire disclosures of which are hereby incorporated by reference.

The invention provides the isolated nucleotide sequence of PMEPA1 or fragments thereof and nucleic acid sequences that hybridize to PMEPA1. These sequences have utility, for example, as markers of prostate cancer and other prostate-related diseases, and as targets for therapeutic intervention in prostate cancer and other prostate-related diseases. The invention further provides a vector that directs the expression of PMEPA1, and a host cell transfected or transduced with this vector.

In another embodiment, the invention provides a method of detecting prostate cancer cells in a biological sample, for example, by using nucleic acid amplification techniques with primers and probes selected to bind specifically to the PMEPA1 sequence.

In another aspect, the invention relates to an isolated polypeptide encoded by the PMEPA1 gene or a fragment thereof, and antibodies generated against the PMEPA1 polypeptide, peptides, or portions thereof, which can be used to detect, treat, and prevent prostate cancer.

In another aspect, the invention provides variants of the PMEPA1 polypeptide that retain at least one of the following abilities: inhibiting cancer cell growth, reducing the expression of an androgen receptor, or modulating the expression of a gene whose transcription is regulated by the androgen receptor. In one embodiment, these variants are at least 95% identical to SEQ ID NO:3 and inhibit the growth of prostate cancer cells (e.g., LNCaP cells), as measured, for example, in a colony-forming assay.

In another aspect, the invention provides a method of inhibiting the growth of a cancer cell, comprising administering these variants to the cancer cell in an amount effective to inhibit the growth of the cancer cell. In one embodiment the cancer cell is a prostate cancer cell. The polypeptide may be administered directly to the cell or indirectly using a vector containing a polynucleotide sequence that encodes the variant. These methods include therapeutic methods of treating cancer, and in particular, prostate cancer.

A further embodiment of the invention provides a method of reducing the expression of an androgen receptor or modulating the expression of genes that are transcriptionally regulated by androgen receptor, including, but not limited to the prostate-specific antigen (PSA) gene, the PSMA gene, and the PCGEM1 gene. Thus, in one aspect, the invention provides a method of reducing the expression in a cancer cell of an androgen receptor or modulating (i.e., increasing or decreasing) the expression of a gene whose transcription is regulated by the androgen receptor, comprising administering the variants described above to the cancer cell, in an amount effective to reduce the androgen receptor or modulate the expression of the gene in the cancer cell. In one embodiment the cancer cell is a prostate cancer cell. The polypeptide may be administered directly to the cell or indirectly using a vector containing a polynucleotide sequence that encodes the variant.

In yet another aspect, the invention provides variants of the PMEPA1 polypeptide having at least one mutation and/or deletion in the at least one of the PY motifs of PMEPA1, as discussed in further detail below. Such mutations reduce the cell growth inhibitory effects of PMEPA1. These PMEPA1 variants can be used, for example, to define cellular proteins through which PMEPA1 interacts, directly or indirectly, to mediate cell growth inhibitory functions.

In a still further embodiment, the invention provides the polynucleotides that encode the PMEPA1 variants, as well as methods (as described above for a polypeptide comprising SEQ ID NO:3) of using these variants, for example, to inhibit cancer cell growth, including prostate cancer, and/or to reduce the expression of an androgen receptor and/or to modulate the expression of a gene whose transcription is regulated by the androgen receptor.

The present invention also relates to a polynucleotide array comprising (a) a planar, non-porous solid support having at least a first surface; and (b) a first set of polynucleotide probes attached to the first surface of the solid support, where the first set of polynuceotide probes comprises polynucleotide sequences derived from genes that are up-regulated, such as PMEPA1, or down-regulated in response to androgen, including genes downstream of the androgen receptor gene and genes upstream of the androgen receptor gene that modulate androgen receptor function. In another embodiment of the invention the polynucleotides immobilized on the solid support include genes that are known to be involved in testosterone biosynthesis and metabolism. In another embodiment of the invention the oligonucleotides immobilized on the solid support include genes whose expression is altered in prostate cancer or is specific to prostate tissue.

In another embodiment, the invention provides a method for the diagnosis or prognosis of prostate cancer, comprising (a) hybridizing nucleic acids of a target cell of a patient with a polynucleotide array, as described above, to obtain a first hybridization pattern, where the first hybridization pattern represents an expression profile of androgen-regulated genes in the target cell; (b) comparing the first hybridization pattern of the target cell to a second hybridization pattern, where the second hybridization pattern represents an expression profile of androgen-regulated genes in prostate cancer, and (c) diagnosing or prognosing prostate cancer in the patient.

Thus, a first aspect of the present invention is directed towards a method for analysis of radical prostatectomy specimens for the expression profile of those genes involved in androgen receptor-mediated signaling. In a preferred embodiment, computer models may be developed for the analysis of expression profiles. Another aspect of the invention is directed towards a method of correlating expression profiles with clinico-pathologic features. In a preferred embodiment, computer models to identify gene expression features associated with tumor phenotypes may be developed. Another aspect of the invention is directed towards a method of distinguishing indolent prostate cancers from those with a more aggressive phenotype. In a preferred embodiment, computer models to such cancers may be developed. Another aspect of the invention is directed towards a method of analyzing tumor specimens of patients treated by radical prostate surgery to help define prognosis. Another aspect of the invention is directed towards a method of screening candidate genes for the development of a blood test for improved prostate cancer detection. Another aspect of the invention is directed towards a method of identifying androgen regulated genes that may serve as biomarkers for response to treatment to screen drugs for the treatment of advanced prostate cancer.

This invention is further directed to a method of identifying an expression profile of androgen-regulated genes in a target cell, comprising hybridizing the nucleic acids of the target cell with a polynucleotide array, as described above, to obtain a hybridization pattern, where the hybridization pattern represents the expression profile of androgen-regulated genes in the target cell.

Additional features and advantages of the invention will be set forth in the description which follows, and in part will be apparent from the description, or may be learned by practice of the invention.

BRIEF DESCRIPTION OF THE DRAWINGS

FIG. 2 shows the androgen-dependent expression of PMEPA1.

FIG. 4A shows PMEPA 1-mediated down regulation of androgen receptor and its functional consequences on androgen receptor regulated genes. LNCaP cells stably transfected with PMEPA1-GFP and pEGFP (control) plasmids were cultured in medium with cFBS for 5 days and then were stimulated with R1881 at 0.1 nM. Cells were harvested for Western blotting at 0 h, 12 h and 24 h after androgen stimulation.

Antibodies against androgen receptor, PSA, PSMA and tubulin were used to detect corresponding proteins on Western Blots.

FIG. 4B shows that PMEPA1 does not reduce androgen receptor expression through a non-specific, PMEPA1-induced effect on the ubiquitin-proteasome pathway. Stable PMEPA1-GFP-Tet -LNCaP transfectants (Tet-off system) were cultured in proper medium with or without tetracycline for 10 days and were applied for immunoblotting. Antibodies against androgen receptor, GFP, p27 and tubulin were used to detect the corresponding proteins.

Figure 5:
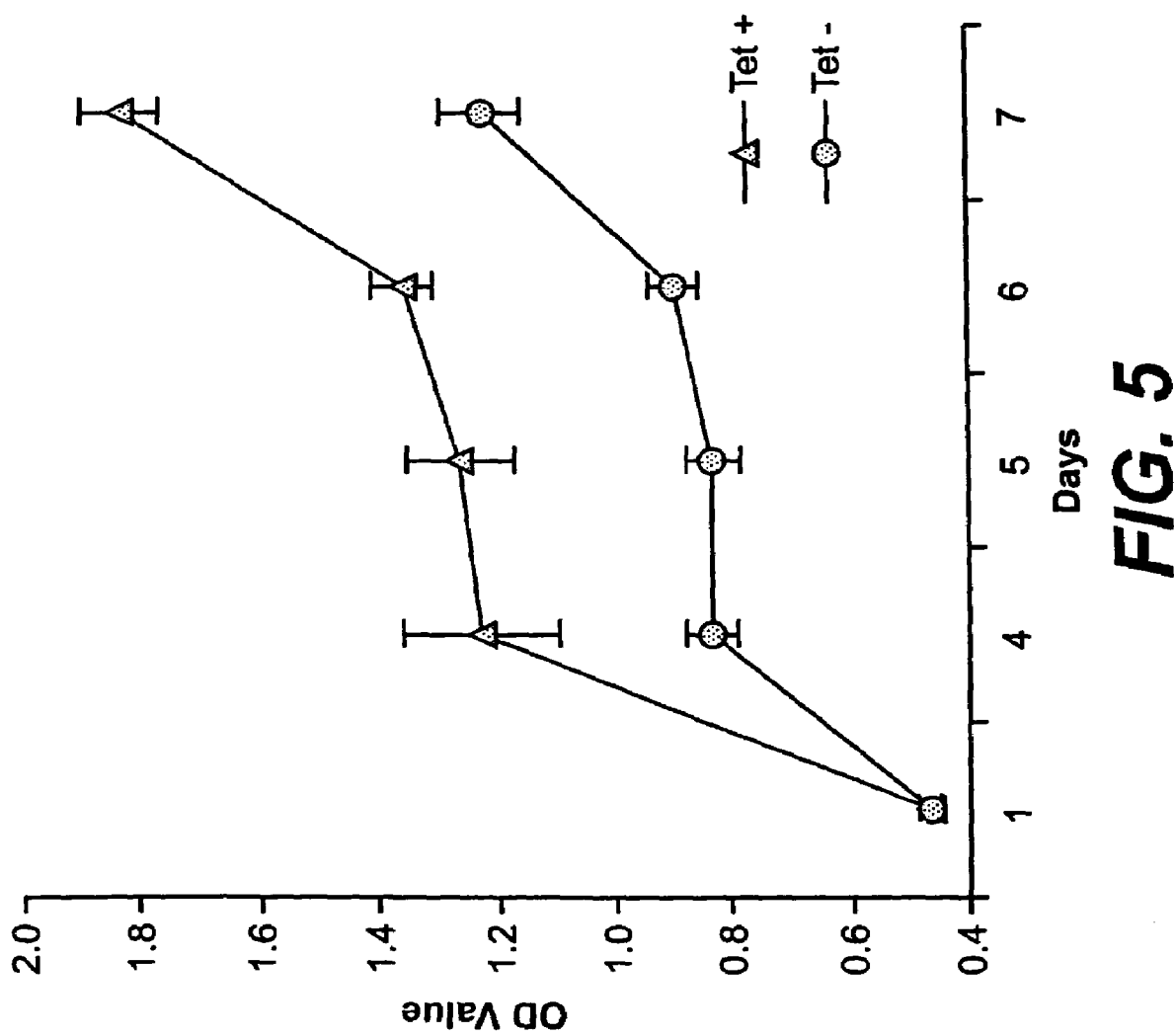

FIG. 5 shows the effect of PMEPA1 on cell proliferation. Stable PMEPA1-GFP-Tet-LNCaP transfectants were seeded in 96-well plates with or without 1 µg/ml of tetracycline in the medium. The cell proliferation was measured using the Cell-Titer 96 Aqueous One Solution kit at the indicated time. Tet+ and Tet− denote the cell culture medium with or without tetracycline, respectively. The OD values reflecting the cell numbers are significantly different ($p<0.01$) between the two groups except on day one.

Figure 6:
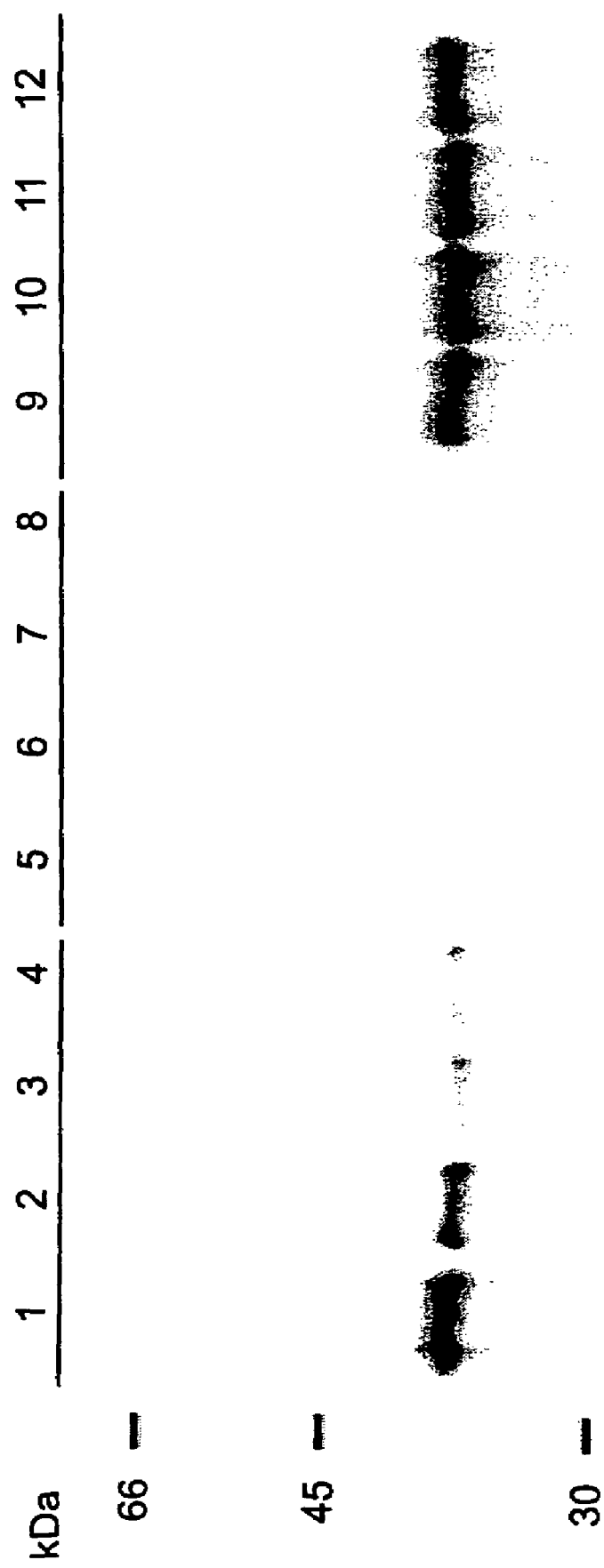

FIG. 6 defines binding of PMEPA1 to NEDD4 proteins. The in vitro transcription/translation products ($[^{35}S]$Methionine-labeled lysates) derived from expression plasmids: PMEPA1-V5-pcDNA3.1 (Lanes 1, 5), PMEPA1-PY1m-pcDNA3.1 (Lanes 2, 6), PMEPA1-PY2m-pcDNA3.1 (Lanes 3, 7), and PMEPA1-PY1m/PY2m-pcDNA3.1 (Lanes 4, 8) were incubated with GST-NEDD4-WW-Sepharose beads (Lanes 1-4) or control GST beads (Lanes 5-8) and $[^{35}S]$ Methionine labeled proteins bound to GST-NEDD4-WW-Sepharose beads were solublized in sample buffer and were resolved by SDS-PAGE gel. Equal amounts of $[^{35}S]$Methionine lysates corresponding to samples in lanes 1-4 were run on SDS-PAGE gel without GST pull-down (Lane 9-12).

FIG. 7 represents an immunoprecipitation assay. 293 cells were co-transfected with expression vectors encoding NEDD4-GFP and one of following fusion proteins: PMEPA1-V5 (Lane 1), PMEPA1-PY1m-V5 (Lane 2), PMEPA1-PY2m-V5 (Lane 3) or PMEPA1-PY1m/PY2m-V5 (Lane 4). The cell lysates from each group were immunoprecipitated with anti-GFP antibody then subjected to immunoblotting (blot a). Cell lysates from each group without immunoprecipitation were also processed for immunoblotting (blots b and c) to serve as a control. Blots a and b were detected by anti-V5 antibody and blot c was detected by anti-GFP antibody.

Figure 8:
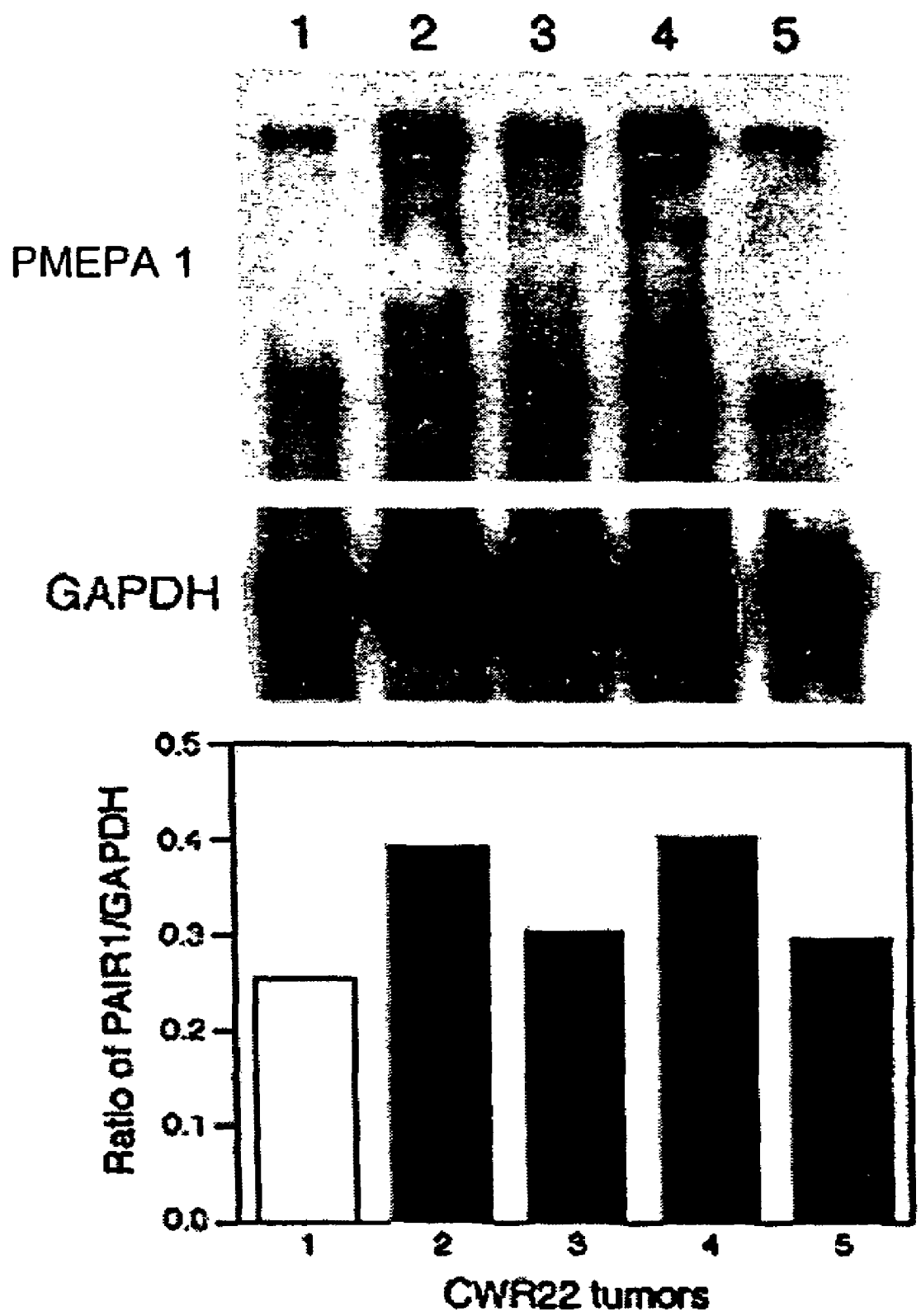

FIG. 8 shows PMEPA1 expression in CWR22 xenograft tumors. Lane 1, sample from CWR22 tumor (androgen dependent). Lanes 2-5, samples from 4 individual CWR22R tumors (AR positive but androgen independent).

DETAILED DESCRIPTION OF THE INVENTION

The present invention provides a method useful in the diagnosis and prognosis of prostate cancer. An aspect of the invention provides a method to identify ARGs, such as PMEPA1, that exhibit stable transcriptional induction/repression in response to androgen and have potential as surrogate markers of the status of the androgen signaling in normal and cancerous epithelial cells of prostate.

A second aspect of the invention provides for use of the expression profiles resulting from these methods in diagnostic methods, including, but not limited to, characterizing the treatment response to "hormonal therapy," correlating expression profiles with clinico-pathologic features, distinguishing indolent prostate cancers from those with a more aggressive phenotype, analyzing tumor specimens of patients treated by radical prostate surgery to help define prognosis, screening candidate genes for the development of a polynucleotide array for use as a blood test for improved prostate cancer detection, and identifying androgen regulated genes that may serve as biomarkers for response to treatment to screen drugs for the treatment of advanced prostate cancer.

As will be readily appreciated by persons having skill in the art, these gene sequences and ESTs described herein can easily be synthesized directly on a support, or pre-synthesized polynucleotide probes may be affixed to a support as described, for example, in U.S. Pat. Nos. 5,744,305, 5,837, 832, and 5,861,242, each of which is incorporated herein by reference. Furthermore, such arrays may be made in a wide number of variations, combining, probes derived from sequences identified by the inventors as up-regulated or down-regulated in response to androgen and listed in Table 3 (genes and ESTs derived from the inventors' SAGE library that are up-regulated and down-regulated by androgens) with any of the sequences described in Table 4 (candidate genes and ESTs whose expression are potentially prostate specific or restricted), Table 5 (previously described genes and ESTs, including those associated with androgen signaling, prostate specificity, prostate cancer, and nuclear receptors/regulators with potential interaction with androgen receptors), Table 6 (genes and ESTs identified from the NIH CGAP database that are differentially expressed in prostate cancer), Table 7 (androgen regulated genes and ESTs derived from the CPDR Genome Systems ARG Database) and Table 8 (other genes associated with cancers). Tables 3-8 are located at the end of the specification at the end of the "Detailed Description" section and before the "References." In Table 3, genes in bold type are known androgen-regulated genes based on Medline Search. In Table 4, genes in bold type are known prostate-specific genes.

Such arrays may be used to detect specific nucleic acid sequences contained in a target cell or sample, as described in U.S. Pat. Nos. 5,744,305, 5,837,832, and 5,861,242, each of which is incorporated herein by reference. More specifically, in the present invention, these arrays may be used in methods for the diagnosis or prognosis of prostate cancer, such as by assessing the expression profiles of genes, derived from biological samples such as blood or tissues, that are up-regulated and down-regulated in response to androgen or otherwise involved in androgen receptor-mediated signaling. In a preferred embodiment, computer models may be developed for the analysis of expression profiles. Moreover, such polynucleotide arrays are useful in methods to screen drugs for the treatment of advanced prostate cancer. In these screening methods, the polynucleotide arrays are used to analyze how drugs affect the expression of androgen-regulated genes that are involved in prostate cancer.

SAGE analysis. The SAGE technology is based on three main principles: 1) A short sequence tag (10-11 bp) is generated that contains sufficient information to identify a transcript, thus, each tag represents a signature sequence of a unique transcript; 2) many transcript tags can be concatenated into a single molecule and then sequenced, revealing the identity of multiple tags simultaneously; 3) quantitation of the number of times a particular tag is observed provides the expression level of the corresponding transcript (30). The schematic diagram and the details of SAGE procedure can be obtained from the web site provided by Genzyme.

About fifty percent of SAGE tags identified by the inventors represent ESTs which need to be further analyzed for their protein coding capacity. The known genes up-regulated or down-regulated by four-fold ($p<0.05$) were broadly classified on the basis of the biochemical functions. SAGE tag defined ARGs were grouped under following categories: transcriptional regulators; RNA processing and translation regulators; protein involved in genomic maintenance and cell cycle; protein trafficking/chaperone proteins; energy metabolism, apoptosis and redox regulators; and signal transducers. As determined by PubMed database searches, a majority of genes listed in Table 3 have not been described as androgen regulated before. This is the first comprehensive list of the functionally defined genes regulated by androgen in the context of prostatic epithelial cells.

Although promising candidate ARGs have been identified using these approaches, much remains to be learned about the complete repertoire of these genes. SAGE provides both quantitative and high throughput information with respect to global gene expression profiles of known as well as novel transcripts. We have performed SAGE analysis of the ARGs in the widely studied hormone responsive LNCaP prostate cancer cells treated with and without synthetic androgen, R1881. Of course, this SAGE technique could be repeated with hormones other than R1881, including other synthetic or natural androgens, such as dihydroxytestosterone, to potentially obtain a slightly different ARG expression panel. A goal of the inventors was to identify highly induced and repressed ARGs in LNCaP model which may define a panel of surrogate markers for the status androgen signaling in normal as well as cancerous prostate. Here, we report identification and analyses of a comprehensive database of SAGE tags corresponding to well-characterized genes, expressed sequence tags (ESTs) without any protein coding information and SAGE tags corresponding to novel transcripts. This is the first report describing a quantitative evaluation of the global gene expression profiles of the ARGs in the context of prostatic cancer cells by SAGE. We have further defined the ARGs on the basis of their known biologic/biochemical functions. Our study provides quantitative information on about 23,000 transcripts expressed in LNCaP cells, the most common cell line used in prostate cancer research. Finally, comparison of the LNCaP SAGE tag library and 35 SAGE tag libraries representing diverse cell type/tissues have unraveled a panel of genes whose expression are prostate specific or prostate abundant. Utilizing the LNCAP prostate cancer cells, the only well-characterized androgen responsive prostatic epithelial cells (normal or cancerous), we have identified a repertoire of androgen regulated genes by SAGE.

Utilizing cell-culture systems and cell-signaling agents or exogenous expression of p53 and APC genes, SAGE technology has identified novel physiologically relevant transcriptional target genes which have unraveled new functions of p53 and APC genes (61-64). Our analysis of ARGs has provided identification and quantitative assessment of induction or repression of a global expression profile of ARGs in LNCaP cells. ARGs resulting from the mutational defects of the AR and those ARGs unaffected by AR mutations may be identified in this model system. Subsequent androgen regulation analysis of the selected ARGs in AR-positive, primary cultures of normal prostatic epithelial cells, and ARGs expression analysis in normal and tumor tissues will clarify normal or abnormal regulation of these ARGs. A panel of highly inducible/repressible ARGs identified by the inventors may provide bio-indicators of the AR transcription factor activity in physiologic context. These AR Function Bio-indicators (ARFBs) are useful in assessing the risk of CaP onset and/or progression. Moreover, identification or ARGs may also help in defining the therapeutic targets which could lead to effective treatment for hormone refractory cancer, currently a frustrating stage of the disease with limited therapeutic options.

Characterization of a SAGE-defined EST that exhibited the highest level of induction in LNCaP cells responding to R1881 led to the discovery of a novel, androgen-induced gene, PMEPA1, which encodes a polypeptide with a type Ib transmembrane domain. A Protein sequence similarity search showed homology to C18orf1, a novel gene located on chromosome 18 that is mainly expressed in brain with multiple transcriptional variants (Yoshikawa et al., 1998). In addition to the sequence similarity, PMEPA1 also shares other features with C18orf1, e.g., similar size of the predicted protein and similar transmembrane domain as the $\beta1$ isoform of C18orf1. Therefore, it is likely that other isoforms of PMEPA1 may exist.

Database searches showed that the PMEPA1 sequence matched to genomic clones RP5-1059L7 and 718J7 which were mapped to chromosome 20q13.2-13.33. Gain of 20q has been observed in many cancer types, including prostate, bladder, melanoma, colon, pancreas and breast (Brothman et al., 1990; Richter et al., 1998; Bastian et al., 1998; Korn et al., 1999; Mahlamaki et al., 1997; Tanner et al., 1996). Chromosome 20q gain was also observed during immortalization and may harbor genes involved in bypassing senescence (Jarrard et al., 1999; Cuthill et al., 1999). A differentially expressed gene in hormone refractory CaP, UEV-1, mapped to 20q13.2 (Stubbs et al., 1999). These observations indicate that one or several genes on chromosome 20q may be involved in prostate or other cancer progression. Although we did not observe increased expression of PMEPA1 in primary prostate tumors, increased PMEPA1 expression was noted in recurrent cancers of CWR22 xenograft.

PMEPA1 expression is upregulated by androgens in a time- and concentration-specific manner in LNCaP cells. This observation underscores the potential of measuring PMEPA1 expression as one of the surrogate markers of androgen receptor activity in vivo in the epithelial cells of prostate tissue. Prostate cancer is androgen dependent and its growth in prostate is mediated by a network of ARGs that remains to be fully characterized. Most prostate cancers respond to androgen withdrawal but relapse after the initial response (Koivisto et al., 1998). The growth of the relapsed tumors is androgen independent even though tumors are positive for the expression of the AR (Bentel et al., 1996).

One of the hypotheses of how cancer cells survive and grow in the low androgen environment is the sensitization or the activation of the AR pathway (Jenster et al., 1999). Studies have shown increased expression of the ARGs or amplification of AR in androgen independent prostate cancer tissues (Gregory et al., 1998; Lin et al., 1999). We have observed that PMEPA1 was expressed in all CWR22R tumors and increased expression in three of four compared with CWR22 tumor. Our data support the concept that normally AR-dependent pathways remain activated, despite the absence of androgen in androgen-independent prostate cancer. There are only limited studies that have addressed whether ARGs play a role in the transition from androgen dependent tumor to androgen independent tumors. The high level of expression only in the prostate gland indicates that PMEPA1 might have important roles related to prostate cell biology or physiology. On the basis of homology of PMEPA1 to C18orf1 it is tempting to suggest that the PMEPA1 may belong to family of proteins involved in the binding of calcium and LDL.

ARGs, including PMEPA1, can be used as biomarkers of AR function readout in the subset of prostate cancers that may involve abrogation of androgen signaling. Furthermore, the newly defined ARGs have potential to identify novel targets in therapy of hormone refractory prostate cancer.

The nucleic acid molecules encompassed in the invention include the following PMEPA1 nucleotide sequence:

```
                                                        (SEQ ID NO.2)
ATGGCGGAGC TGGAGTTTGT TCAGATCATC ATCATCGTGG TGGTGATGAT      50
GGTGATGGTG GTGGTGATCA CGTGCCTGCT GAGCCACTAC AAGCTGTCTG     100
CACGGTCCTT CATCAGCCGG CACAGCCAGG GGCGGAGGAG AGAAGATGCC     150
CTGTCCTCAG AAGGATGCCT GTGGCCCTCG GAGAGCACAG TGTCAGGCAA     200
CGGAATCCCA GAGCCGCAGG TCTACGCCCC GCCTCGGCCC ACCGACCGCC     250
TGGCCGTGCC GCCCTTCGCC CAGCGGGAGC GCTTCCACCG CTTCCAGCCC     300
ACCTATCCGT ACCTGCAGCA CGAGATCGAC CTGCCACCCA CCATCTCGCT     350
GTCAGACGGG GAGGAGCCCC CACCCTACCA GGGCCCCTGC ACCCTCCAGC     400
TTCGGGACCC CGAGCAGCAG CTGGAACTGA ACCGGGAGTC GGTGCGCGCA     450
CCCCCAAACA GAACCATCTT CGACAGTGAC CTGATGGATA GTGCCAGGCT     500
GGGCGGCCCC TGCCCCCCCA GCAGTAACTC GGGCATCAGC GCCACGTGCT     550
ACGGCAGCGG CGGGCGCATG GAGGGGCCGC CGCCCACCTA CAGCGAGGTC     600
ATCGGCCACT ACCCGGGGTC CTCCTTCCAG CACCAGCAGA GCAGTGGGCC     650
GCCCTCCTTG CTGGAGGGGA CCCGGCTCCA CCACACACAC ATCGCGCCCC     700
TAGAGAGCGC AGCCATCTGG AGCAAAGAGA AGGATAAACA GAAAGGACAC     750
CCTCTCTAG                                                  759
```

The amino acid sequences of the polypeptides encoded by the PMEPA1 nucleotide sequences of the invention include:

```
                                                        (SEQ ID NO.3)
MAELEFVQII IIVVVMMVMV VVITCLLSHY KLSARSFISR HSQGRRREDA      50
LSSEGCLWPS ESTVSGNGIP EPQVYAPPRP TDRLAVPPFA QRERFHRFQP     100
TYPYLQHEID LPPTISLSDG EEPPPYQGPC TLQLRDPEQQ LELNRESVRA     150
PPNRTIFDSD LMDSARLGGP CPPSSNSGIS ATCYGSGGRM EGPPPTYSEV     200
IGHYPGSSFQ HQQSSGPPSL LEGTRLHHTH IAPLESAAIW SKEKDKQKGH     250
PL*                                                        252
```

The discovery of the nucleic acids of the invention enables the construction of expression vectors comprising nucleic acid sequences encoding polypeptides; host cells transfected or transformed with the expression vectors; isolated and purified biologically active polypeptides and fragments thereof; the use of the nucleic acids or oligonucleotides thereof as probes to identify nucleic acid encoding proteins having PMEPA1-like activity; the use of single-stranded sense or antisense oligonucleotides from the nucleic acids to inhibit expression of polynucleotides encoded by the PMEPA1 gene; the use of such polypeptides and fragments thereof to generate antibodies; the use of the antibodies to purify PMEPA1 polypeptides; and the use of the nucleic acids, polypeptides, and antibodies of the invention to detect, prevent, and treat prostate cancer (e.g., prostatic intraepithelial neoplasia (PIN), adenocarcinomas, nodular hyperplasia, and large duct carcinomas) and prostate-related diseases (e.g., benign prostatic hyperplasia).

As summarized below and explained in further detail in the Examples that follow, our evaluation of PMEPA1 indicates it is a prostate-abundant androgen regulated gene with roles in cell growth control and tumorigenesis. Loss or reduced PMEPA1 expression in prostate cancer correlates with a higher risk or probability of prostate tumorigenesis or progression (e.g., advanced stages of prostate cancer, such as non-organ defined cancer, where tumors extend beyond the prostate gland), particularly after surgery as primary therapy. Thus, alterations in the level, expression, and activity of PMEPA1 and/or its encoded polypeptide provides useful information about the clinical behavior of prostate cancer. Part of our evaluation involved a PMEPA1 protein sequence homology search that showed 83% identity to a recently reported gene, N4WBP4 (Example 8). N4WBP4 encodes a NEDD4 WW domain binding protein with two PY motifs that is expressed in mouse embryo [Jolliffe et al., *Biochem. J.,* 351: 557-565, 2000]. The PY motif is a proline-rich peptide sequence with a consensus PPXY sequence (where X can be any amino acid) that can bind to proteins with WW domains [Jolliffe et al., *Biochem. J.,* 351: 557-565, 2000; Harvey K et al., *Trends Cell Biol.,* 9: 166-169, 1999; Hicke L, *Cell,* 106: 527-530, 2001; Kumar et al., *Biochem. Biophys. Res. Com-*

*mun.*, 185: 1155-1161, 1992; Kumar et al., *Genomics*, 40: 435-443, 1997; Sudol M, *Trends Biochem. Sci.*, 21: 161-163, 1996; Harvey et al., *J. Biol. Chem.*, 277: 9307-9317, 2002; and Brunschwig et al., Cancer Res., 63: 1568-1575, 2003]. NEDD4 was originally identified as a developmentally regulated gene in mice and is a ubiquitin-protein ligase (E3) that is involved in the ubiquitin-dependent proteasome-mediated protein degradation pathway. Further studies revealed that NEDD4 is implicated in diverse cellular functions, such as regulation of membrane channels and permeases, endocytosis, virus budding, cell cycle, transcription and protein trafficking [Harvey et al., *Trends Cell Biol.*, 9: 166-169, 1999; Hicke L, Cell, 106: 527-530, 2001]. The WW domain present in the NEDD4 protein is a module with two highly conserved tryptophans that bind to several target proteins containing a PY motif.

As explained in Example 9, we discovered that PMEPA1 is a NEDD4 binding protein and that the binding of PMEPA1 to NEDD4 is mediated by the PY motifs of PMEPA1. Mutating the PY motifs significantly reduces the binding of PMEPA1 to NEDD4. In addition, the homology of PMEPA1 to the NEDD4-binding protein indicates that PMEPA1 may also regulate protein turnover via ubiquitinylation and proteasome pathways in the cell. This is further supported by our observation that PMEPA1 localizes to the Golgi apparatus (Example 11).

Further, we recently found that PMEPA1 expression in LNCaP cells down regulates androgen receptor protein and modulates the expression of genes that are transcriptionally regulated by androgen receptor (Example 10). This shows that PMEPA1 functions in androgen receptor regulation.

Our data also show that PMEPA1 inhibits the growth of prostate cancer cells (Example 12). More specifically, the coding region of PMEPA1 was inserted into an expression vector and transfected into 293 cell (kidney) and LNCaP cells (prostate cancer). Cell proliferation and cell cycle analysis showed that there was no difference between PMEPA1 overexpressed 293 cell and control vector transfected 293 cells. However LNCaP cells overexpressing PMEPA1 exhibited significant cell growth inhibition. Similar growth inhibition was observed in other prostate cancer cell lines.

In addition, in a quantitative evaluation of PMEPA1 expression in primary prostate cancers, we found that 40 of 62 (64.5%) matched prostate specimens exhibited decreased expression of PMEPA1 in tumor tissues, indicating a correlation between reduced PMEPA1 expression and prostate tumorigenesis (Example 13). When these expression patterns were stratified by organ confined and non-organ confined tumors, a higher percentage of patients exhibited reduced expression of PMEPA1 in non-organ confined tumor (68%) vs. organ-confined tumor (44%), indicating that reduced PMEPA1 expression correlates with an increased probability of advanced prostate cancer.

Nucleic Acid Molecules

In a particular embodiment, the invention relates to certain isolated nucleotide sequences that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in (Sambrook et al., *Molecular Cloning: A Laboratory Manual*, 3rd ed., Cold Spring Harbor Laboratory, Cold Spring Harbor, N.Y. (www-.molecularcloning.com). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the SEQ ID NO:1 or SEQ ID NO:2, or a suitable fragment thereof, as a probe.

The DNA molecules of the invention include full length genes as well as polynucleotides and fragments thereof. The full length gene may also include the N-terminal signal peptide. Other embodiments include DNA encoding a soluble form, e.g., encoding the extracellular domain of the protein, either with or without the signal peptide.

The nucleic acids of the invention are preferentially derived from human sources, but the invention includes those derived from non-human species, as well.

Preferred Sequences

The particularly preferred nucleotide sequence of the invention is SEQ ID NO:2, as set forth above. The sequence of amino acids encoded by the DNA of SEQ ID NO:2 is shown in SEQ ID NO:3.

Additional Sequences

Due to the known degeneracy of the genetic code, where more than one codon can encode the same amino acid, a DNA sequence can vary from that shown in SEQ ID NO:2, and still encode a polypeptide having the amino acid sequence of SEQ ID NO:3. Such variant DNA sequences can result from silent mutations (e.g., occurring during PCR amplification), or can be the product of deliberate mutagenesis of a native sequence.

The invention thus provides isolated DNA sequences encoding polypeptides of the invention, selected from: (a) DNA comprising the nucleotide sequence of SEQ ID NO:2; (b) DNA encoding the polypeptide of SEQ ID NO:3; (c) DNA capable of hybridization to a DNA of (a) or (b) under conditions of moderate stringency and which encode polypeptides of the invention, wherein the polypeptides inhibit the growth of LNCaP cells in a colony-forming assay; (d) DNA capable of hybridization to a DNA of (a) or (b) under conditions of high stringency and which encodes polypeptides of the invention, wherein the polypeptides inhibit the growth of LNCAP cells in a colony-forming assay, and (e) DNA which is degenerate as a result of the genetic code to a DNA defined in (a), (b), (c), or (d) and which encode polypeptides of the invention. Of course, polypeptides encoded by such DNA sequences are encompassed by the invention.

As used herein, conditions of moderate stringency can be readily determined by those having ordinary skill in the art based on, for example, the length of the DNA. The basic conditions are set forth by (Sambrook et al. *Molecular Cloning: A Laboratory Manual*, $3^{rd}$ ed., Cold Spring Harbor Laboratory Press, (www.molecularcloning.com)), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2× SSC, 0.1% SDS. The skilled artisan will recognize that the temperature and wash solution salt concentration can be adjusted as necessary according to factors such as the length of the probe.

Also included as an embodiment of the invention is DNA encoding polypeptide fragments and polypeptides comprising inactivated N-glycosylation site(s), inactivated protease processing site(s), or conservative amino acid substitution(s), as described below.

In another embodiment, the nucleic acid molecules of the invention also comprise nucleotide sequences that are at least 80% identical to a native sequence (e.g., SEQ ID NO:2). Also contemplated are embodiments in which a nucleic acid molecule comprises a sequence that is at least 90% identical, at least 95% identical, at least 98% identical, at least 99% identical, or at least 99.9% identical to a native sequence (e.g., SEQ ID NO:2).

The percent identity may be determined by visual inspection and mathematical calculation. Alternatively, the percent identity of two nucleic acid sequences can be determined by comparing sequence information using the GAP computer program, version 6.0 described by (Devereux et al., *Nucl. Acids Res.*, 12:387 (1984)) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of (Gribskov and Burgess, *Nucl. Acids Res.*, 14:6745 (1986)), as described by (Schwartz and Dayhoff, eds., *Atlas of Protein Sequence and Structure*, National Biomedical Research Foundation, pp. 353-358 (1979)); (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding a PMEPA1 polypeptide, or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be used to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in (Saiki et al., *Science*, 239:487 (1988)); (Wu et al., *Recombinant DNA Methodology*, eds., Academic Press, Inc., San Diego, pp. 189-196 (1989)); and (Innis et al., *PCR Protocols: A Guide to Methods and Applications*, eds., Academic Press, Inc. (1990)).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

Polypeptides and Fragments Thereof

The polypeptides of the invention include full length proteins encoded by the nucleic acid sequences set forth above. Particularly preferred polypeptides comprise the amino acid sequence of SEQ ID NO:3.

As discussed in Example 8, SEQ ID NO:3 shares 83% identity to a NEDD4 WW binding protein and contains two PY motifs, i.e., PPPY (SEQ ID NO:80) ("PY1") and PPTY (SEQ ID NO:81) ("PY2"). The PPXY motif, where X can be any amino acid, has been shown to facilitate binding with WW domain-containing proteins. We demonstrate in the Examples that PMEPA1 binds to the NEDD4 protein, which contains WW domains. NEDD4 is a ubiquitin-protein ligase (E3) that is involved in the ubiquitin-dependent proteasome-mediated protein degradation pathway.

Assays for determining whether a polypeptide, such as PMEPA1, binds to other proteins having a WW domain are well-known in the art and include strategies such as combinatorial peptide libraries, affinity chromatography, expression library screening, and yeast two-hybrid screening (Kay et al. (2000) FEBS Lett., 480:55-62; Frederick et al. (1999) Mol. Cell. Biol., 19: 2330-2337; Dai and Pendergast (1995) Genes Dev., 9:2569-2582; Kitamura et al. (1996) Biochem. Biophys. Res. Commun., 219:509-514; Richard et al. (1995) Mol. Cell. Biol. 15:186-197; and Sudol (1994) Oncogene 9:2145-2152).

The experimental data presented in the Examples show that PMEPA1 negatively regulates cancer cell growth. Loss of such function favors tumorigenesis or progression of existing disease. Thus, PMEPA1 may suppress tumorigenesis or cancer progression by interacting with WW domain-containing molecules. The homology of PMEPA1 to the NEDD4-binding protein and the ability of PMEPA1 to bind NEDD4 indicates that PMEPA1 may regulate protein turnover via ubiquitinylation and proteasome pathways in the cell. This mechanism is, of course, merely proposed. Moreover, it is not the only mechanism by which PMEPA1 may exert its function. The present invention is not limited to any particular mechanism of PMEPA1 activity.

In one embodiment, a polypeptide of the invention comprises an amino acid sequence as set out in SEQ ID NO:3. In another embodiment, the polypeptide comprises an amino acid sequence substantially as set out in SEQ ID NO:3. In yet another embodiment, the polypeptide comprises an amino acid sequence that is at least 80%, 90%, 95%, 96%, 97%, 98%, 99%, OR 99.9% identical to SEQ ID NO:3, and preferably the polypeptide inhibits prostate cancer cell growth, as demonstrated, for example, in a colony-forming assay, such as the one described in Example 12. Inhibiting cell growth refers to a decrease in cell growth in the presence of a PMEPA1 polypeptide, relative to the cell growth in the absence of the PMEPA1 polypeptide. Alternatively, if a cell has a basal level of PMEPA1 polypeptide expression, it refers to a decrease in cell growth in the presence of increased levels of PMEPA1 polypeptide, relative to cell growth in the presence of the basal level of PMEPA1 polypeptide. Cell growth can be measured using conventional assays, such as the colony-forming assay described in the examples. As discussed in further detail below, these polypeptides may be produced by recombinant DNA techniques. Percent identity may be determined by visual inspection and mathematical calculation. Alternatively, the percent identity of two protein sequences can be determined by comparing sequence information using the GAP computer program, based on the algorithm of (Needleman and Wunsch, *J. Mol. Bio.*, 48:443 (1970)) and available from the University of Wisconsin Genetics Computer Group (UWGCG). The preferred default parameters for the GAP program include: (1) a scoring matrix, blosum62, as described by (Henikoff and Henikoff *Proc. Natl. Acad. Sci. USA*, 89:10915 (1992)); (2) a gap weight of 12; (3) a gap length weight of 4; and (4) no penalty for end gaps. Other programs used by one skilled in the art of sequence comparison may also be used.

The polypeptides of the invention may be membrane bound or they may be secreted and thus soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

In one embodiment, the soluble polypeptides and fragments thereof comprise all or part of the extracellular domain, but lack the transmembrane region that would cause retention of the polypeptide on a cell membrane. A soluble polypeptide may include the cytoplasmic domain, or a portion thereof, as long as the polypeptide is secreted from the cell in which it is produced.

In general, the use of soluble forms is advantageous for certain applications. Purification of the polypeptides from recombinant host cells is facilitated, since the soluble polypeptides are secreted from the cells. Further, soluble polypeptides are generally more suitable for intravenous administration.

The invention also provides polypeptides and fragments of the extracellular domain that retain a desired biological activity. Such a fragment may be a soluble polypeptide, as described above.

Also provided herein are polypeptide fragments comprising at least 20, or at least 30, contiguous amino acids of the sequence of SEQ ID NO:3. Fragments derived from the cytoplasmic domain find use in studies of signal transduction, and in regulating cellular processes associated with transduction of biological signals. Polypeptide fragments also may be employed as immunogens, in generating antibodies.

Variants

Naturally occurring variants as well as derived variants of the polypeptides and fragments are provided herein.

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1-5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in (Hopp et al., *Bio/Technology*, 6:1204 (1988)). One such peptide is the FLAG® peptide, Asp-Tyr-Lys-Asp-Asp-Asp-Asp-Lys, (SEQ ID NO:4) which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Among the variant polypeptides provided herein are variants of native polypeptides that retain one or more activities associated with a full-length, wild-type, PMEPA1 protein. As one example, such variants or analogs that have the desired immunogenicity or antigenicity can be used, for example, in immunoassays, for immunization, for inhibition of PMEPA1 activity, etc. Variants or analogs that retain, or alternatively lack or inhibit, a desired PMEPA1 property of interest can be used as inducers, or inhibitors, respectively, of such property and its physiological correlates. These PMEPA1 properties include, but are not limited to, binding to a WW domain-containing protein or other PMEPA1 binding partner, inhibiting cancer cell proliferation, inhibiting the expression of an androgen receptor, and modulating the expression of a gene whose transcription is regulated by the androgen receptor. Binding affinity can be measured by conventional procedures, e.g., as described in U.S. Pat. No. 5,512,457 and as set forth below. Variants or analogs of PMEPA1 can be tested for the desired activity by procedures known in the art, including but not limited to, the assays described in the Examples.

In one embodiment, the PMEPA1 variants contain at least one mutation and/or deletion in the at least one of the PY motifs of PMEPA1. These variants can be used, for example, in the treatment of hypoproliferative disorders. In addition, these variants can be used as immunogens to generate antibodies.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Further, a given preparation may include multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, similar DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in proteins include those described in U.S. Pat. Nos. 5,071,972 and EP 276,846, hereby incorporated by reference.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Production of Polypeptides and Fragments thereof

Expression, isolation and purification of the polypeptides and fragments of the invention may be accomplished by any suitable technique, including but not limited to the following:

Expression Systems

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in (Pouwels et al. *Cloning Vectors: A Laboratory Manual*, Elsevier, N.Y., (1985)). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable-marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615 (1978); and (Goeddel et al., *Nature* 281:544 (1979)), tryptophan (trp) promoter system (Goeddel et al., *Nucl. Acids Res.* 8:4057 (1980); and EP-A-36776) and tac promoter (Maniatis, *Molecular Cloning: A Laboratory Manual*, Cold Spring Harbor Laboratory, p. 412 (1982)). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Yeast Systems

Alternatively, the polypeptides may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073 (1980)) or other glycolytic enzymes (Hess et al., *J. Adv. Enzyme Reg.* 7:149 (1968)); and (Holland et al., *Biochem.* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in (Hitzeman, EPA-73,657). Another alternative is the glucose-repressible ADH2 promoter described by (Russell et al., *J. Biol. Chem.* 258:2674 (1982)) and (Beier et al., *Nature* 300:724 (1982)). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., (Kurjan et al., *Cell* 30:933 (1982)) and (Bitter et al., *Proc. Natl. Acad. Sci. USA* 81:5330 (1984)). Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by (Hinnen et al., *Proc. Natl. Acad. Sci. USA* 75:1929 (1978)). The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

Mammalian or insect host cell culture systems also may be employed to express recombinant polypeptides. Bacculovirus systems for production of heterologous proteins in insect cells are reviewed by (Luckow and Summers, *Bio/Technology*, 6:47 (1988)). Established cell lines of mammalian origin also may be employed. Examples of suitable mammalian host cell lines include the COS-7 line of monkey kidney cells (ATCC CRL 1651) (Gluzman et al., *Cell* 23:175 (1981)), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by (McMahan et al., *EMBO J.*, 10: 2821 (1991)).

Established methods for introducing DNA into mammalian cells have been described (Kaufman, R. J., *Large Scale Mammalian Cell Culture*, pp. 15-69 (1990)). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413-7417 (1987)). In addition, electroporation can be used to transfect mammalian cells using conventional procedures, such as those in (Sambrook et al., *Molecular Cloning: A Laboratory Manual*, 2 ed. Vol. 1-3, Cold Spring Harbor Laboratory Press (1989)). Selection of stable transformants can be performed using methods known in the art, such as, for example, resistance to cytotoxic drugs. (Kaufman et al., *Meth. in Enzymology* 185:487-511 (1990)), describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220 (1980)). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113 (1978)); (Kaufman, *Meth. in Enzymology* (1990)). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, pp. 529-534 and PCT Application WO 97/25420 (1997)) and the tripartite leader (TPL) and VA gene RNAs from Adenovirus 2 (Gingeras et al., *J. Biol. Chem.* 257:13475-13491 (1982)). The internal ribosome entry site (IRES) sequences of viral origin allows dicistronic mRNAs to be translated efficiently (Oh and Sarnow, *Current Opinion in Genetics and Development* 3:295-300 (1993)); (Ramesh et al., *Nucleic Acids Research* 24:2697-2700 (1996)). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology* (1990)). Exemplary expression vectors that employ dicistronic mRNAs are pTR-DC/GFP described by (Mosser et al., *Biotechniques* 22:150-161 (1997)), and p2A5I described by (Morris et al., *Animal Cell Technology*, pp. 529-534 (1997)).

A useful high expression vector, pCAVNOT, has been described by (Mosley et al., *Cell* 59:335-348 (1989)). Other expression vectors for use in mammalian host cells can be constructed as disclosed by (Okayama and Berg, *Mol. Cell. Biol.* 3:280 (1983)). A useful system for stable high level expression of mammalian cDNAs in C127 murine mammary epithelial cells can be constructed substantially as described by (Cosman et al., *Mol. Immunol.* 23:935 (1986)). A useful high expression vector, PMLSV N1/N4, described by (Cosman et al., *Nature* 312:768 (1984)), has been deposited as ATCC 39890. Additional useful mammalian expression vectors are described in EP-A-0367566, and in WO 91/18982, incorporated by reference herein. In yet another alternative, the vectors can be derived from retroviruses.

Another useful expression vector, pFLAG®, can be used. FLAG® technology is centered on the fusion of a low molecular weight (1 kD), hydrophilic, FLAG® marker peptide to the N-terminus of a recombinant protein expressed by PFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Purification

The invention also includes methods of isolating and purifying the polypeptides and fragments thereof.

Isolation and Purification

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See (Berenson, et al. *J. Cell. Biochem.*, 10D:239 (1986)). Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Production of Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9, Garland Publishing Inc., 2nd ed. (1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14, Garland Publishing Inc., 2nd ed. (1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, (Kennet et al., *Monoclonal Antibodies, Hybridomas: A New Dimension in Biological Analyses*, eds., Plenum Press, New York (1980); and Harlow and Land, *Antibodies: A Laboratory Manual*, eds., Cold Spring Harbor Laboratory Press, Cold Spring Harbor, N.Y., (1988)).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in (Riechmann et al., *Nature* 332: 323 (1988), Liu et al., *PNAS* 84:3439 (1987), Larrick et al., *Bio/Technology* 7:934 (1989), and Winter and Harris, *TIPS* 14:139 (May 1993)). Procedures to generate antibodies transgenically can be found in GB 2,272,440, U.S. Pat. Nos. 5,569, 825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

The following examples further illustrate preferred aspects of the invention.

EXAMPLE 1

Cell Culture and Androgen Stimulation

LNCaP cells (American Type Culture Collection, Rockville, Md.) were used for SAGE analysis of ARGs. LNCaP cells were maintained in RPMI 1640 (Life Technologies, Inc., Gaithersburg, Md.) supplemented with 10% fetal bovine serum (FBS, Life Technologies, Inc., Gaithersburg, Md.) and experiments were performed on cells between passages 20 and 30. For the studies of androgen regulation, charcoal/dextran stripped androgen-free FBS (cFBS, Gemini Bio-Products, Inc., Calabasas, Calif.) was used. LNCAP cells were cultured first in RPMI 1640 with 10% cFBS for 5 days and then stimulated with 10-8 M of non-metabolizable androgen analog, R1881 (DUPONT, Boston, Mass.) for 24 hours. LNCaP cells identically treated but without R1881 treatment served as control. Cells were harvested at indicated time and polyA+ RNA was double-selected with Fast Track kit (Invitrogene). The quality of polyA+ was checked by Northern hybridization analysis.

EXAMPLE 2

SAGE Analysis

Two SAGE libraries (library LNCaP-C and library LNCaP-T) were generated according to the procedure described previously Velculescu et al. (30). Briefly, biotinylated oligo dT primed cDNA was prepared from five micrograms of polyA+ RNA from R1881 treated and control LNCaP cells and biotinylated cDNA was captured on strepravidin coated magnetic beads (Dynal Corporation, Mich.). cDNA bound to the magnetic beads were digested by NlaIII followed by ligation to synthetic linkers containing a site for anchoring enzyme, NlaIII and a site for tagging enzyme BsmF1. The restriction digestion of ligated products with BsmF1 resulted in the capture of 10-11 bp sequences termed as "tags" representing signature sequence of unique cDNAs. A multi-step strategy combining ligation, PCR, enzymatic digestion and gel purification yielded two tags linked together termed as "ditags." Ditags were concatamerized, purified and cloned in plasmid pZero cloning vector (Invitrogen, Calif.). The clones containing concatamers were screened by PCR and sequenced. The sequence and the occurrence of each of the SAGE tags was determined using the SAGE software kindly provided by Dr. Kenneth W. Kinzler (Johns Hopkins University School of Medicine, Baltimore, Md.). All the SAGE tags sequences were analyzed for identity to DNA sequence in GenBank (National Center for Biotechnology Information, Bethesda, Md., USA). The relative abundance of each transcript was determined by dividing the number of individual tags by total tags in the library. The copy number of each gene was calculated assuming there are approximately 300,000 transcripts in a cell (Zhang et al., 1997). The differentially expressed SAGE tags were determined by comparing the frequency of occurrence of individual tags in the two libraries obtained from the control (library LNCaP-C) and R1881 treated LNCaP cells (library LNCaP-T). The results were analyzed with t test, and $p<0.05$ was considered as a statistically significant difference for a specific tag between these two libraries.

EXAMPLE 3

Kinetics of Androgen Regulation ARGs Defined by SAGE Analysis

LNCaP cells were cultured in RPMI 1640 with 10% cFBS for 5 days, then stimulated with R1881 at 10-10, 10-8, and 10-6 M for 1, 3, 12, 24, 72, 120, 168, and 216 hours. LNCaP cells identically treated but without R1881 served as control. The cells were harvested at indicated time and polyA+ RNA was prepared as described as above. The polyA+ RNA was fractionated (2 μg/lane) by running through 1% formaldehyde-agarose gel and transferred to nylon membrane. The cDNA probes of several ARGs were labeled with 32P-dCTP by random priming (Stratagene Cloning Systems, La Jolla, Calif.). The nylon membranes were prehybridized for 2 hrs in hybridization buffer (10 mM Tris-HCl, pH 7.5, 10% Dextran sulfate, 40% Formamide, 5×SSC, 5× Denhardt's solution and 0.25 mg/ml salmon sperm DNA) and hybridized to the 32P labeled probes (1×106 cpm/ml) in the same buffer at 40° C. for 12-16 hrs. Blots were washed twice in 2×SSC/0.1% SDS for 20 min at room temperature followed by two high-stringency wash with 0.1×SSC/0.1% SDS at 50° C. for 20 min. Nylon membranes were exposed to X-ray film for autoradiography.

EXAMPLE 4

ARGs Expression Pattern in Cwr22 Model.

CWR22 (androgen dependent) and CWR22R (androgen relapsed) tumor specimens were kindly provided by Dr. Thomas Pretlow (Case Western Reserve University School of Medicine). The tissue samples were homogenized and polyA+ RNA was extracted with Fast Track kit (Invitrogen) following manufacture's protocol. Northern blots were prepared as described in Example 3 and were hybridized with $^{32}$P labeled probes of the cDNA of interest.

Analysis of SAGE tag libraries from R1881 treated LNCAP cells. LNCaP cells were maintained in androgen deprived growth media for five days and were treated with synthetic androgen R1881 (10 nm) for 24 hours. Since a goal of the inventors was to identify androgen signaling read-out transcripts, we chose conditions of R1881 treatment of LNCAP cells showing a robust and stable transcriptional induction of well-characterized prostate-specific androgen regulated genes, prostate-specific antigen (PSA) and NKX3.1 genes. A total of 90,236 tags were derived from the two SAGE libraries. Of 90,236 tags, 6,757 tags corresponded to linker sequences, and were excluded from further analysis. The remaining 83,489 tags represented a total of 23,448 known genes or ESTs and 1,655 tags did not show any match in the GeneBank data base. The relative abundance of the SAGE tags varied between 0.0011% and 1.7%. Assuming that there are 18,000 transcripts per cell type and there are about 83,489 anticipated total transcripts, the estimated abundance of transcripts will be 0.2-308 copies per cell. This calculation indicated that single copy genes had high chance to be recognized by SAGE analysis in this study. The distribution of transcripts by copy number suggests that the majority (above 90%) of the genes in our analysis are expressed at 1 or 2 copies level/cell. A total of 46,186 and 45,309 tags were analyzed in the control (C) and R1881 (T) groups respectively. Unique SAGE tags corresponding to known genes, expressed sequence tags (ESTs) and novel transcripts were 15,593 and 15,920 in the control and androgen treated groups respectively. About 94% of the unique SAGE tags in each group showed a match to a sequence in the gene bank and 6% SAGE tags represented novel transcripts. The most abundant SAGE tags in both control and androgen treated LNCaP cells represented proteins involved in cellular translation machinery e.g., ribosomal proteins, translation regulators, mitochondrial proteins involved in bio-energetic pathways.

EXAMPLE 5

Analysis of the ARGs Defined by SAGE Tags

Of about 15,000 unique tags a total of 136 SAGE tags were significantly up-regulated in response to R1881 whereas 215 SAGE tags were significantly down-regulated (p<0.05). It is important to note that of 15,000 expressed sequences only 1.5% were androgen responsive suggesting that expression of only a small subset of genes are regulated by androgen under our experimental conditions. The ARGs identified by the inventors are anticipated to represent a hierarchy, where a fraction of ARGs are directly regulated by androgens and others represent the consequence of the activation of direct down-stream target genes of the AR. Comparison of SAGE tags between control and R1881 also revealed that 74 SAGE tags were significantly up-regulated (p<0.05) by four-fold and 120 SAGE tags were significantly (p<0.05) down-regulated. Two SAGE tags corresponding to the PSA gene sequence exhibited highest induction (16 fold) between androgen treated (T) and control (C) groups. Another prostate specific androgen regulated gene, NKX3.1 was among significantly up-regulated ARGs (8 fold). Prostate specific membrane antigen (PSMA) and Clusterin known to be down-regulated by androgens were among the SAGE tags exhibiting decreased expression in response to androgen (PSMA, 4 fold; Clusterin, fold). Therefore, identification of well characterized up-regulated and down-regulated ARGs defined by SAGE tags validates the use of LNCaP experimental model for defining physiologically relevant ARGs in the context of prostatic epithelial cells. It is important to note that about 90% of up-regulated ARGs and 98% of the down-regulated ARGs defined by our SAGE analysis were not known to be androgen- regulated before.

EXAMPLE 6

Identification of Prostate Specific/Abundant Genes

LNCaP C/T-SAGE tag libraries were compared to a bank of 35 SAGE tag libraries (available from the SAGE website provided by the National Center for Biotechnology Information containing 1.5 million tags from diverse tissues and cell types. Our analysis revealed that known prostate specific genes e.g., PSA and NKX3.1 were found only in LNCaP SAGE tag libraries (this report and one LNCaP SAGE library present in the SAGE tag bank). We have extended this observation to the other candidate genes and transcripts. On the basis of abundant/unique expression of the SAGE tag defined transcripts in LNCaP SAGE tag libraries relative to other libraries, we have now identified several candidate genes and ESTs whose expression are potentially prostate specific or restricted (Table 4). The utility of such prostate-specific genes includes: (a) the diagnosis and prognosis of CaP (b) tissue specific targeting of therapeutic genes (c) candidates for immunotherapy and (d) defining prostate specific biologic functions.

Genes with defined functions showing at least five fold up or down-regulation (p<0.05) were broadly classified on the basis of their biochemical function, since our results of Northern analysis of representative SAGE derived ARGs at 5-fold difference showed most reproducible results. Table 9, presented at the end of this specification immediately preceding the "References" section, represents the quantitative expression profiles of a panel of functionally defined ARGs in the context of LNCaP prostate cancer cells. ARGs in the transcription factor category include proteins involved in the general transcription machinery e.g., KAP1/TIF β, CHD4 and SMRT (Douarin et al., 1998; Xu et al., 1999) have been shown to participate in transcriptional repression. The mitochondrial transcription factor 1 (mtTF1) was induced by 8 fold in response to R1881. A recent report describes that another member of the nuclear receptor superfamily, the thyroid hormone receptor, also up-regulates a mitochondrial transcription factor expression through a specific co-activator, PGC-1 (Wu et al., 1999). As shown in Table 9 a thyroid hormone receptor related gene, ear-2 (Miyajima et al., 1998) was also upregulated by R1881. It is striking to note that expression of four [NKX3.1 (He et al., 1997), HOX B13 (Sreenath et al., 1999), mtTF1 and PDEF (Oettgen et al., 2000)] of the eight transcription regulators listed in Table 9 appear to be prostate tissue abundant/specific based on published reports as well as our analysis described above.

ARGs also include a number of proteins involved in cellular energy metabolism and it is possible that some of these enzymes may be transcriptionally regulated by mtTF1. Components of enzymes involved in oxidative decaboxylation: dihydrolipoamide succinyl transferase (Patel et al., 1995), puruvate dehydrogenase E-1 subunit (Ho et al., 1989), and the electron tansport chain: NADH dehydrogenase 1 beta subcomplex 10 (Ton et al., 1997) were upregulated by androgen. VDAC-2 (Blachly-Dyson et al., 1994), a member of small pore forming proteins of the outer mitochondrial membrane and which may regulate the transport of small metabolites necessary for oxidative-phosphorylation, was also up regulated by androgen. Diazepam binding protein (DBI), a previous reported ARG (Swinnen et al., 1996), known to be associated with the VDAC complex and implicated in a multitude of functions including modulation of pheripheral benzodiaepine receptor, acyl-CoA metabolism and mitochondrial steroidogenesis (Knudsen et al., 1993) were also induced by androgen in our study. A thioredoxin like protein (Miranda-Vizuete et al., 1998) which may function in modulating the cellular redox state was down regulated by androgen. In general, it appears that modulation of ARGs involved in regulating cellular redox status and energy metabolism may effect reactive oxygen species concentrations.

A number of cell proliferation associated proteins regulating cell cycle, signal transduction and cellular protein trafficking were upregulated by androgen, further supporting the role of androgens in survival and growth of prostatic epithelial cells. Androgen regulation of two proteins: XRCC2 (Cartwright et al., 1998) and RPA3 (Umbricht et al., 1993) involved in DNA repair and recombination is a novel and interesting finding. Induction of these genes may represent a response to DNA damage due to androgen mediated pro-oxidant shift, or these genes simply represent components of genomic surveillance mechanisms stimulated by cell proliferation. The androgen induction of a p53 inducible gene, PIG 8 (Umbricht et al., 1997), is another intriguing finding as the mouse homolog of this gene, ei24 (Gu et al., 2000), is induced by etoposide known to generate reactive oxygen species. In addition, components of protein kinases modulated by adenyl cyclase, guanyl cyclase and calmodulin involved in various cellular signal transduction stimuli were also regulated by androgen.

Gene expression modulations in RNA processing and translation components is consistent with increased protein synthesis expected in cells that are switched to a highly proliferative state. Of note is nucleolin, one of the highly androgen induced genes (12 fold) which is an abundant nucleolar protein associating with cell proliferation and plays a direct role in the biogenesis, processing and transport of ribosomes to the cytoplasm (Srivastava and Pollard, 1999). Another androgen up-regulated gene, exportin, a component of the nuclear pore, may be involved in the shuttling of nucleolin. Androgen regulation of SiahBP1 (Page-McCaw et al., 1999), GRSF-1 (Qian and Wilusz, 1994) and PAIP1 (Craig et al., 1998) suggests a role of androgen signaling in the processing of newly transcribed RNAs. Two splicesosomal genes, snRNP-G and snRNP-E coding for small ribo-nucleoproteins were down-regulated by androgen. The unr-interacting protein, UNRIP (Hunt et al., 1999) which is involved in the direct ribosome entry of many viral and some cellular mRNAs into the translational pathway, was the most down-regulated gene in response to androgen.

Quantitative evaluation of gene expression profiles by SAGE approach have defined yeast transcriptome (Velculescu et al., 1997) and have identified critical genes in biochemical pathways regulated by p53 (Polyak et al., 1997), x-irradiation (Hermeking et al., 1997) and the APC gene (Korinek et al., 1997). Potential tumor biomarkers in colon (Zhang et al., 1997), lung (Hibi et al., 1998), and breast (Nacht et al., 1999) cancers and genes regulated by other cellular stimuli (Waard et al., 1999; Berg et al., 1999) have also been identified by SAGE. SAGE technology has enabled us to develop the first quantitative database of androgen regulated transcripts. Comparison of our SAGE tag libraries to the SAGE TagBank has also revealed a number of new candidate genes and ESTs whose expression is potentially abundant or specific to the prostate. We have also identified a large number of transcripts not previously defined as ARGs.

A great majority of functionally defined genes that were modulated by androgen in our experimental system appear to promote cell proliferation, cell survival, gain of energy and increased oxidative reactions shift in the cells. However, a substantial fraction of these ARGs appears to be androgen specific since they do not exhibit appreciable change in their expression in other studies examining cell proliferation associated genes (Iyer et al., 1999, Science, 283:83-87, supplemented by the website provided at Stanford University) or estrogen regulated genes in MCF7 cells (Charpentier et al., 2000). The interesting experimental observation of Ripple et al. (Ripple et al., 1997) showing a prooxidant-antioxidant shift induced by androgen in prostate cancer cells is supported by our identification of specific ARGs (upregulation of enzymes involved in oxidative reactions, electron transport chain and lipid metabolism in mitochondria and down regulation of thioredoxin like protein) that may be involved in the induction of oxidative stress by androgen.

EXAMPLE 7

Characterization of the Androgen-Regulated Gene PMEPA1 cDNA library screening and Sequencing of cDNA clone. One of the SAGE tags (14 bp) showing the highest induction by androgen (29-fold) exhibited homology to an EST in the GenBank EST database. PCR primers (5'GGCAGAACACTCCGCGCTTCTTAG3' (SEQ ID NO. 5) and 5'CAAGCTCTCTTAGCTTGTGCATTC3' (SEQ ID NO. 6)) were designed based on the EST sequence (accession number AA310984). RT-PCR was performed using RNA from R1881 treated LNCaP cells and the co-identity of the PCR product to the EST was confirmed by DNA sequencing. Using the PCR product as probe, the normal prostate cDNA library was screened through the service provided by Genome Systems (St. Louis, Mo.). An isolated clone, GS 22381 was sequenced using the 310 Genetic Analyzer (PE Applied Biosystems, Foster Calif.) and 750 bp of DNA sequence was defined, which included ⅔ of the coding region of PMEPA1. A GenBank search with PMEPA1 cDNA sequence revealed one EST clone (accession number AA088767) homologous to the 5' region of the PMEPA1 sequence. PCR primers were designed using the EST clone (5' primer) and PMEPA1 (3' primer) sequence. cDNA from LNCaP cells was PCR amplified and the PCR product was sequenced using the PCR primers. The sequences were verified using at least two different primers. A contiguous sequence of 1,141 bp was generated by these methods.

Kinetics of Androgen Regulation of PMEPA1 Expression in LNCaP Cells.

LNCaP cells (American Type Culture Collection, ATCC, Rockville Md.) were maintained in RPMI 1640 media (Life Technologies, Inc., Gaithersburg, Md.) supplemented with 10% fetal bovine serum (FBS, Life Technologies, Inc., Gaithersburg, Md.) and experiments were performed on cells cultured between passages 20 and 30. For the studies of androgen regulation, charcoal/dextran stripped androgen-free FBS (cFBS, Gemini Bio-Products, Inc., Calabasas, Calif.) was used. LNCaP cells were cultured first in RPMI 1640 with 10% cFBS for 5 days, and then stimulated with R1881 (DUPONT, Boston, Mass.) at $10^{-10}$ M and $10^{-8}$ M for 3, 6, 12 and 24 hours. LNCaP cells identically treated but without R1881 served as control. To study the effects of androgen withdrawal on PMEPA1 gene expression, LNCaP cells were cultured in RPMI 1640 with 10% cFBS for 24, 72 and 96 hours. Poly $A^+$ RNA samples derived from cells treated with or without R1881 were extracted at indicated time points with a Fast Track mRNA extraction kit (Invitrogen, Carlsbad, Calif.) following the manufacturer's protocol. Poly $A^+$ RNA specimens (2 μg/lane) were electrophoresed in a 1% formaldehyde-agarose gel and transferred to a nylon membrane. Two PMEPA1 probes used for Northern blots analysis were (a) cDNA probe spanning nucleotides 3-437 of PMEPA1 cDNA sequence (See Table 1) and (b) 71-mer oligonucleotide between nucleotides 971 to 1,041 of PMEPA1 cDNA sequence (See Table 1).

The cDNA probe was generated by RT-PCR with primers 5'CTTGGGTTCGGGTGAAAGCGCC 3' (SEQ ID NO. 7) (sense) and 5'GGTGGGTGGCAGGTCGATCTCG 3' (SEQ ID NO. 8) (antisense). PMEPA1 oligonucleotide and cDNA probes and glyceraldehyde phosphate dehydrogenase gene (GAPDH) cDNA probe were labeled with $^{32}$P-dCTP using 3' end tailing for oligonucleotides (Promega, Madison, Wis.) and random priming for cDNA (Stratagene, La Jolla, Calif.). The nylon membranes were treated with hybridization buffer (10 mM Tris-HCl, pH 7.5, 10% Dextran sulfate, 40% Formamide, 5×SSC, 5× Denhardt's solution and 0.25 mg/ml salmon sperm DNA) for two hours followed by hybridization in the same buffer containing the $^{32}$P labeled probes (1×10$^6$ cpm/ml) for 12-16 hrs at 40° C. Blots were washed twice in 2×SSC/0.1% SDS for 20 min at room temperature followed by two high-stringency washes with 0.1×SSC/0.1% SDS at 58° C. for 20 min. Nylon membranes were exposed to X-ray film for autoradiography. The bands on films were then quantified with NIH-Image processing software.

PMEPA1 expression analysis in CWR22 tumors. CWR22 is an androgen-dependent, serially transplantable nude mouse xenograft derived from a primary human prostate cancer. Transplanted CWR22 tumors are positive for AR and the growth of CWR22 is androgen dependent. CWR22 tumors regress initially upon castration followed by a relapse. The recurrent CWR22 tumors (CWR22R) express AR, but the growth of these tumors become androgen-independent (Gregory et al., 1998; Nagabhushan et al., 1996). One CWR22 and four CWR22R tumor specimens were kindly provided by Dr. Thomas Pretlow's laboratory (Case Western Reserve University School of Medicine). Tumor tissues were homogenized and polyA$^+$ RNA were extracted as above. PolyA$^+$ RNA blots were made and hybridized as described above.

PMEPA1 expression analysis in multiple human tissues and cell lines. Multiple Tissue Northern blots containing mRNA samples from 23 human tissues and Master Dot blots containing mRNA samples from 50 different human tissues were purchased from ClonTech (Palo Alto, Calif.). The blots were hybridized with PMEPA1 cDNA and oligo probes, as described above. The expression of PMEPA1 in normal prostate epithelial cells (Clonetics, San Diego, Calif.), prostate cancer cells PC3 (ATCC) and LNCaP cells and breast cancer cells MCF7 (ATCC) was also analyzed by northern blot.

In situ hybridization of PMEPA1 in prostate tissues. A 430 bp PCR fragment (PCR sense primer: 5'CCTTCGC-CCAGCGGGAGCGC 3', (SEQ ID NO. 9) PCR antisense primer 5'CAAGCTCTCTTAGCTTGTGCATTC3' (SEQ ID NO. 10) was amplified from cDNA of LNCaP cells treated by R1881 and was cloned into a PCR-blunt II-TOPO vector (Invitrogen, Carlsbad, Calif.). Digoxigenin labeled antisense and sense riboprobes were synthesized using an in vitro RNA transcription kit (Boehringer Mannheim, GMbH, Germany) and a linearized plasmid with PMEPA1 gene fragment as templates. Frozen normal and malignant prostate tissues were fixed in 4% paraformaldehyde for 30 min. Prehybridization and hybridization were performed at 55° C. After hybridization, slides were sequentially washed with 2×SSC at room temperature for 30 min, 2×SSC at 58° C. for 1 hr and 0.1×SSC at 58° C. for 1 hr. Antibody against digoxygenin was used to detect the signal and NBT/BCIP was used as substrate for color development (Boehringer Mannheim, GMbH, Germany). The slides were evaluated under an Olympus BX-60 microscope.

Full-Length PMEPA1 Coding Sequence and Chromosomal Localization.

Analysis of the 1,141 bp PMEPA1 cDNA sequence (SEQ ID NO. 1) revealed an open reading frame of 759 bp nucleotides (SEQ ID NO. 2) encoding a 252 amino acid protein (SEQ ID NO. 3) with a predicted molecular mass of 27.8 kDa, as set forth below in Table 1.

TABLE 1

```
TCCTTGGGTTCGGGTGAAAGCGCCTGGGGGTTCGTGGCCATGATCCCCGAGCTGCTGGAGAACTGAAGGCGGACAGTCTCCTGCGAAAC          90

AGGCAATGGCGGAGCTGGAGTTTGTTCAGATCATCATCATCGTGGTGGTGATGATGGTGATGGTGGTGGTGATCACGTGCCTGCTGAGCC         180
     M  A  E  L  E  F  V  Q  I  I  I  I  V  V  V  M  M  V  M  V  V  V  I  T  C  L  L  S           28

ACTACAAGCTGTCTGCACGGTCCTTCATCAGCCGGCACAGCCAGGGGCGGAGGAGAGAAGATGCCCTGTCCTCAGAAGGATGCCTGTGGC         270
 H  Y  K  L  S  A  R  S  F  I  S  R  H  S  Q  G  R  R  R  E  D  A  L  S  S  E  G  C  L  W        58

CCTCGGAGAGCACAGTGTCAGGCAACGGAATCCCAGAGCCGCAGGTCTACGCCCCGCCTCGGCCCACCGACCGCCTGGCCGTGCCGCCCT        360
 P  S  E  S  T  V  S  G  N  G  I  P  E  P  Q  V  Y  A  P  P  R  P  T  D  R  L  A  V  P  P       88

TCGCCCAGCGGGAGCGCTTCCACCGCTTCCAGCCCACCTATCCGTACCTGCAGCACGAGATCGACCTGCCACCCACCATCTCGCTGTCAG        450
 F  A  Q  R  E  R  F  H  R  F  Q  P  T  Y  P  Y  L  Q  H  E  I  D  L  P  P  T  I  S  L  S      118

ACGGGGAGGAGCCCCCACCCTACCAGGGCCCCTGCACCCTCCAGCTTCGGGACCCCGAGCAGCAGCTGGAACTGAACCGGGAGTCGGTGC        540
 D  G  E  E  P  P  P  Y  Q  G  P  C  T  L  Q  L  R  D  P  E  Q  Q  L  E  L  N  R  E  S  V     148

GCGCACCCCCAAACAGAACCATCTTCGACAGTGACCTGATGGATAGTGCCAGGCTGGGCGGCCCCTGCCCCCCCAGCAGTAACTCGGGCA        630
 R  A  P  P  N  R  T  I  F  D  S  D  L  M  D  S  A  R  L  G  G  P  C  P  P  S  S  N  S  G    178

TCAGCGCCACGTGCTACGGCAGCGGCGGGCGCATGGAGGGGCCGCCGCCCACCTACAGCGAGGTCATCGGCCACTACCCGGGGTCCTCCT        720
 I  S  A  T  C  Y  G  S  G  G  R  M  E  G  P  P  P  T  Y  S  E  V  I  G  H  Y  P  G  S  S    208

TCCAGCACCAGCAGAGCAGTGGGCCGCCCTCCTTGCTGGAGGGGACCCGGCTCCACCACACACATCGCGCCCTAGAGAGCGCAGCCA         810
 F  Q  H  Q  Q  S  S  G  P  P  S  L  L  E  G  T  R  L  H  H  T  H  I  A  P  L  E  S  A  A    238

TCTGGAGCAAAGAGAAGGATAAACAGAAAGGACACCCTCTCTAGGGTCCCCAGGGGGGCCGGGCTGGGGCTGCGTAGGTGAAAAGGCAGA         900
 I  W  S  K  E  K  D  K  Q  K  G  H  P  L  *  (SEQ ID NO. 3)                                    252

ACACTCCGCGCTTCTTAGAAGAGGAGTGAGAGGAAGGCGGGGGGCGCAGCAACGCATCGTGTGGCCCTCCCCTCCCACCTCCCTGTGTAT         990

AAATATTTACATGTGATGTCTGGTCTGAATGCACAAGCTAAGAGAGCTTGCAAAAAAAAAAAGAAAAAAGAAAAAAAAAAACCACGTTTC        1080

TTTGTTGAGCTGTGTCTTGAAGGCAAAAGAAAAAAAATTTCTACAGTAAAAAAAAAAAAAA 1141 (SEQ ID NO.1)
```

As indicated above, Table 1 represents the nucleotide and predicted amino acid sequence of PMEPA1 (GenBank accession No. AF224278). The potential initiation methionine codon and the translation stop codons are indicated in bold. The transmembrane domain is underlined. The locations of the intron/exon boundaries are shown with arrows, which were determined by comparison of the PMEPA1 cDNA sequence to the publicly available sequences of human clones RP5-1059L7 and 718J7 (GenBank accession No. AL121913 and AL035541).

A GenBank search revealed a sequence match of PMEPA1 cDNA to two genomic clones, RP5-1059L7 (accession number AL121913 in the GenBank/htgc database) and 718J7 (accession number AL035541 in the GenBank/nr database). These two clones mapped to Chromosome 20q13.2-13.33 and Chromosome 20q13.31-13.33. This information provided evidence that PMEPA1 is located on chromosome 20q13.

Figure 1:
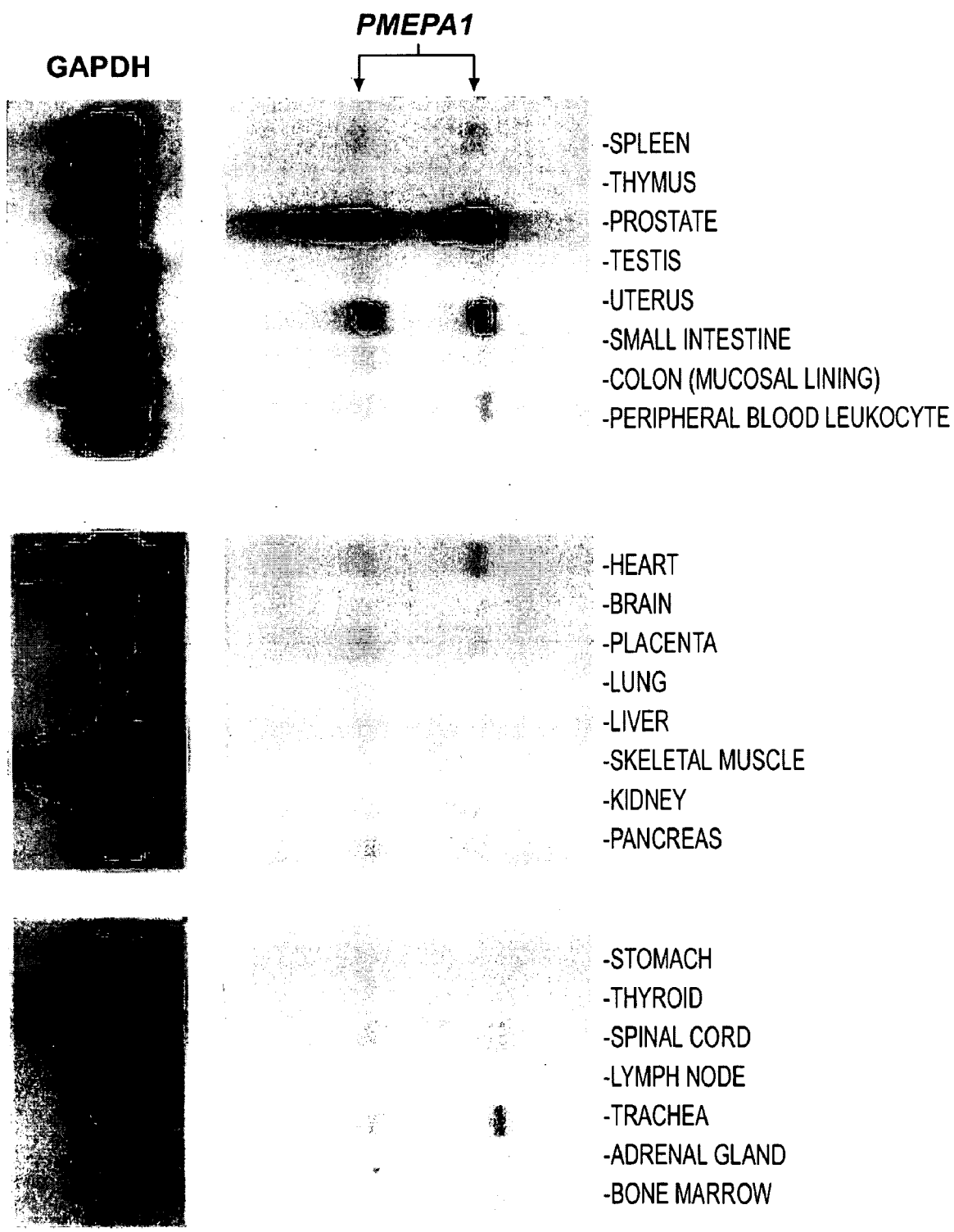
FIG. 1 is a Northern blot showing that PMEPA1 is expressed at high levels in prostate tissue. Multiple tissue northern blots were hybridized with PMEPA1 and GAPDH probes. The arrows indicate the two variants of the PMEPA1 transcript.

The intron/exon junctions of PMEPA1 gene were determined based on the comparison of the sequences of PMEPA1 and the two genomic clones. A protein motif search using ProfileScan (available from the Internet site provided by EMBnet) indicated the existence of a type Ib transmembrane domain between amino acid residues 9 to 25 of the PMEPA1 sequence. Another GenBank search further revealed that the PMEPA1 showed homology (67% sequence identity and 70% positives at protein level) to a recently described novel cDNA located on chromosome 18 (accession number NM_004338) (Yoshikawa et al., 1998), as set forth below in Table 2. In addition to the sequence similarity, PMEPA1 also shares other features with C18orf1, e.g., similar size of the predicted protein and similar transmembrane domain as the β1 isoform of C18orf1.

be established. Analysis of multiple northern blots containing 23 human normal tissues revealed the highest level of PMEPA1 expression in prostate tissue. Although other tissues expressed PMEPA1, their relative expression was significantly lower as compared to prostate (FIG. 1). In situ RNA hybridization analysis of PMEPA1 expression in prostate tissues revealed abundant expression in the glandular epithelial compartment as compared to the stromal cells. However, both normal and tumor cells in tissue sections of primary tumor tissues revealed similar levels of expression.

Androgen Dependent Expression of PMEPA1

Figure 2A:
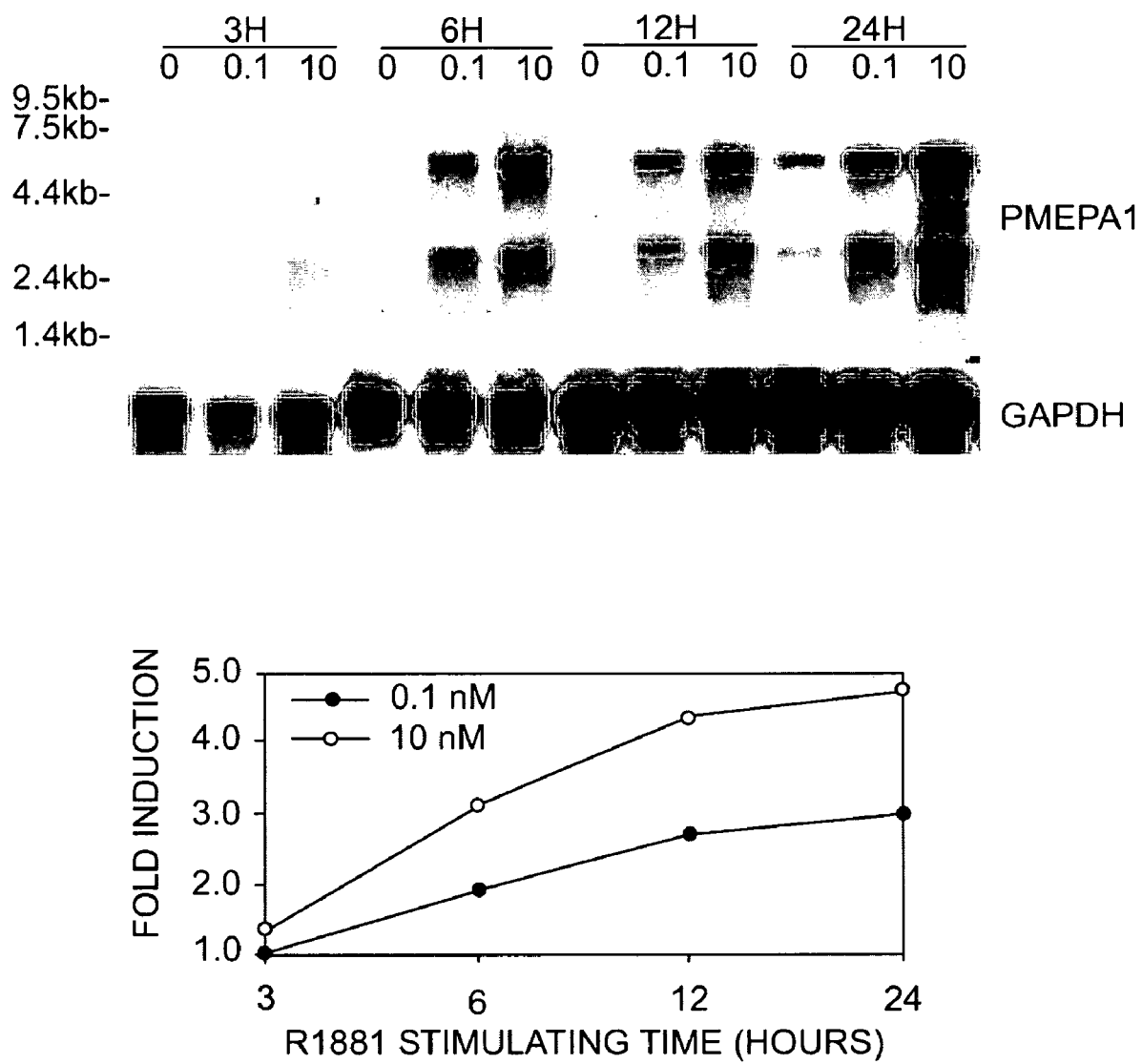
FIG. 2A is a Northern blot using PMEPA1 probe with mRNA derived from LNCaP cells with or without R1881 treatment for various durations.
Figure 2B:
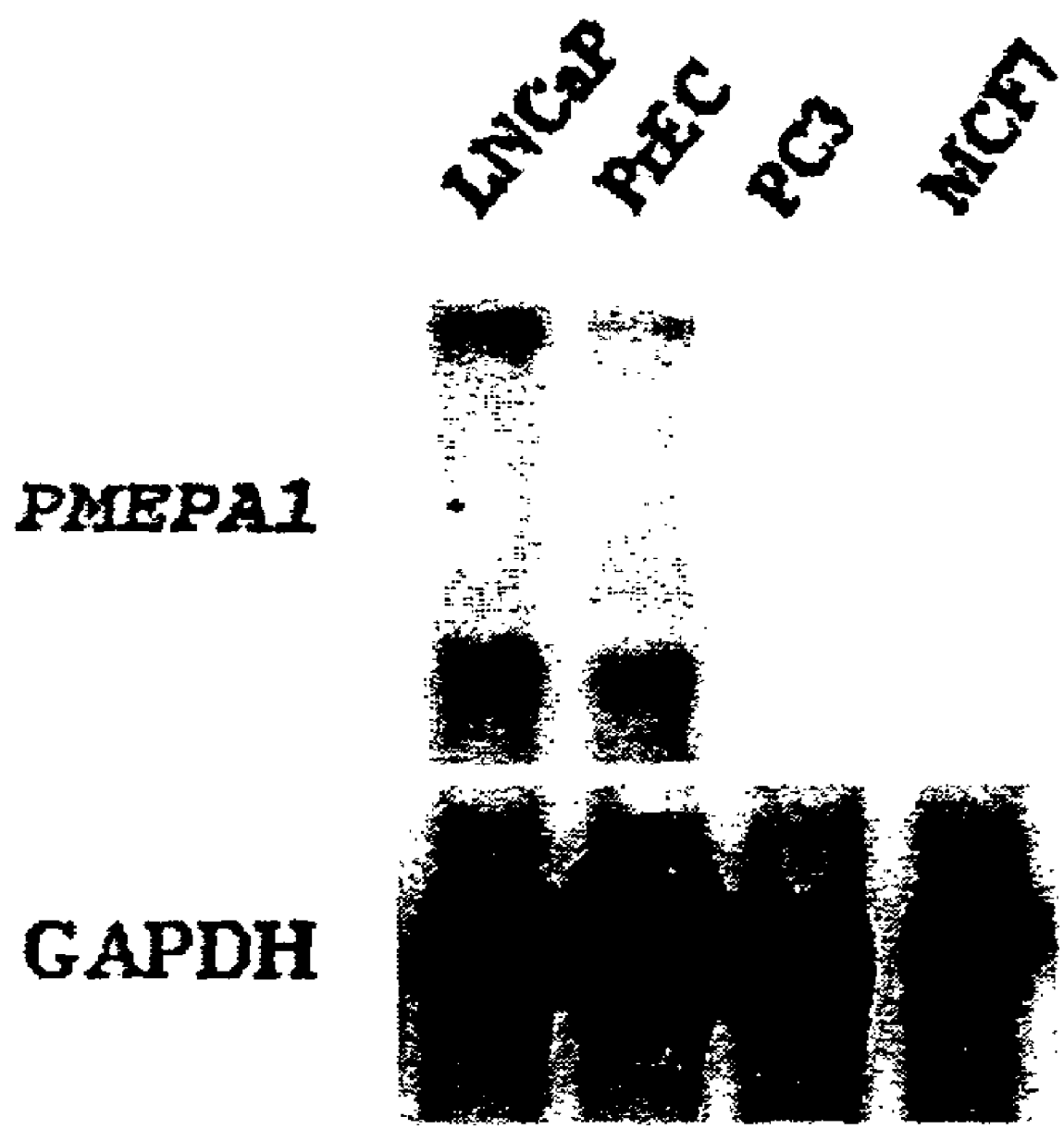
FIG. 2B is a Northern blot of PMEPA1 expression in primary epithelial cell cultures of normal prostate and prostate and breast cancer cell lines.

As discussed above, PMEPA1 was originally identified as a SAGE tag showing the highest fold induction (29-fold) by androgen. Androgen depletion of LNCaP cells resulted in decreased expression of PMEPA1. Androgen supplementation of the LNCAP cell culture media lacking androgen caused induction of both ~2.7 and ~5.0 bp RNA species of PMEPA1 in LNCAP cells in a dose and time dependent fashion (FIG. 2A). Basal level of PMEPA1 expression was detected in normal prostatic epithelial cell cultures and androgen-dependent LNCaP cells cultured in regular medium. PMEPA1 expression was not detected in AR negative CaP cells, PC3 or in the breast cancer cell line, MCF7 (FIG. 2B).

Evaluation of PMEPA1 expression in androgen sensitive and androgen refractory tumors of CWR 22 prostate cancer xenograft model Previous studies have described increased expression of ARGs in the "hormone refractory" CWR22R variants of the CWR22 xenograft, suggesting the activation of AR mediated cell signaling in relapsed CWR22 tumors following castration. The androgen sensitive CWR22 tumor expressed detect-

TABLE 2

```
  2 AELEFVQIIIIVVVMMVMVVVITCLLSHYKLSARSFISRHSQGRRREDALSSEGCLWPSE   61  PMEPA1
    AELEF QIIIIVVV  V VVVITCLL+HYK+S RSFI+R +Q RRRED L   EGCLWPS+
  3 AELEFAQIIIIVVVVTVMVVVIVCLLNHYKVSTRSFINRPNQSRRREDGLPQEGCLWPSD   62  C18orf1

62 STVSGNGIPEPQVYAPPRPTDRLAVPPFAQRERFHRFQPTYPYLQHEIDLPPTISLSDGE  121  PMEPA1
    S     G   E      PR   DR    P F QR+RF RFQPTYPY+QHEIDLPPTISLSDGE
 63 SAAPRLGASE--IMHAPRSRDRFTAPSFIQRDRFSRFQPTYPYVQHEIDLPPTISLSDGE  120  C18orf1

122 EPPPYQGPCTLQLRDPEQQLELNRESVRAPPNRTIFDSDLMDSARL-GGPCPPSSNSGIS  180  PMEPA1
    EPPPYQGPCTLQLRDPEQQ+ELNRESVRAPPNRTIFDSDL+D A   GGPCPPSSNSGIS
121 EPPPYQGPCTLQLRDPEQQMELNRESVRAPPNRTIFDSDLIDIAMYSGGPCPPSSNSGIS  180  C18orf1

181 ATCYGSGGRMEGPPPTYSEVIGHYPGSSFQHQQSSGPPSLLEGTRLHHTHIAPLESAAIW  240  PMEPA1
    A+     S GRMEGPPPTYSEV+GH+PG+SF H Q S    +   G+RL         ES +
181 ASTCSSNGRMEGPPPTYSEVMGHHPGASFLHHQRS---NAHRGSRLQFQQ-NNAESTIVP  236  C18orf1

241 SKEKDKQKGH 250  PMEPA1   (SEQ ID NO:11)
      K KD++ G+
237 IKGKDRKPGN 246  C18orf1  (SEQ ID NO:12)
```

In Table 2, a "+" denotes conservative substitution.

Analysis of PMEPA1 Expression

Northern hybridization revealed two transcripts of ~2.7 kb and ~5 kb using either PMEPA1 cDNA or oligo probe. The signal intensity of bands representing these two transcripts was very similar on the X-ray films of the northern blots. RT-PCR analysis of RNA from LNCaP cells with four pairs of primers covering different regions of PMEPA1 protein coding region revealed expected size of bands from PCR reactions, suggesting that two mRNA species on northern blot have identical sequences in the protein coding region and may exhibit differences in 5' and/or 3' non-coding regions. However, the exact relationship between the two bands remains to able level of PMEPA1 transcripts. However, three of the four CWR22R tumors exhibited increased PMEPA1 expression (FIG. 8).

EXAMPLE 8

Structural Features of the PMEPA1 Gene.

Analysis of a 1,141 base pair PMEPA1 cDNA sequence revealed an open reading frame of 759 nucleotides (SEQ ID NO:2) that encodes a 252 amino acid protein (SEQ ID NO:3). A protein motif search using ProfileScan (available from the Internet site provided by EMBnet) indicated the existence of a type Ib transmembrane domain between amino acid residues 9 to 25 of the PMEPA1 sequence. In addition, the motif search revealed two PY motifs in the PMEPA1 protein sequence, PPPY (SEQ ID NO:80) ("PY1") and PPTY (SEQ ID NO:81) ("PY2"). The PY motif is a proline-rich peptide sequence with a consensus PPXY sequence (where X represents any amino acid) that can bind to proteins with WW domains [Jolliffe et al., Biochem. J., 351: 557-565, 2000; Harvey et al., Trends Cell Biol., 9: 166-169, 1999; Hicke, Cell, 106: 527-530, 2001; Kumar et al., Biochem. Biophys. Res. Commun., 185: 1155-1161, 1992; Kumar et al., Genomics, 40: 435-443, 1997; Sudol, Trends Biochem. Sci., 21: 161-163, 1996; Harvey et al., J. Biol. Chem., 277: 9307-9317, 2002; and Brunschwig et al., Cancer Res., 63: 1568-1575, 2003].

A protein sequence homology search revealed that PMEPA1 has an 83% sequence identity with a mouse NEDD4 WW binding protein 4 ("N4WBP4," Accession number AK008976) (4), as shown below in Table 10. In Table 2, the + denotes a conservative substitution, and the PY motifs are underlined.

ated by PCR amplification of the PMEPA1 open reading frame. For PMEPA1-V5-pcDNA3.1 vector the following primers were used:

```
5'-GCTGCTGGAGAACTGAAGGCG-3'  (SEQ ID NO:69)
and
5'-GTGTCCTTTCTGTTTATCCTTC-3' (SEQ ID NO:70).

For PMEPA1-GFP-pEGFP-vector the primers used were:

5'-AAGCTTGCTGCTGGAGAACTGAAGGCG-3' (SEQ ID NO:71)
and
5'-GAATTCGGTGTCCTTTCTGTTTATC-3' (SEQ ID NO:72).
```

The V5 tag or GFP protein was fused at the carboxyl terminus of the PMEPA1 protein. The PCR product for generating PMEPA1-V5 was inserted into pcDNA3.1-V5-His expression vector (Invitrogen, Carlsbad, Calif.). The PCR product for generating PMEPA1-GFP was digested by HindIII and EcoRI and cloned into the same sites of pEGFP vector (Clontech, Palo Alto, Calif.). PMEPA1-PY motif mutants, in which the tyrosine residue (Y) was replaced with

TABLE 10

```
Human PMEPA1:   1  MAELEFVQXXXXXXXXXXXXXXXXTCLLSHYKLSARSFISRHSQGRRREDALSSEGCLWPS  60
                   + ELEFVQ                 TCLLSHYKLSARSFISRHSQ RRR+D LSSEGCLWPS
Mouse N4WBP4:  18  ITELEFVQIVVIVVVMMVMVVMITCLLSHYKLSARSFISRHSQARRRDDGLSSEGCLWPS  77

Human PMEPA1:  61  ESTVSGNGIPEPQVYAPPRPTDRLAVPPFAQRERFHRFQPTYPYLQHEIDLPPTISLSDG 120
                   ESTVSG G+PEPQVYAPPRPTDRLAVPPF QR    RFQPTYPYLQHEI LPPTISLSDG
Mouse N4WBP4:  78  ESTVSG-GMPEPQVYAPPRPTDRLAVPPFIQRS---RFQPTYPYLQHEIALPPTISLSDG 133

Human PMEPA1: 121  EEPPPYQGPCTLQLRDPEQQLELNRESVRAPPNRTIFDSDLMDSARLGGPCPPSSHSGIS 180
                   EEPPPYQGPCTLQLRDPEQQLELNRESVRAPPNRTIFDSDL+DS  LGGPCPPSSNSGIS
Mouse N4WBP4: 134  EEPPPYQGPCTLQLRDPEQQLELNRESVRAPPNRTIFDSDLIDSTMLGGPCPPSSNSGIS 193

Human PMEPA1: 181  ATCYGSGGRMEGPPPTYSEVIGHYPGSSFQHQQSSGPPSLLEGTRLHHTHIAPLESAAIW 240
                   ATCY SGGRMEGPPPTYSEVIGHYPGSSFQHQQS+GP SLLEGTRLHH+HIAPLE
Mouse N4WBP4: 194  ATCYSSGGRMEGPPPTYSEVIGHYPGSSFQHQQSNGPSSLLEGTRLHHSHIAPLE----- 248

Human PMEPA1: 241  SKEKDKQKGHPL 252 SEQ ID NO.3
                   +KEK+KQKGHPL
Mouse N4WBP4: 249  NKEKEKQKGHPL 260 SEQ ID NO.68
```

The WW domains of NEDD4 protein facilitate its binding to the target proteins via interaction with the PY motifs of NEDD4 binding proteins [Jolliffe et al., Biochem. J., 351: 557-565, 2000; Sudol M, Trends Biochem. Sci., 21: 161-163, 1996; Harvey et al., J. Biol. Chem., 277: 9307-9317, 2002; Macias et al., Nature, 382: 646-649, 1996; Chen et al., Proc. Natl. Acad. Sci., U S A., 92: 7819-7823, 1995; and Murillas et al., J. Biol. Chem., 277: 2897-2907, 2002]. The PMEPA1 protein sequence comprises two PY motifs, i.e., PPPY (SEQ ID NO:80) ("PY1") and PPTY (SEQ ID NO:81) ("PY2"). PY1 is in the central region of the PMEPA1 protein and PY2 is close to the carboxyl terminus of the PMEPA1 protein (Table 2). Therefore, the high protein sequence identity of PMEPA1 with N4WBP4 and the presence of PY motifs indicates that PMEPA1 is the human homolog of N4WBP4 and can bind to the NEDD4 protein and other proteins containing a WW domain.

EXAMPLE 9

PMEPA1-PY Motifs Interact with the WW Domains of NEDD4

Plasmids. Mammalian expression vectors encoding PMEPA1-V5 and PMEPA1-GFP fusion proteins were generan alanine residue (A), were created by using QuikChange Site-Directed Mutagenesis kit (Stratagene, La Jolla, Calif.) and using the PMEPA1-V5-pcDNA3.1 vector as a template. The plasmids of PMEPA1-PY motif mutants are as follows: PMEPA1-PY1m-V5-pcDNA3.1, with the first PY motif mutation (Y126A), PMEPA1-PY2m-V5-pcDNA3.1, with the second PY motif mutation (Y197A), and PMEPA1-PY1m/PY2m-V5-pcDNA3.1, with both the PY motif mutations (Y126A and Y197A). The sequences of all the inserts in expression vectors were verified by DNA sequencing.

A bacterial expression plasmid of human NEDD4 gene (pNEDD4WW-GST-pGEX-2TK) encoding all four WW-domains (Accession number XM_046129) fused to glutathione S-transferase (GST-WW fusion protein), was generated by PCR amplification of the coding region of the four WW-domains using the primers:

```
5'-GCAGGATCCCAACCAGATGCTGCTTGC-3' (SEQ ID NO:73)
and
5'-GCAGAATTCTTTTGTAATCCCTGGAGTA-3' (SEQ ID NO:74).
```

Normal prostate tissue derived cDNA was used as a PCR template and the amplified fragment was cloned into the BamHI/EcoRI sites of pGEX-2TK (Amersham Biotech, Piscataway, N.J.). A mammalian expression vector (NEDD4-GFP-pEGFP) encoding NEDD4-GFP fusion protein was generated using the following primers to generate the NEDD4 gene fragment by PCR.:

```
                                          (SEQ ID NO:75)
     5'-GCAAAGCTTGTCCGGTTTGCTGGAAGC-3'
     and
                                          (SEQ ID NO:76).
     5'-GCAGAATTCCCTTTTTGTTCTTATTGGTGAC-3'
```

PMEPA1 and NEDD4 Protein Binding Assays. The in vitro binding of PMEPA1 and NEDD4 was assessed by GST pull-down assays. GST-WW fusion protein was prepared and purified with glutathione-Sepharose beads per Amersham Biotech instructions. [$^{35}$S]methionine labeled proteins representing PMEPA1 and its mutants were generated by in vitro transcription/translation (TNT T7 quick coupled transcription/translation system, Promega, Madison, Wis.). Briefly, the PMEPA1-V5-pcDNA3.1 or the three mutants (2 μg) were incubated in 40 μl of reticulocyte lysate with 40 μCi of [$^{35}$S] methionine for 1.5 hrs at 30° C.

[$^{35}$S]methionine incorporation into protein was measured and samples were equalized on the basis of cpm. The GST-WW fusion protein bound to glutathione-Sepharose beads (5 μg) was incubated with the [$^{35}$S]methionine labeled lysates (12 μl) in 0.4 ml of phosphate-buffered saline (PBS, pH 7.4), 1 mM dithiothreitol, and protease inhibitors. The negative control for each [$^{35}$S]methionine labeled lysate represented a reaction mixture with equivalent amount of the lysate incubated with glutathione-Sepharose beads without GST-WW fusion protein. After 16 hours of incubation at 4° C., the beads were washed six times with PBS, resuspended in SDS-PAGE sample buffer and run on 12% SDS-PAGE gel under a reducing condition. The gels were dried and autoradiographed.

Results. The interaction of PMEPA1 and NEDD4 proteins in cells was evaluated by a co-immunoprecipitation assay. 293 cells (human embryonal kidney cells) were co-transfected with NEDD4-GFP-pEGFP vector and one of the PMEPA1-V5 expression vectors encoding either wt PMEPA1-V5 or the PY mutants of PMEPA1. Thirty-six hours later the cells were collected and lysed and the lysates were immunoprecipitated with anti-GFP antibody (Clontech, Palo Alto, Calif.) following the manufacturer's protocol. The immunoprecipitated proteins were subjected to immunoblotting with an anti-V5 tag antibody (Invitrogen).

In vitro translated [$^{35}$S]Methionine-labeled PMEPA1-V5 fusion protein, with the two intact PY motifs, showed binding to the GST-WW fusion protein (FIG. 6, lane 1). PMEPA1 with PY1 or PY2 mutations revealed significantly decreased binding to WW domains (FIG. 6, lane 2 and lane 3). Further, PMEPA1-V5 and NEDD4-GFP fusion proteins expressed in 293 cells showed strong association (FIG. 7, lane 1) and the mutant PMEPA1-V5 proteins having single mutation of PY1 or PY2 motif or double mutations of both PY1 and PY2 motifs exhibited significantly reduced binding to NEDD4 (FIG. 7, lanes 2, 3, and 4). Thus both in vitro and cell culture data reveal that PMEPA1 interacts with NEDD4 and this interaction involves the binding of the PMEPA1 PY motifs to WW domains. The PY2 motif mutation appeared to have a greater effect on binding of PMEPA1 to the NEDD4 WW domain.

The high protein sequence identity of PMEPA1 with N4WBP4 suggests that PMEPA1 is the human homolog of N4WBP4.

EXAMPLE 10

PMEPA1 Down Regulates Androgen Receptor and Affects Transcriptional Targets of the Androgen Receptor LNCaP cells were stably transfected with PMEPA1-GFP (PMEPA-GFP-LNCaP) and pEGFP control (pEGFP-LNCaP) expression vectors. To evaluate the effects of exogenous PMEPA1 expression on androgen receptor in LNCaP transfectants, cells were maintained in androgen-free media for 5 days which is known to down regulate endogenous PMEPA1 expression. Androgen receptor expression was evaluated in these cells after 5 days in the androgen free media (time, 0 hr). Androgen receptor expression was also evaluated in cells replenished with 0.1 nM R1881 for different time points (12 hours and 24 hours) after androgen withdrawal. Western blot analysis revealed reduced expression of androgen receptor protein in PMEPA-GFP-LNCaP cells (FIG. 4A). Decreased androgen receptor protein levels in PMEPA1 transfectants correlated with the reduced levels of PSA protein, a likely consequence of the attenuation of PSA gene expression due to relatively low levels of androgen receptor protein. PMEPA1 down-regulation of androgen receptor was further supported by results of relative increase of PSMA levels whose expression is normally down regulated by androgen receptor. These experiments showed that PMEPA1 down regulated androgen receptor, and androgen receptor transcriptional targets were affected correspondingly.

Because PMEPA1 is a NEDD4 binding protein, its effects on androgen receptor expression may involve the ubiquitin-proteasome pathway. To show that PMEPA1's effect on androgen receptor expression does not result from a general or non-specific effect of the upregulation of a ubiquitin protein ligase in the protein degradation pathway, we evaluated the effects of PMEPA1 on androgen receptor and the p27 protein, which is known to be degraded through a ubiquitin-dependent pathway. We generated a stable PMEPA1-GFP-Tet-LNCaP transfectant, in which the expression of PMEPA1-GFP fusion protein is regulated by tetracycline (Tet-off system, Clontech). As shown in FIG. 4B, cells cultured in the medium with tetracycline lacked PMEPA1 expression (Tet-off) but overexpressed PMEPA1 when cultured in the medium without tetracycline. The protein level of androgen receptor decreased dramatically in PMEPA1-overexpressing cells as compared to the relative expression of p27 or tubulin (FIG. 4B). Taken together, these data show that androgen receptor is a specific target of PMEPA1.

EXAMPLE 11

Golgi Association of PMEPA1 Protein.
Our studies also revealed that PMEPA1 is a Golgi-associated protein.

Immunofluorescence Assays. Plasmids were prepared as discussed above in Example 9. The immunofluorescent assays were performed following the procedure described by Harvey et al., *J. Biol. Chem.*, 277: 9307-9317, 2002. Briefly, stable transfectants of LNCaP cells harboring PMEPA1-GFP-pEGFP (LNCaP-PMEPA1-GFP transfectant) were grown on coverslips for two days, fixed in 2% paraformaldehyde for 15 minutes and permeabilized in 0.2% Triton X-100 for 2 minutes. Fixed and permeabilized cells were incubated with anti-GM130 (recognizes a cis-Golgi matrix protein) or anti-TGN38 (recognizes a protein localizing to Trans-Golgi Network, TGN) monoclonal antibodies (BD Transduction Laboratory, San Diego, Calif.) at 6.25 μg/ml for 30 minutes at room temperature. Cells were then washed to remove excess or non-specifically bound primary antibody followed by incubation with TRITC conjugated anti-mouse antibody (Sigma, ST. Louis, Mo.) at 1:100 dilution for 30 minutes at room temperature. The sections were mounted with fluoromount (Southern Associates, Birmingham, Ala.) and the images were processed with a Leica fluoromicroscope and Open-Lab software (Improvision, Lexington, Mass.).

Results. PMEPA1-GFP fusion protein showed perinuclear localization with a Golgi-like appearance. The images of sub-cellular location of GM130, a cis-Golgi protein, showed similar pattern as PMEPA1-GFP fusion protein. Superimposing the images of PMEPA1-GFP fusion protein and GM130 in LNCaP-PMEPA1-GFP transfectants confirmed the localization of PMEPA1-GFP fusion protein on cis-Golgi structure. We did not observe the co-localization of PMEPA1-GFP and TGN-38, which localizes to TGN.

The sub-cellular localization of PMEPA1 is similar to two other newly identified NEDD4 WW domain binding proteins, N4WBP5 and N4WBP5a, which also localize to the Golgi complex [Harvey et al., *J. Biol. Chem.*, 277: 9307-9317, 2002; Konstas et al., J. Biol. Chem., 277: 29406-29416, 2002]. N4WBP5a sequestered the trafficking of NEDD4/NEDD4-2 thereby increasing the activity of the epithelial sodium channel (EnaC), a known target down regulated by NEDD4 [Konstas et al., J. Biol. Chem., 277: 29406-29416, 2002]. As a highly androgen-regulated gene and a NEDD4 binding protein, the localization of PMEPA1 on the Golgi apparatus suggests that PMEPA1 is involved in protein turnover of androgen receptor targets.

EXAMPLE 12

PMEPA1 Inhibits Growth of Prostate Cancer Cells.

Colony-Forming Assays. To investigate the biologic effects of PMEPA1 expression in regulating cell growth and the contribution of PY motifs to such functions, we performed the colony-formation assay by transfecting various prostate cancer cell lines with expression vectors of the wild type PMEPA1 ("wt-PMEPA1") and PMEPA1-PY mutants.

Prostate cancer cell lines: LNCaP, PC3, and DU145 were purchased from ATCC (Rockville, Md.) and grown in the cell culture media as described by the supplier. The LNCaP sublines C4, C4-2 and C4-2B [Hsieh et al., Cancer Res., 53: 2852-7, 1993; Thalmann et al., Cancer Res., 54: 2577-81, 1994; and Wu et al., Int. J. Cancer, 77: 887-94, 1998] were purchased from Urocor (Oklahoma, Okla.) and cultured in T medium (5% FBS, 80% DMEM, 20% F12, 5 ug/ml insulin, 13.65 pg/ml Triiodo-Thyronine, 5 ug/ml apo-transferrin, 0.244 ug/ml biotin, 25 ug/ml adenine).

Three micrograms of plasmids (PMEPA1-V5-pcDNA3.1 or vector without PMEPA1 insert) were transfected into the 50-70% confluent cells in triplicate in 60-mm petri dishes with Lipofectamine (Invitrogen, Carlsbad, Calif.). Tumor suppressor gene p53 (wt), and mt p53 (R175H and G245D) were also used in parallel as controls. Approximately 36 hours later, selection with G418 at 800 μg/ml (DU145 and PC3) or 400 μg/ml (LNCaP and its sublines) was initiated. Cells were maintained with G418-containing medium that was changed every 3-4 days. After 2-4 weeks of selection, the cells were rinsed with 1×PBS, fixed with 2% formaldehyde in 1×PBS for 15 minutes, stained with 0.5% crystal violet in 1×PBS for 15 minutes, and rinsed 1-2 times with distilled H₂O. Colonies visible in each dish without magnification were counted by Open-Lab software.

To assess the effects of the PY motif mutations on the colony-forming ability of PMEPA1, LNCaP and PC3 cells were also transfected with PMEPA1 mutants: PMEPA1-PY1m-pcDNA3.1, PMEPA1-PY2m-pcDNA3.1, or PMEPA1-PY1m/PY2m-pcDNA3.1. PMEPA1-V5-pcDNA3.1 and expression vector without insert served as positive and negative controls, respectively, for the PMEPA1 mutants. Two independent colony-forming assays were performed as above.

As shown in FIGS. 3A-F, the colony-forming abilities of prostate cancer cell lines DU145, PC3, LNCaP, and LNCaP sublines were significantly suppressed by transfection of the sense version of the wt-PMEPA1 expression vector. Under these conditions wt-p53 showed similar cell growth inhibition (data not shown).

Figure 3A:
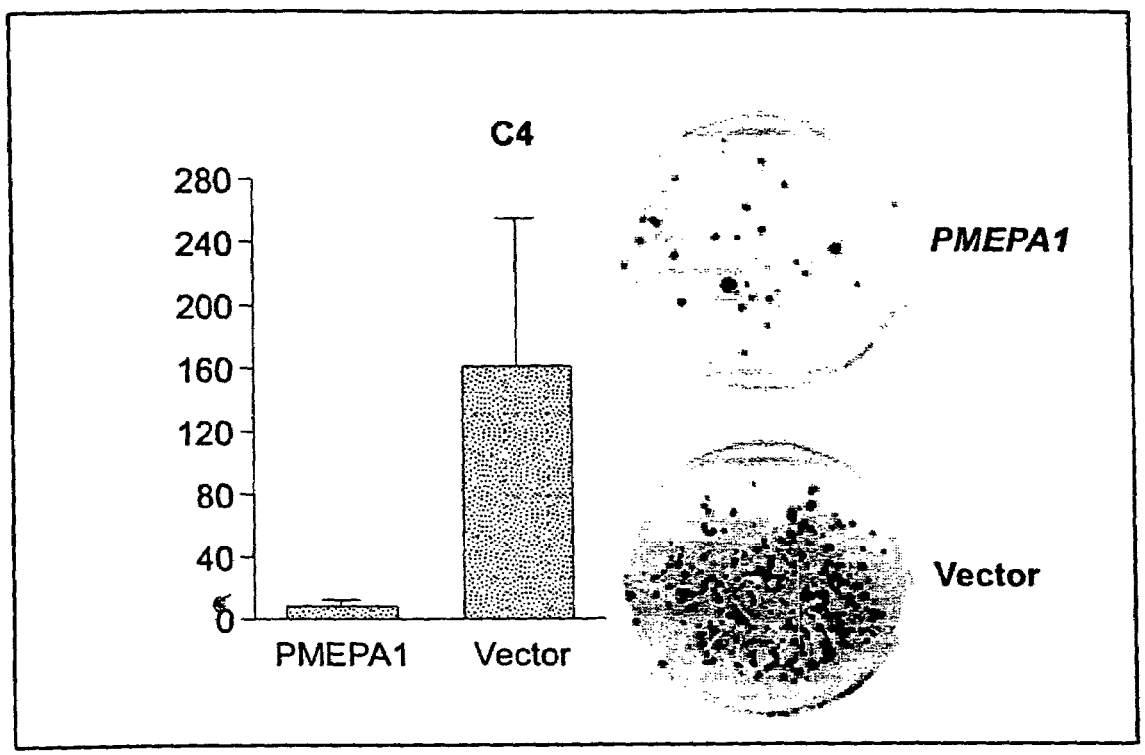
FIGS. 3A-H show the effect of PMEPA1 on colony formation. Prostate tumor cell lines: C4 (FIG. 3A), C4-2 (FIG. 3B), C4-2B (FIG. 3C), LNCaP (FIG. 3D), DU145 (FIG. 3E), and PC3 (FIG. 3F) were transfected with 3 μg of each of PMEPA1-V5-pcDNA3.1 (PMEPA1) and pcDNA3.1 vector (Vector) in triplicate sets. In a separate experiments LNCaP (FIG. 3G) and PC3 (FIG. 3H) cells were transfected with control vector or expression vectors encoding wt-PMEPA1 or PMEPA1-PY mutants (1. PMEPA1-V5-pcDNA3.1, 2. PMEPA1-PY1m-pcDNA3.1, 3. PMEPA1-PY2m-pcDNA3.1, 4. PMEPA1-PY1m/PY2m-pcDNA3. 1, and 5. pcDNA3. 1). Transfected cells were selected for plasmid-containing cells with G418 for 3 weeks and surviving cells were fixed and stained with crystal violet. In each experiment, the number of colonies per dish were counted and displayed as histograms, representing the mean number of colonies±SD of the triplicate sets. For each cell line, a photograph of one dish of cells treated with 3 μg of each plasmid is also shown.
Figure 3B:
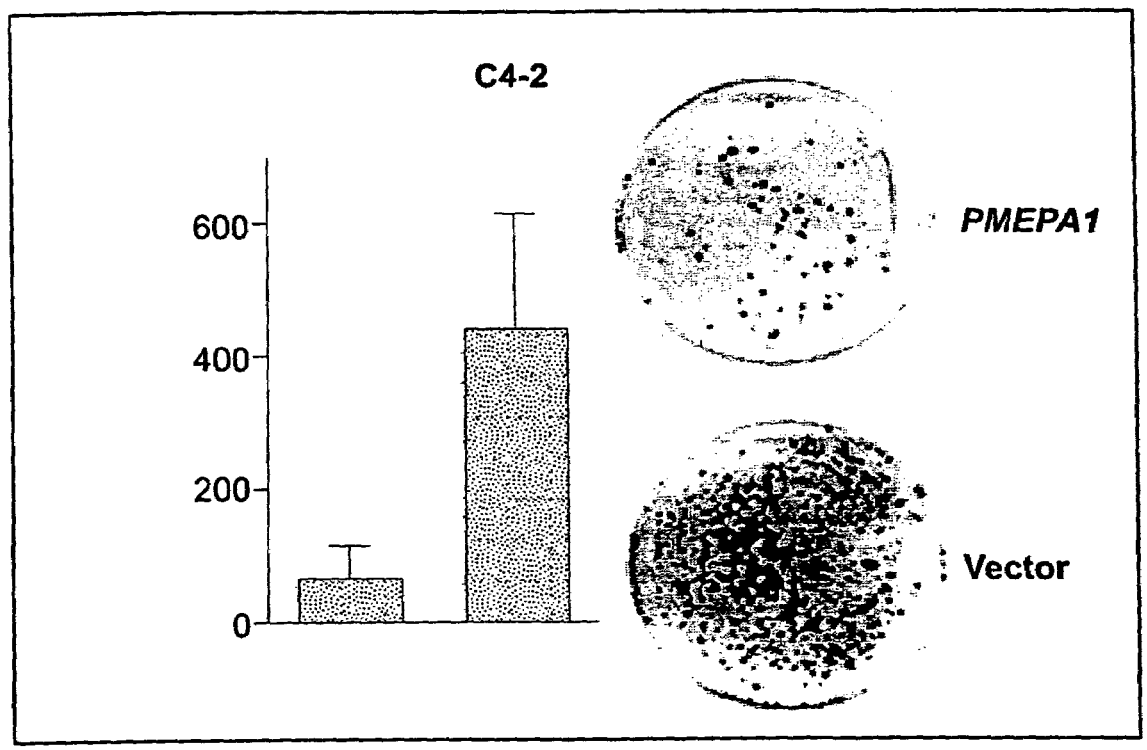
Figure 3C:
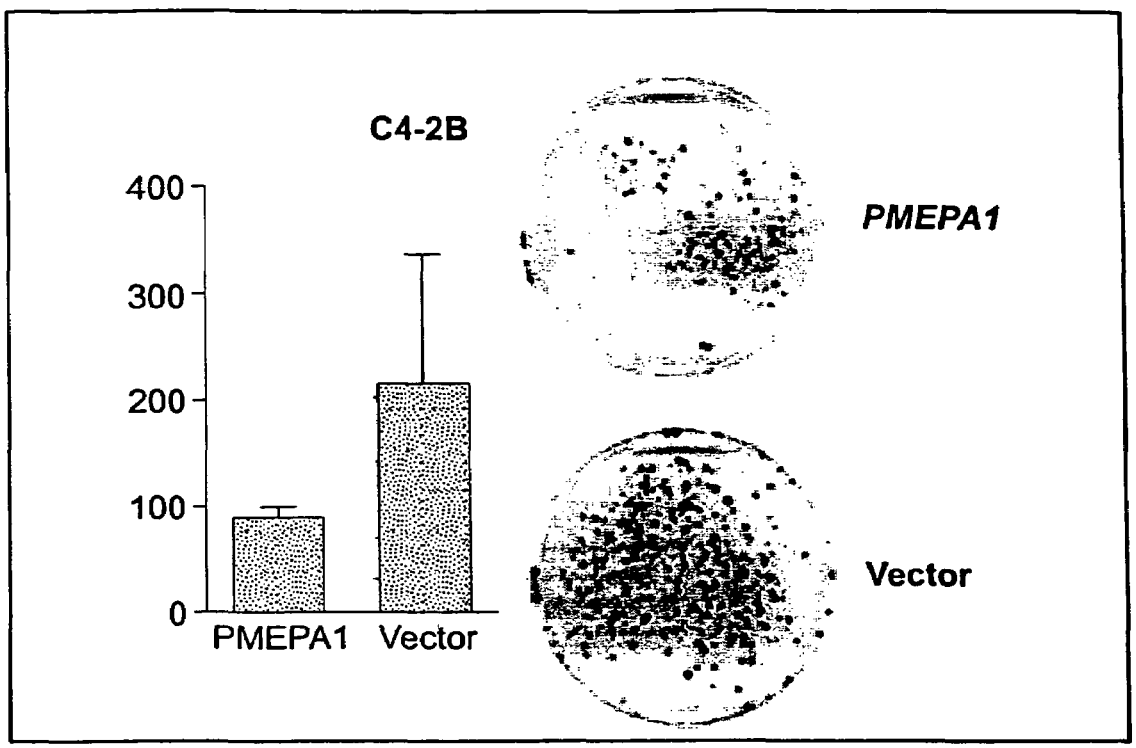
Figure 3D:
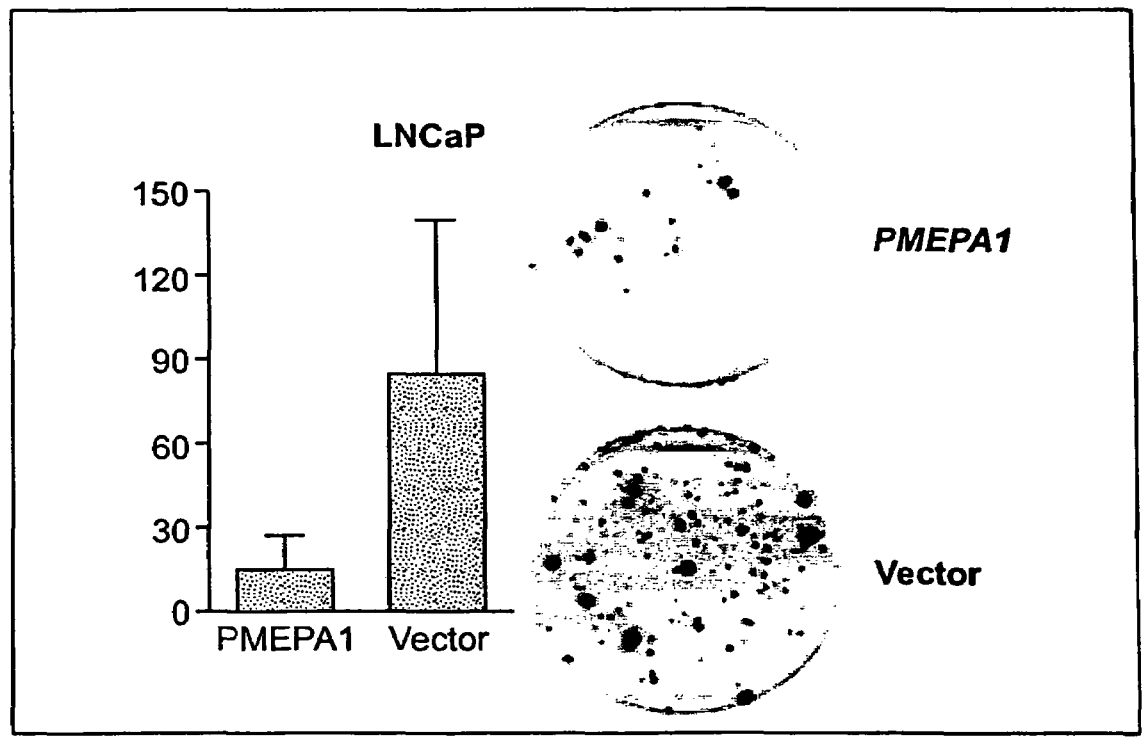
Figure 3E:
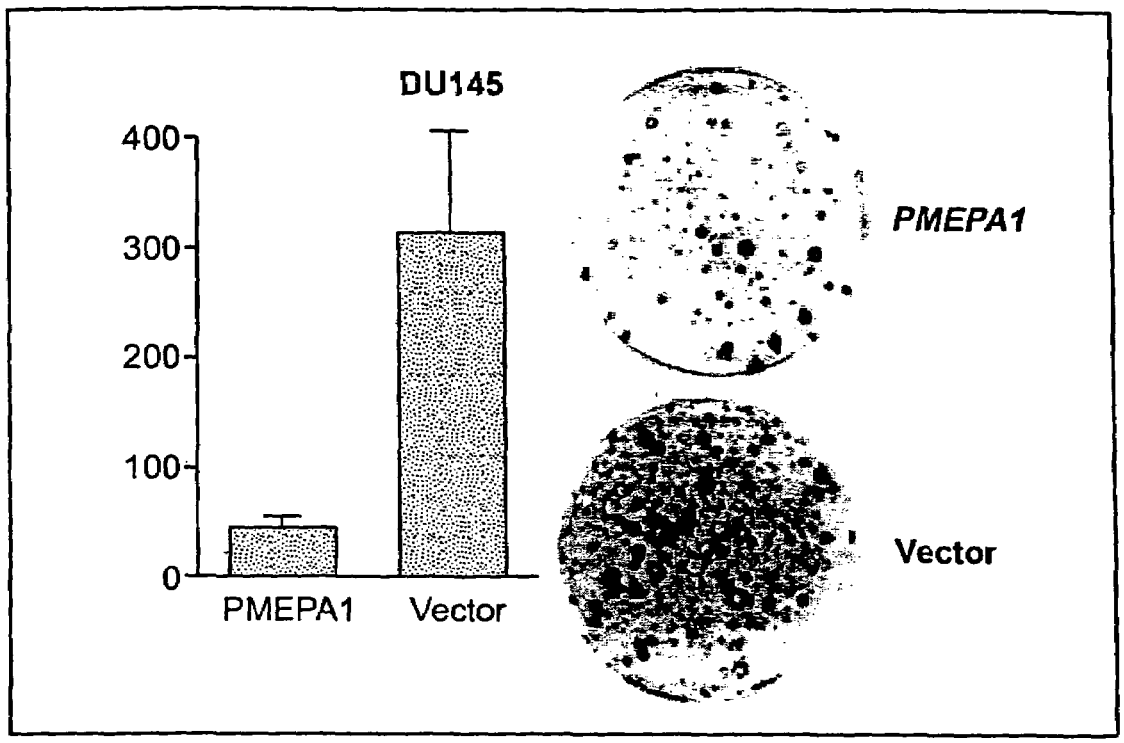
Figure 3F:
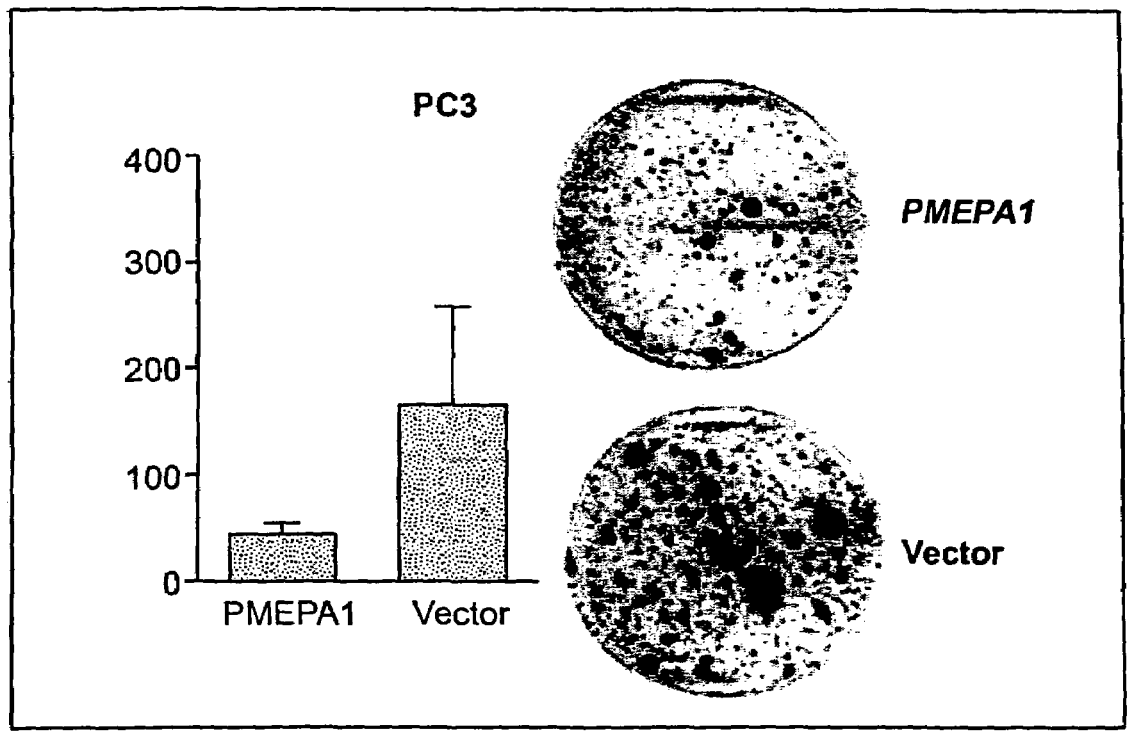
Figure 3H:
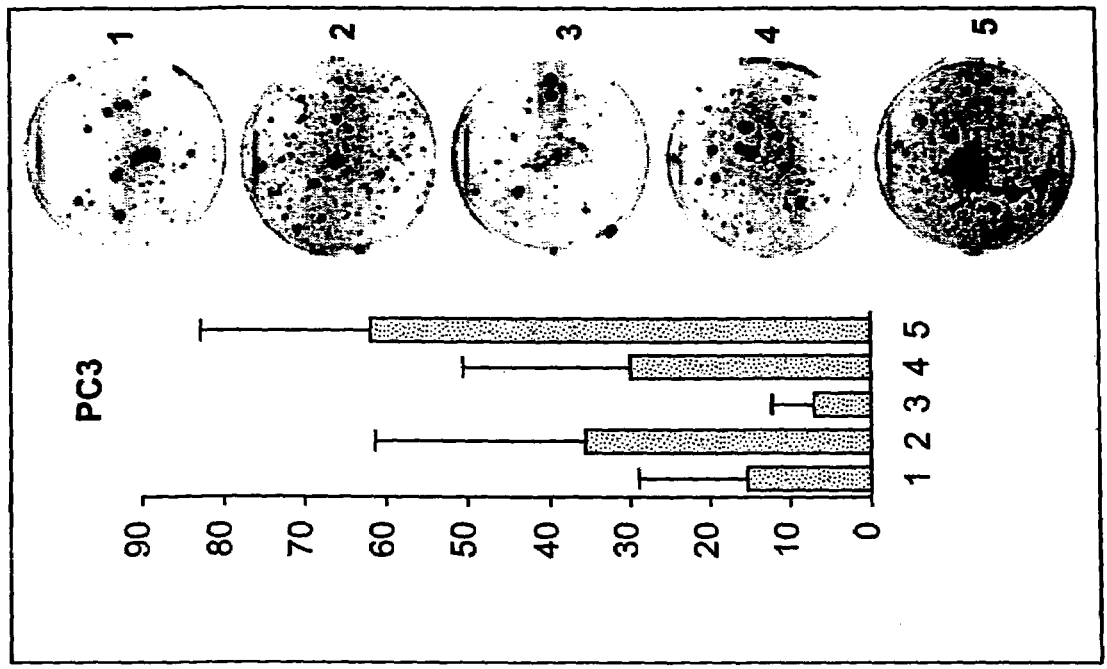
Figure 3G:
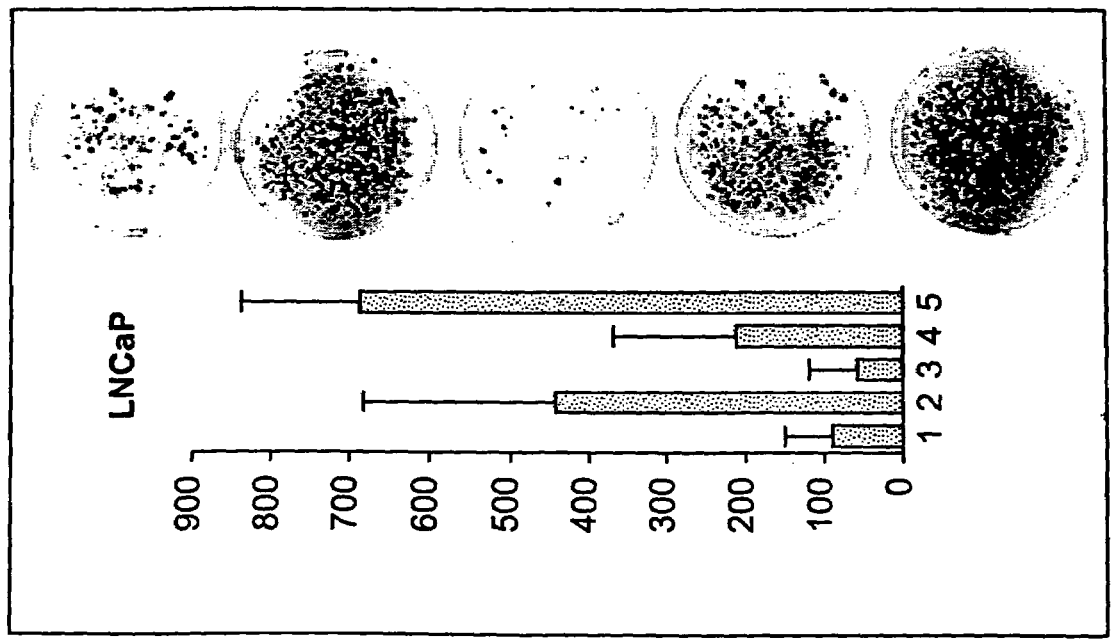

In two independent experiments, mutation of the PY1 motif appears to abolish the inhibition of colony formation by wt-PMEPA1, emphasizing the role of the PY1 motif in PMEPA1 and NEDD4 interactions and the biologic functions of PMEPA1 (FIGS. 3G-H). The growth inhibitory effect of PMEPA1 appears to be linked to the interactions of PY1 motif to NEDD4 WW domain. This interpretation is based on the striking observations showing distinctively more colonies with PY1 motif mutant in comparison to wt-PMEPA1.

Cell Proliferation Analysis. To further evaluate the growth inhibitory effects of PMEPA1 on prostate cancer cells, a stable PMEPA1-GFP-Tet LNCaP transfectant was generated. Expression of PMEPA1-GFP fusion protein in these cells was negatively regulated by tetracycline in the medium (Clontech). For cell proliferation assays, three thousand PMEPA1-GFP-Tet LNCaP cells were seeded in 96-well plates with or without 1 μg/ml of tetracycline in the medium. CellTiter 96 Aqueous One Solution kit (Promega, Madison, Wis.) was used to measure the cell proliferation according to the manufacturer's instructions.

The growth inhibitory effect of PMEPA1 has been further confirmed by the cell proliferation characteristics of stable PMEPA1-GFP-Tet-LNCaP cells, where exogenous PMEPA1 is upregulated in the absence of tetracycline. The growth of the PMEPA1-GFP-Tet LNCaP cells in tetracycline negative medium is significantly slower than that of PMEPA1-tet LNCaP transfectant in tetracycline positive medium (FIG. 5). LNCaP cells with PMEPA1 overexpression also revealed increased RB phosphorylation further confirming the cell growth inhibitory effect of PMEPA1 (data not shown).

PMEPA1 is expressed in androgen receptor positive prostate cancer cell lines, including LNCaP and its sublines (C4, C4-2 and C4-2B). LNCaP cells are androgen dependent for growth. Even though the growth of LNCaP sublines is androgen independent, androgen receptor is critical for their proliferation [Zegarra-Moro et al., *Cancer Res.*, 62: 1008-1013, 2002]. We observed that overexpression of PMEPA1 by transfecting the PMEPA1 expression vector into LNCaP and its sublines significantly inhibited the cell proliferation. Since our preliminary observations showed that PMEPA1 overexpression in LNCaP cells resulted in altered expression of androgen receptor downstream genes (Xu et al. unpublished data), we hypothesized that the growth inhibitory effect of PMEPA1 on LNCaP and its sublines may be mediated directly or indirectly through affecting androgen receptor functions. Despite the growth inhibitory effect on androgen receptor positive prostate cancer cell lines, PMEPA1 was also found to inhibit the growth of androgen receptor negative prostate tumor cells, DU145 and PC3, suggesting that the growth inhibitory effects of PMEPA1 on DU145 and PC3 could be mediated through alternative mechanisms, e.g., regulation of other nuclear steroid receptors by PMEPA1. Nonetheless, inhibition of prostate cancer cell growth by PMEPA1 implicates PMEPA1 in control of prostate cancer development.

EXAMPLE 13

Decreased PMEPA1 Expression in Prostate Tumor Tissues.

We also evaluated the relationship of alterations in PMEPA1 expression to the clinico-pathologic features of prostate cancer.

Prostate Tissue Specimens, Laser Capture Microdissection (LCM) and Quantitative RT-PCR (QRT-PCR) Assay. Matched prostate cancer and normal tissues were derived from radical prostatectomy specimens from 62 CaP patients treated at Walter Reed Army Medical Center (under an IRB-approved protocol). The procedures of collecting specimens were previously described [Xu et al., Cancer Res. 60: 6568-6572, 2000]. Ten micron frozen sections were prepared and stored at −70° C. Histologically normal prostate epithelial cells and prostate tumor cells from each patient were harvested using LCM equipment according to the protocol provided by the manufacturer (Arcturus Engineering, Mountain View, Calif.).

Total RNA was prepared from the harvested normal and tumor prostate epithelial cells as previously described [Xu et al., Cancer Res. 60: 6568-6572, 2000] and quantified with Fluorometer (Bio-Rad, Hercules, Calif.). QRT-PCR was conducted using 0.1 ng of total RNA from paired normal and tumor cells. PMEPA1 PCR primers were carefully designed that only amplify PMEPA1 but not STAG1, an alternatively spliced form of PMEPA1 [Rae et al., Mol. Carcinog., 32: 44-53, 2001]. The PCR primers were:

```
5'-CATGATCCCCGAGCTGCT-3' (SEQ ID NO:77)
and
5'-TGATCTGAACAAACTCCAGCTCC-3' (SEQ ID NO:78),
and the labeled probe was:
5'-AGGCGGACAGTCTCCTGCGAAAC-3' (SEQ ID NO:79).
```

GAPDH gene expression was detected as the internal control (PE Applied Biosystems, Foster, Calif.). Paired triplicate samples (one lacking RT and duplicate with RT) were amplified in 50 μl volumes containing the manufacturer's recommended universal reagent, proper primers and probe of PMEPA1 or GAPDH using 7700 sequence detection system (PE Applied Biosystems, Foster, Calif.).

Results were plotted as average cycle threshold (cT) values for each duplicate sample minus the average duplicate cT values for GAPDH. Differences between matched tumor (T) and normal (N) samples were calculated using 2 exp($cT_{tumor}$−$cT_{normal}$) and expressed as fold changes in expression. The expression status of PMEPA1 was further categorized as either: 1) overexpression in tumor tissue (T>N), defined as 1+(1.5-3 fold), 2+(3.1-10 fold), 3+(10.1-20 fold) and 4+(>20 fold) increased expression as compared with matched normal tissue; 2) reduced expression in tumor tissue (T<N), defined as 1−(1.5-3 fold), 2−(3.1-10 fold), 3−(10.1-20 fold) and 4−(>20 fold) decreased expression as compared with matched normal tissue; or 3) no change (T=N), defined as 0 (<1.5 fold). No detectable PMEPA1 expression in one of the specimens of tumor/normal pairs was scored as 4+ for increased or 4− for decreased expression.

Statistical analysis was performed with the SPSS software package. The association between PMEPA1 expression and clinico-pathological features was analyzed using chi-square tests. The Kaplan-Meier curves were applied to display the PSA-recurrence-free survival data. A p value <0.05 was considered as statistically significant.

The overall expression pattern of PMEPA1 primary prostate cancer is shown below in Table 11.

TABLE 11

| PMEPA1 Expression | Number of Patients/ Group (%) | Degree of PMEPA1 Expression | |
|---|---|---|---|
| | | Quantity | Number (%) |
| T < N | 40 (64.5) | 1− | 11 (27.5) |
| | | 2− | 17 (42.5) |
| | | 3− | 5 (12.5) |
| | | 4− | 7 (17.5) |
| T > N | 10 (16.1) | 1+ | 6 (60.0) |
| | | 2+ | 4 (40.0) |
| | | 3+ | |
| | | 4+ | |
| T = N | 12 (19.4) | 0 | |

Comparison of PMEPA1 expression between tumor and normal cells revealed tumor cell associated decreased expression (T<N) in 64.5% tumor specimens (40 of 62), increased expression (T>N) in 16.1% specimens (10 of 62) and no change (T=N) in 19.4% specimens (12 of 62). When these expression patterns were stratified by organ-confined (pT2) and non-organ-confined (pT3) disease, a higher percentage of PMEPA1 reduction was seen in pT3 (74%) vs. pT2 (48%). Because the T>N group has a small number of cases, we combined the T>N group and the T=N group (T≧N group). As shown below in Table 12, comparison of the clinico-pathologic parameters between the T<N group and the T≧N group revealed that the T<N group had a significantly higher percentage of patients with pT3 tumors (p=0.035) and more patients in this group had a higher level of preoperative serum prostate specific antigen (PSA) (p=0.023).

TABLE 12

| PMEPA1 Expression | Pathologic Stage (%) | | PSA Range (%) | | | PSA Recurrence (%) | | Time to Recurrence after Surgery (month) |
|---|---|---|---|---|---|---|---|---|
| | T2 | T3 | ≦4 ng/ml | 4.1-10 ng/ml | 10.1-20 ng/ml | No | Yes | Mean ± SE |
| T < N | 11 (27.5) | 29 (72.5) | 1 (2.5) | 30 (75.0) | 9 (22.5) | 29 (72.5) | 11 (27.5) | 8.2 ± 3.4 |
| T ≧ N | 12 (54.5) | 10 (45.5) | 5 (22.7) | 15 (68.2) | 2 (9.1) | 19 (86.4) | 3 (13.6) | 18.4 ± 6.3 |
| p Value | 0.035 | | 0.023 | | | 0.211 | | 0.18 |

Out of 62 patients whose tumors were analyzed for PMEPA1 expression, 14 patients showed prostate cancer recurrence as defined by serum PSA level equal or higher than 0.2 ng/ml after prostatectomy. Of the 14 patients, 11 showed reduced tumor associated PMEPA1 expression (78.5%). Reduced PMEPA1 expression seems to associate with a higher recurrence rate and a shorter duration to recurrence after surgery, even through the statistical analysis did not reveal a significant difference. The absence of a significant difference might be due to the small number of patients.

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention.

TABLE 3

Genes Regulated by Androgen:
SAGE Data Derived from CPDR SAGE Library

| Accession | Description | Effect of Androgen |
|---|---|---|
| AA310984 | EST | Up-regulated by Androgen |
| M26663 | *Homo sapiens* prostate-specific antigen mRNA, complete cds.* | Up-regulated by Androgen |
| AA508573 | Human nucleolin gene, complete cds | Up-regulated by Androgen |
| AB020637 | *Homo sapiens* mRNA for KIAA0830 protein, partial cds. | Up-regulated by Androgen |
| AA280663 | EST | Up-regulated by Androgen |
| U31657 | KRAB-associated protein 1 | Up-regulated by Androgen |
| AI879709 | EST | Up-regulated by Androgen |
| AA602190 | EST | Up-regulated by Androgen |
| AF035587 | *Homo sapiens* X-ray repair cross-complementing protein 2 (XRCC2) | Up-regulated by Androgen |
| AF151898 | *Homo sapiens* CGI-140 protein mRNA | Up-regulated by Androgen |
| AA418786 | No reliable matches, only see in two linberary (1 each) | Up-regulated by Androgen |
| AI308812 | EST | Up-regulated by Androgen |
| X59408 | Membrane cofactor protein (CD46, trophoblast-lymphocyte cross-reactive antigen) | Up-regulated by Androgen |
| X81817 | Accessory proteins BAP31/BAP29 | Up-regulated by Androgen |
| AF071538 | homo sapiens Ets transcription factor PDEF (PDEF) mRNA, complete | Up-regulated by Androgen |
| NM_003201 | Transcription factor 6-like 1 (mitochondrial transcription factor 1-like) | Up-regulated by Androgen |
| U41387 | Human Gu protein mRNA, partial cds. | Up-regulated by Androgen |
| U58855 | Guanylate cyclase 1, soluble, alpha 3 | Up-regulated by Androgen |
| X12794 | Human v-erbA related ear-2 gene. | Up-regulated by Androgen |
| U88542 | Mus musculus homeobox protein Nkx3.1 | Up-regulated by Androgen |
| D89729 | *Homo sapiens* mRNA for CRM1 protein, complete cds. | Up-regulated by Androgen |
| U75329 | TMPRSS2 | Up-regulated by Androgen |
| AA062976 | EST | Up-regulated by Androgen |
| L12168 | *Homo sapiens* adenylyl cyclase-associated protein (CAP) mRNA | Up-regulated by Androgen |
| AA043945 | EST | Up-regulated by Androgen |
| AF026291 | *Homo sapiens* chaperonin containing t-complex polypeptide 1, delta | Up-regulated by Androgen |
| AB002301 | Human mRNA for KIAA0303 gene, partial cds. | Up-regulated by Androgen |
| D13643 | Human mRNA for KIAA0018 gene, complete cds. | Up-regulated by Androgen |
| AI310341 | EST | Up-regulated by Androgen |
| U49436 | Human translation initiation factor 5 (eIF5) mRNA, complete cds | Up-regulated by Androgen |
| S79862 | Proteasome (prosome, macropain) 26S subunit, non-ATPase, 5 | Up-regulated by Androgen |
| M14200 | Human diazepam binding inhibitor (DBI) mRNA, complete cds. | Up-regulated by Androgen |
| AA653318 | FK506-binding protein 5 | Up-regulated by Androgen |
| L07493 | *Homo sapiens* replication protein A 14 kDa subunit (RPA) mRNA, | Up-regulated by Androgen |
| AJ011916 | *Homo sapiens* mRNA for hypothetical protein. | Up-regulated by Androgen |
| AA130537 | EST | Up-regulated by Androgen |
| D16373 | Human mRNA for dihydrolipoamide succinyltransferase, complete cds. | Up-regulated by Androgen |
| AL096857 | Novel human mRNA from chromosome 1 | Up-regulated by Androgen |
| AF007157 | *Homo sapiens* clone 23856 unknown mRNA, partial cds. | Up-regulated by Androgen |
| AA425929 | NADH dehydrogenase (ubiquinone) 1 beta subcomplex, 10 (22 kD, PDSW) | Up-regulated by Androgen |
| AI357815 | EST | Up-regulated by Androgen |
| D83778 | Human mRNA for KIAA0194 gene, partial cds. | Up-regulated by Androgen |

TABLE 3-continued

Genes Regulated by Androgen:
SAGE Data Derived from CPDR SAGE Library

| Accession | Description | Effect of Androgen |
|---|---|---|
| AF000979 | *Homo sapiens* testis-specific Basic Protein Y 1 (BPY1) mRNA, | Up-regulated by Androgen |
| AA889510 | EST | Up-regulated by Androgen |
| AB018330 | *Homo sapiens* mRNA for KIAA0787 protein, partial cds. | Up-regulated by Androgen |
| AA026941 | EST | Up-regulated by Androgen |
| AA532377 | Chromosome 1 open reading frame 8 | Up-regulated by Androgen |
| AF010313 | *Homo sapiens* Pig8 (PIG8) mRNA (etoposide-induced mRNA), complete cds. | Up-regulated by Androgen |
| L06328 | Human voltage-dependent anion channel isoform 2 (VDAC) mRNA, | Up-regulated by Androgen |
| U41804 | Human putative T1/ST2 receptor binding protein precursor mRNA, | Up-regulated by Androgen |
| AB020676 | *Homo sapiens* mRNA for KIAA0869 protein, partial cds. | Up-regulated by Androgen |
| J03503 | Human pyruvate dehydrogenase E1-alpha subunit mRNA, cds. | Up-regulated by Androgen |
| AA421098 | EST | Up-regulated by Androgen |
| AF072836 | Sox-like transcriptional factor | Up-regulated by Androgen |
| AA115355 | EST | Up-regulated by Androgen |
| AF118240 | *Homo sapiens*, peroxisomal biogenesis factor 16 (PEX16) mRNA, complete | Up-regulated by Androgen |
| AA011178 | EST | Up-regulated by Androgen |
| X15573 | Human liver-type 1-phosphofructokinase (PFKL) mRNA, complete cds. | Up-regulated by Androgen |
| AA120930 | EST | Up-regulated by Androgen |
| AB002321 | Human mRNA for KIAA0323 gene, partial cds | Up-regulated by Androgen |
| AF151837 | *Homo sapiens* CGI-79 protein mRNA, complete cds | Up-regulated by Androgen |
| AA481027 | EST | Up-regulated by Androgen |
| AA039343 | EST | Up-regulated by Androgen |
| U09716 | Human mannose-specific lectin (MR60) mRNA, complete cds. | Up-regulated by Androgen |
| AF044773 | *Homo sapiens* breakpoint cluster region protein 1 (BCRG1) mRNA | Up-regulated by Androgen |
| US1586 | Human siah binding protein 1 (SiahBP1) mRNA, partial cds. | Up-regulated by Androgen |
| M36341 | Human ADP-ribosylation factor 4 (ARF4) mRNA, complete cds. | Up-regulated by Androgen |
| AI282096 | EST | Up-regulated by Androgen |
| W45510 | RAB7, member RAS oncogene family-like 1 | Up-regulated by Androgen |
| X16135 | Human mRNA for novel heterogeneous nuclear RNP protein, L protein | Up-regulated by Androgen |
| AF052134 | *Homo sapiens* clone 23585 mRNA sequence, AF052134 | Up-regulated by Androgen |
| D26068 | Williams-Beuren syndrome chromosome region 1 | Up-regulated by Androgen |
| X69433 | *H. sapiens* mRNA for mitochondrial isocitrate dehydrogenase (NADP+). | Up-regulated by Androgen |
| X61123 | B-cell translocation gene 1, anti-proliferative | Up-regulated by Androgen |
| X63423 | *H. sapiens* mRNA for delta-subunit of mitochondrial F1F0 ATP-synthase | Up-regulated by Androgen |
| AJ010025 | *Homo sapiens* mRNA for unr-interacting protein. | Down-regulated by Androgen |
| AF003938 | *Homo sapiens* thioredoxin-like protein mRNA, complete cds. | Down-regulated by Androgen |
| AB014536 | *Homo sapiens* copine III (CPNE3) mRNA | Down-regulated by Androgen |
| AA504468 | EST | Down-regulated by Androgen |
| NM_001273 | Chromodomain helicase DNA binding protein 4 | Down-regulated by Androgen |
| AA015746 | *Homo sapiens* mRNA; cDNA DKFZp586H0722 (from clone DKFZp586H0722) | Down-regulated by Androgen |
| AA552354 | EST | Down-regulated by Androgen |
| AA025744 | 3-prime-phosphoadenosine 5-prime-phosphosulfate synthase 2 | Down-regulated by Androgen |
| X71129 | *H. sapiens* mRNA for electron transfer flavoprotein beta subunit | Down-regulated by Androgen |
| AA046050 | EST | Down-regulated by Androgen |
| U57052 | Human Hoxb-13 mRNA, complete cds | Down-regulated by Androgen |
| AA400137 | EST | Down-regulated by Androgen |
| AA487586 | EST | Down-regulated by Androgen |
| J04208 | Human inosine-5'-monophosphate dehydrogenase (IMP) mRNA | Down-regulated by Androgen |
| M64722 | Testosterone-repressed prostate message 2 (apolipoprotein J) | Down-regulated by Androgen |
| AI743483 | EST | Down-regulated by Androgen |
| AA476914 | EST | Down-regulated by Androgen |
| AA026691 | EST | Down-regulated by Androgen |

TABLE 3-continued

Genes Regulated by Androgen:
SAGE Data Derived from CPDR SAGE Library

| Accession | Description | Effect of Androgen |
|---|---|---|
| AI014986 | EST | Down-regulated by Androgen |
| X85373 | Small nuclear ribonucleoprotein polypeptide G | Down-regulated by Androgen |
| U07231 | G-rich RNA sequence binding factor 1 | Down-regulated by Androgen |
| T97753 | Glycogen synthase 2 (liver) | Down-regulated by Androgen |
| AA234050 | EST | Down-regulated by Androgen |
| AI015143 | EST | Down-regulated by Androgen |
| U09196 | Human 1.1 kb mRNA upregulated in retinoic acid treated HL-60 neutrophilic cells. | Down-regulated by Androgen |
| AA977749 | EST | Down-regulated by Androgen |
| NM_006451 | Polyadenylate binding protein-interacting protein 1 | Down-regulated by Androgen |
| AI818296 | EST | Down-regulated by Androgen |
| AI250561 | EST | Down-regulated by Androgen |
| AA063613 | EST | Down-regulated by Androgen |
| U59209 | Hs.183596: UDP glycosyltransferase 2 family, polypeptide B17, U59209 | Down-regulated by Androgen |
| Z11559 | Iron-responsive element binding protein 1 | Down-regulated by Androgen |
| AF052578 | *Homo sapiens* androgen receptor associated protein 24 (ARA24) | Down-regulated by Androgen |
| X16312 | Human mRNA for phosvitin/casein kinase II beta subunit. | Down-regulated by Androgen |
| H17890 | PCTAIRE protein kinase 3 | Down-regulated by Androgen |
| AA192312 | EST | Down-regulated by Androgen |
| AA043787 | EST | Down-regulated by Androgen |
| AI052020 | EST | Down-regulated by Androgen |
| AB014512 | *Homo sapiens* mRNA for KIAA0612 protein | Down-regulated by Androgen |
| NM_001328 | *Homo sapiens* C-terminal binding protein 1 (CTBP1) mRNA | Down-regulated by Androgen |
| M15919 | Human autoimmune antigen small nuclear ribonucleoprotein E mRNA. | Down-regulated by Androgen |
| AF151813 | *Homo sapiens* CGI-55 protein mRNA, complete cds | Down-regulated by Androgen |
| L41351 | Protease, serine, 8 (prostasin) | Down-regulated by Androgen |
| AF077046 | *Homo sapiens* ganglioside expression factor 2 (GEF-2) homolog | Down-regulated by Androgen |
| U15008 | Small nuclear ribonucleoprotein D2 polypeptide (16.5 kD), AA938995 | Down-regulated by Androgen |
| N62491 | Folate hydrolase (prostate-specific membrane antigen) 1 | Down-regulated by Androgen |
| AI569591 | EST | Down-regulated by Androgen |
| AJ131245 | Secretory protein 24 (SEC24). | Down-regulated by Androgen |
| U90543 | Human butyrophilin (BTF1) mRNA, complete cds. | Down-regulated by Androgen |
| Z47087 | Transcription elongation factor B (SIII), polypeptide 1-like | Down-regulated by Androgen |
| M34539 | FK506-binding protein 1A (12 kD) | Down-regulated by Androgen |
| N43807 | yy19a05.r1 Soares melanocyte 2NbHM *Homo sapiens* cDNA clone | Down-regulated by Androgen |
| U03269 | Human actin capping protein alpha subunit (CapZ) mRNA, complete | Down-regulated by Androgen |
| AI571685 | EST | Down-regulated by Androgen |
| AA010412 | EST | Down-regulated by Androgen |
| L40403 | *Homo sapiens* (clone zap3) mRNA, 3' end of cds. | Down-regulated by Androgen |
| NM_006560 | CUG triplet repeat, RNA-binding protein 1 | Down-regulated by Androgen |
| NM_004713 | Serologically defined colon cancer antigen 1 | Down-regulated by Androgen |
| U36188 | Clathrin-associated/assembly/adaptor protein, medium 1 | Down-regulated by Androgen |
| AB020721 | KIAA0914 gene product | Down-regulated by Androgen |
| T35365 | EST | Down-regulated by Androgen |
| AF029789 | *Homo sapiens* GTPase-activating protein (SIPA1) mRNA, complete cds. | Down-regulated by Androgen |
| AA427857 | EST | Down-regulated by Androgen |
| AA910404 | EST | Down-regulated by Androgen |
| L42379 | Quiescin Q6 (bone-derived growth factor) | Down-regulated by Androgen |
| AL117641 | cDNA DKFZp434L235 | Down-regulated by Androgen |
| AI688119 | EST | Down-regulated by Androgen |
| AA688073 | EST | Down-regulated by Androgen |
| NM_002945 | Replication protein A1 (70 kD) | Down-regulated by Androgen |
| AI797610 | EST | Down-regulated by Androgen |
| AF086095 | *Homo sapiens* full length insert cDNA clone YZ88A07. | Down-regulated by Androgen |
| AF070666 | *Homo sapiens* tissue-type pituitary Kruppel-associated box protein | Down-regulated by Androgen |
| R55128 | Proteasome (prosome, macropain) 26S subunit, non-ATPase, 2 | Down-regulated by Androgen |
| X75621 | Tuberous sclerosis 2 | Down-regulated by Androgen |
| AA019070 | EST | Down-regulated by Androgen |

TABLE 3-continued

Genes Regulated by Androgen: SAGE Data Derived from CPDR SAGE Library

| Accession | Description | Effect of Androgen |
|---|---|---|
| AI089867 | EST | Down-regulated by Androgen |
| NM_001003 | *Homo sapiens* ribosomal protein, large, P1 (RPLP1) mRNA | Down-regulated by Androgen |
| L05093 | Ribosomal protein L18a | Down-regulated by Androgen |
| AA854176 | EST | Down-regulated by Androgen |
| AI929622 | *Homo sapiens* clone 23675 mRNA sequence | Down-regulated by Androgen |
| AI264769 | ESTs, Weakly similar to ORF YDL087c [*S. cerevisiae*] | Down-regulated by Androgen |
| L09159 | Ras homolog gene family, member A, may be androgen regulated? | Down-regulated by Androgen |
| AI143187 | EST | Down-regulated by Androgen |
| H17900 | cDNA DKFZp586H051 (from clone DKFZp586H051) | Down-regulated by Androgen |
| NM_005617 | Ribosomal protein S14 | Down-regulated by Androgen |
| L49506 | Cyclin G2 | Down-regulated by Androgen |
| AA614448 | Regulator of G-protein signalling 5 | Down-regulated by Androgen |
| S83390 | T3 receptor-associating cofactor-1 | Down-regulated by Androgen |
| AA917672 | EST | Down-regulated by Androgen |
| X52151 | Arylsulphatase A | Down-regulated by Androgen |
| U09646 | Carnitine palmitoyltransferase II | Down-regulated by Androgen |
| Z50853 | ATP-dependent protease ClpAP (*E. coli*), proteolytic subunit, human | Down-regulated by Androgen |
| AB023208 | MLL septin-like fusion | Down-regulated by Androgen |
| U92014 | Human clone 121711 defective mariner transposon Hsmar2 mRNA | Down-regulated by Androgen |
| AA878293 | Alpha-1-antichymotrypsin | Down-regulated by Androgen |
| AA554191 | EST | Down-regulated by Androgen |
| M55618 | Hexabrachion (tenascin C, cytotactin) | Down-regulated by Androgen |
| AA027050 | EST | Down-regulated by Androgen |
| AF112472 | *Homo sapiens* calcium/calmodulin-dependent protein kinase II beta | Down-regulated by Androgen |
| AA583866 | EST | Down-regulated by Androgen |
| AA115687 | EST | Down-regulated by Androgen |
| AA043318 | EST | Down-regulated by Androgen |
| U90329 | Poly(rC)-binding protein 2 | Down-regulated by Androgen |
| Y00815 | Protein tyrosine phosphatase, receptor type, F | Down-regulated by Androgen |
| X76013 | *H. sapiens* QRSHs mRNA for glutaminyl-tRNA synthetase. | Down-regulated by Androgen |
| X75861 | Testis enhanced gene transcript | Down-regulated by Androgen |
| AA593078 | *Homo sapiens* PAC clone DJ0167F23 from 7p15 | Down-regulated by Androgen |
| J04058 | Human electron transfer flavoprotein alpha-subunit mRNA | Down-regulated by Androgen |
| AF026292 | *Homo sapiens* chaperonin containing t-complex polypeptide 1, eta | Down-regulated by Androgen |
| AF068754 | *Homo sapiens* heat shock factor binding protein 1 HSBP1 mRNA, | Down-regulated by Androgen |
| NM_000172 | Guanine nucleotide binding protein (G protein), alpha transducing activity polypeptide 1 | Down-regulated by Androgen |
| AI140631 | Hs.1915: folate hydrolase (prostate-specific membrane antigen) 1 | Down-regulated by Androgen |

Bold font indicates known androgen-regulated gene based on Medline Search.

TABLE 4

Potential Prostate Specific/Abundant Genes Derived From NCBI and CPDR SAGE Libraries

| Accession | Description |
|---|---|
| M88700 | Human dopa decarboxylase (DDC) gene, complete cds. |
| W45526 | zc26b04.r1 Soares_senescent_fibroblasts_NbHSF *Homo sapiens* cDNA, Hs.108981: ficolin (collagen/fibrinogen domain-containing) 1, AF201077 NADH: ubiquinone oxidoreductase MLRQ subunit (NDUFA4) mRNA, complete cds with polyA. |
| D55953 | HUM407H12B Clontech human fetal brain polyA+ mRNA (#6535) Homo, Hs.118724: histidine triad nucleotide-binding protein, AJ012499, mRNA activated in tumor suppression, clone TSAP19 with polyA |
| AA082804 | zn41g02.r1 Stratagene endothelial cell 937223 *Homo sapiens* cDNA, Hs.110967: ESTs, Weakly similar to KIAA0762 protein [*H. sapiens*], Hs.5662: guanine nucleotide binding protein (G protein), beta polypeptide 2-like 1 in the sequence no tag |

TABLE 4-continued

Potential Prostate Specific/Abundant Genes Derived From NCBI and CPDR SAGE Libraries

| Accession | Description |
| --- | --- |
| X05332 | Human mRNA for prostate specific antigen.* |
| AI278854 | qo42f01.x1 NCI_CGAP_Lu5 *Homo sapiens* cDNA clone IMAGE: 1911193 3', NM_004537, nucleosome assembly protein 1-like 1 (NAP1L1), tag is at beginning of the gene. |
| W75950 | zd58b02.r1 Soares_fetal_heart_NbHH19W *Homo sapiens* cDNA clone, AF151840, CGI-82 protein mRNA, tag is at 3' end. |
| F02980 | HSC1IC062 normalized infant brain cDNA *Homo sapiens* cDNA clone |
| M99487 | Human prostate-specific membrane antigen (PSM) mRNA, complete cds. |
| AL035304 | *H. sapiens* gene from PAC 295C6, similar to rat PO44. |
| AI088979 | ou86f03.s1 Soares_NSF_F8_9W_OT_PA_P_S1 *Homo sapiens* cDNA clone |
| AF186249 | Homo sapiens six transmembrane epithelial antigen of prostate (STEAP1) mRNA |
| C15801 | C15801 Clontech human aorta polyA+ mRNA (#6572) *Homo sapiens* cDNA |
| L10340 | Human elongation factor-1 alpha (ef-1) mRNA, 3' end. |
| NM_004540 | *Homo sapiens* neural cell adhesion molecule 2 (NCAM2) |
| AA151796 | z139c02.r1 Soares_pregnant_uterus_NbHPU *Homo sapiens* cDNA clone |
| NM_001634 | *Homo sapiens* S-adenosylmethionine decarboxylase 1 (AMD1) |
| NM_005013 | *Homo sapiens* nucleobindin 2 (NUCB2)AL121913 in GenBank htgc database) and 718J7 (Accession number AL035541 |
| AF004828 | *Homo sapiens* rab3-GAP regulatory domain mRNA, complete cds. |
| X60819 X60 | *H. sapiens* DNA for monoamine oxidase type A (14) (partial). |
| AA133972 | z138g12.r1 Soares_pregnant_uterus_NbHPU *Homo sapiens* cDNA clone |
| M69226 | Human monoamine oxidase (MAOA) mRNA, complete cds. |
| AA969141 | op50c11.s1 Soares_NFL_T_GBC_S1 *Homo sapiens* cDNA clone |
| AA523652 | ni64d09.s1 NCI_CGAP_Pr12 *Homo sapiens* cDNA clone IMAGE: 981617, mRNA |
| AF078749 | *Homo sapiens* organic cation transporter 3 (SLC22A3) |
| AA583544 | nf25h10.s1 NCI_CGAP_Pr1 *Homo sapiens* cDNA clone IMAGE: 914851, mRNA |
| AF051894 | *Homo sapiens* 15 kDa selenoprotein mRNA, complete cds. |
| AF165967 | *Homo sapiens* DDP-like protein mRNA |
| X57129 | *H. sapiens* H1.2 gene for histone H1. |
| AA640928 | nr28d08.r1 NCI_CGAP_Pr3 *Homo sapiens* cDNA clone IMAGE: 1169295, mRNA |
| U41766 | Human metalloprotease/disintegrin/cysteine-rich protein precursor |
| AF023676 | *Homo sapiens* lamin B receptor homolog TM7SF2 (TM7SF2) mRNA, |
| U10691 | Human MAGE-6 antigen (MAGE6) gene, complete cds. |
| M22976 | Human cytochrome b5 mRNA, 3' end. |
| L14778 | Human calmodulin-dependent protein phosphatase catalytic subunit |
| AF071538 | Homo sapiens Ets transcription factor PDEF (PDEF) mRNA, complete |
| U39840 | Human hepatocyte nuclear factor-3 alpha (HNF-3 alpha) mRNA, |
| AA532511 | nj54d03.s1 NCI_CGAP_Pr9 *Homo sapiens* cDNA clone IMAGE: 996293, mRNA |
| X07166 | Human mRNA for enkephalinase (EC 3.4.24.11). |
| M96684 | *H. sapiens* Pur (pur-alpha) mRNA, complete cds. |
| AI204040 | qe77f05.x1 Soares_fetal_lung_NbHL19W *Homo sapiens* cDNA clone |
| AA577923 | nl20a01.s1 NCI_CGAP_HSC1 *Homo sapiens* cDNA clone IMAGE: 1041192, |
| AA569633 | nm38h09.s1 NCI_CGAP_Pr4.1 *Homo sapiens* cDNA clone IMAGE: 1062497, |
| U65011 | Human preferentially expressed antigen of melanoma (PRAME) mRNA, |
| U21910 | Human basic transcription factor BTF2p44 mRNA, 3' end, partial cds. |
| AA633187 | nq07c12.s1 NCI_CGAP_Lu1 *Homo sapiens* cDNA clone IMAGE: 1143190 3' |
| AF000993 | *Homo sapiens* ubiquitous TPR motif, X isoform (UTX) mRNA, |
| W76105 | zd65b04.r1 Soares_fetal_heart_NbHH19W *Homo sapiens* cDNA clone |
| H39906 | yo54a07.r1 Soares breast 3NbHBst *Homo sapiens* cDNA clone |
| AA971717 | op95c11.s1 Soares_Lu5 *Homo sapiens* cDNA clone IMAGE: 1584596 3', |
| M68891 | Human GATA-binding protein (GATA2) mRNA, complete cds. |
| AA310157 | EST181013 Jurkat T-cells V *Homo sapiens* cDNA 5' end, mRNA sequence. |
| X00948 | Human mRNA for prepro-relaxin H2. |
| AB018330 | *Homo sapiens* mRNA for KIAA0787 protein, partial cds. |
| AA890637 | ak11e11.s1 Soares_parathyroid_tumor_NbHPA *Homo sapiens* cDNA clone |
| M64929 J05 | Human protein phosphatase 2A alpha subunit mRNA, complete cds. |
| W24341 | zb81h12.r1 Soares_senescent_fibroblasts_NbHSF *Homo sapiens* cDNA |
| AA974479 | od58b03.s1 NCI_CGAP_GCB1 *Homo sapiens* cDNA clone IMAGE: 1372109 3' |
| R31644 | yh69e05.r1 Soares placenta Nb2HP *Homo sapiens* cDNA clone |
| AA573246 | nm52c02.s1 NCI_CGAP_Br2 *Homo sapiens* cDNA clone IMAGE: 1071842 3', |
| AA507635 | ng84b02.s1 NCI_CGAP_Pr6 *Homo sapiens* cDNA clone IMAGE: 941451, mRNA |
| gb\|AF008915 | *Homo sapiens* EVI5 homolog mRNA |
| AL049987 | *Homo sapiens* mRNA; cDNA DKFZp564F112 (from clone DKFZp564F112). |
| U81599 | Homo sapiens homeodomain protein HOXB13 mRNA |
| AA641596 | nr20f05.s1 NCI_CGAP_Pr2 *Homo sapiens* cDNA clone IMAGE: 1168545, mRNA |
| D84295 | Human mRNA for possible protein TPRDII |
| R13859 | yf65d08.r1 Soares infant brain 1NIB *Homo sapiens* cDNA clone |
| M34840 | Human prostatic acid phosphatase mRNA, complete cds. |
| AA572913 | nm42f12.s1 NCI_CGAP_Pr4.1 *Homo sapiens* cDNA clone IMAGE: 1062863, |
| AA094460 | cp0378.seq.F Human fetal heart, Lambda ZAP Express *Homo sapiens* |
| AF031166 | *Homo sapiens* SRp46 splicing factor retropseudogene mRNA. |
| AA625147 | af70c07.r1 Soares_NhHMPu_S1 *Homo sapiens* cDNA clone IMAGE: 1047372 |
| T39510 | ya06h07.r1 Stratagene placenta (#937225) *Homo sapiens* cDNA clone |
| R35034 | yg60h03.r1 Soares infant brain 1NIB *Homo sapiens* cDNA clone |
| AI003674 | zg01c04.s1 Soares_pineal_gland_N3HPG *Homo sapiens* cDNA clone |

TABLE 4-continued

Potential Prostate Specific/Abundant Genes Derived From NCBI and CPDR SAGE Libraries

| Accession | Description |
| --- | --- |
| AJ003636 | AJ003636 Selected chromosome 21 cDNA library *Homo sapiens* cDNA |
| AA601385 | no16d12.s1 NCI_CGAP_Phe1 *Homo sapiens* cDNA clone IMAGE: 1100855 3', |
| AF191339 | *Homo sapiens* anaphase-promoting complex subunit 5 (APC5) |
| AA431822 | zw79d02.r1 Soares_testis_NHT *Homo sapiens* cDNA clone IMAGE: 782403 |
| NM_003909 | *Homo sapiens* copine III (CPNE3) |
| AA484004 | ne73f04.s1 NCI_CGAP_Ew1 *Homo sapiens* cDNA clone IMAGE: 909919 |
| AA535774 | nj78f08.s1 NCI_CGAP_Pr10 *Homo sapiens* cDNA clone IMAGE: 998631, mRNA |
| NM_000944.1 | *Homo sapiens* protein phosphatase 3 (formerly 2B) |
| AA702811 | zi90c11.s1 Soares_fetal_liver_spleen_1NFLS_S1 *Homo sapiens* cDNA |
| X95073 | *H. sapiens* mRNA for translin associated protein X. |
| AA029039 | zk12b07.s1 Soares_pregnant_uterus_NbHPU *Homo sapiens* cDNA clone |
| AF032887 | *Homo sapiens* forkhead (FKHRL1P1) pseudogene |
| N46609 | yy48h08.r1 Soares_multiple_sclerosis_2NbHMSP *Homo sapiens* cDNA |
| U58855 | *Homo sapiens* soluble guanylate cyclase large subunit (GC-S-alpha-1) |
| AA255486 | zr83d03.s1 Soares_NhHMPu_S1 *Homo sapiens* cDNA clone IMAGE: 682277 |
| AA128153 | zl15c06.s1 Soares_pregnant_uterus_NbHPU *Homo sapiens* cDNA clone |
| AA016039 | ze31c05.s1 Soares retina N2b4HR *Homo sapiens* cDNA clone |
| R88520 | ym91e09.s1 Soares adult brain N2b4HB55Y *Homo sapiens* cDNA clone |
| M26624 | Human CALLA/NEP gene encoding neutral endopeptidase, exon 20. |
| AA026997 | ze99e01.r1 Soares_fetal_heart_NbHH19W *Homo sapiens* cDNA clone |
| W48775 | zc44b08.r1 Soares_senescent_fibroblasts_NbHSF *Homo sapiens* cDNA |
| AA074407 | zm15c08.r1 Stratagene pancreas (#937208) *Homo sapiens* cDNA clone |
| L13972 | *Homo sapiens* beta-galactoside alpha-2,3-sialyltransferase (SIAT4A) |
| D14661 | Human mRNA for KIAA0105 gene, complete cds. |
| AA115452 | zk89a08.r1 Soares_pregnant_uterus_NbHPU *Homo sapiens* cDNA clone |
| AA495742 | zw04b12.r1 Soares_NhHMPu_S1 *Homo sapiens* cDNA clone IMAGE: 768287 5' |
| R13416 | yf75h09.r1 Soares infant brain 1NIB *Homo sapiens* cDNA clone |
| AA046369 | zk77h07.r1 Soares_pregnant_uterus_NbHPU *Homo sapiens* cDNA clone |
| T35440 | EST85129 Human Lung *Homo sapiens* cDNA 5' end similar to None, mRNA |
| AI075860 | oz25b05.x1 Soares_total_fetus_Nb2HF8_9w *Homo sapiens* cDNA clone |
| W56437 | zc57g05.r1 Soares_parathyroid_tumor_NbHPA *Homo sapiens* cDNA clone |
| AI583880 | tt70b02.x1 NCI_CGAP_HSC3 *Homo sapiens* cDNA clone IMAGE: 2246091 3', |
| D85181 | *Homo sapiens* mRNA for fungal sterol-C5-desaturase homolog, complete |
| AF105714 | *Homo sapiens* protein kinase PITSLRE (CDC2L2) gene, exon 3. |
| AA401802 | zt60c12.r1 Soares_testis_NHT *Homo sapiens* cDNA clone IMAGE: 726742 |
| AB002301 | Human mRNA for KIAA0303 gene, partial cds. |
| U75667 | Human arginase II mRNA, complete cds. |
| AA585183 | JTH089 HTCDL1 *Homo sapiens* cDNA 5'/3', mRNA sequence. |
| AF191771 | *Homo sapiens* CED-6 protein (CED-6) mRNA |
| AA650252 | ns93g05.s1 NCI_CGAP_Pr3 *Homo sapiens* cDNA clone IMAGE: 1191224, mRNA |
| R64618 | yi19b09.r1 Soares placenta Nb2HP *Homo sapiens* cDNA clone |
| N24627 | yx89a09.s1 Soares melanocyte 2NbHM *Homo sapiens* cDNA clone |
| AB028951 | *Homo sapiens* mRNA for KIAA1028 protein |
| N75608 | yw37a07.r1 Morton Fetal Cochlea *Homo sapiens* cDNA clone |
| N53899 | yy98e03.r1 Soares_multiple_sclerosis_2NbHMSP *Homo sapiens* cDNA |
| N46696 | yy50f07.r1 Soares_multiple_sclerosis_2NbHMSP *Homo sapiens* cDNA |
| AA419522 | zv03d05.r1 Soares_NhHMPu_S1 *Homo sapiens* cDNA clone IMAGE: 752553 |
| M61906 | Human P13-kinase associated p85 mRNA sequence. |
| C16570 | C16570 Clontech human aorta polyA+ mRNA (#6572) *Homo sapiens* cDNA |
| X63105 | *H. sapiens* tpr mRNA. |
| AA315855 | EST187656 Colon carcinoma (HCC) cell line II *Homo sapiens* cDNA 5' |
| L18920 | Human MAGE-2 gene exons 1-4, complete cds. |
| M25161 | Human Na,K-ATPase beta subunit (ATP1B) gene |
| AA164865 | zq41g07.r1 Stratagene hNT neuron (#937233) *Homo sapiens* cDNA clone |
| N40094 | yx98g07.r1 Soares melanocyte 2NbHM *Homo sapiens* cDNA clone |
| N98940 | yy71a07.r1 Soares_multiple_sclerosis_2NbHMSP *Homo sapiens* cDNA |
| AF049907 | *Homo sapiens* zinc finger transcription factor (ZNF-X) mRNA, |
| M78806 | EST00954 Hippocampus, Stratagene (cat. #936205) *Homo sapiens* cDNA |
| AA040819 | zk47b03.r1 Soares_pregnant_uterus_NbHPU *Homo sapiens* cDNA clone |
| C15445 | C15445 Clontech human aorta polyA+ mRNA (#6572) *Homo sapiens* cDNA |
| AB018309 | *Homo sapiens* mRNA for KIAA0766 protein, complete cds. |
| AJ011497 | *Homo sapiens* mRNA for Claudin-7. |
| X00949 | Human mRNA for prepro-relaxin H1. |
| AA418633 | zv93d09.r1 Soares_NhHMPu_S1 *Homo sapiens* cDNA clone IMAGE: 767345 5' |
| AI146806 | qb83h04.x1 Soares_fetal_heart_NbHH19W *Homo sapiens* cDNA clone |
| X82942 | *H. sapiens* satellite 3 DNA. |
| AA456383 | aa14f03.r1 Soares_NhHMPu_S1 *Homo sapiens* cDNA clone IMAGE: 813245 |
| AA019341 | ze57e04.s1 Soares retina N2b4HR *Homo sapiens* cDNA clone |
| AB027466 | *Homo sapiens* SPON2 mRNA for spondin 2 |
| AF038170 | *Homo sapiens* clone 23817 mRNA sequence. |
| NM_000240 | *Homo sapiens* monoamine oxidase A (MAOA) |
| N34126 | yx76c01.r1 Soares melanocyte 2NbHM *Homo sapiens* cDNA clone |
| N41339 | yw68g06.r1 Soares_placenta_8to9weeks_2NbHP8to9W *Homo sapiens* cDNA |
| R34783 | yh87b05.r1 Soares placenta Nb2HP *Homo sapiens* cDNA clone |
| N75858 | yw32a03.r1 Morton Fetal Cochlea *Homo sapiens* cDNA clone |

TABLE 4-continued

Potential Prostate Specific/Abundant Genes Derived From NCBI and CPDR SAGE Libraries

| Accession | Description |
| --- | --- |
| AA633887 | ac32h04.s1 Stratagene hNT neuron (#937233) Homo sapiens cDNA clone |
| N53723 | yz06d03.r1 Soares_multiple_sclerosis_2NbHMSP Homo sapiens cDNA |
| AI187365 | qf29b12.x1 Soares_testis_NHT Homo sapiens cDNA clone IMAGE: 1751423 |

Genes in bold type are known prostate-specific genes.

TABLE 5

Genes/ESTs as Defined by Publications:
Including Androgen Signaling, Prostate Specificity, Prostate Cancer Association, and
Nuclear Receptors/Regulators with Potential Interaction with Androgen Receptor

| Cluster ID | Gene Name | Description | | References |
| --- | --- | --- | --- | --- |
| Hs.81988 | DOC-2 | deliion of ovarian carcinoma 2 | Up-regulated by Androgen Ablation | Endocrinology, 139,3542,98 |
| Hs.155389 | RAR a | | Up-regulated by Androgen Ablation | endocrinology, 138,553,97 |
| Hs.12601 | AS3 | DNA binding protein | Up-regulated by Androgen Ablation | J Steroid Biochem Mol Biol 68,41,99 |
| Hs.181426 | EST | | Up-regulated by Androgen Ablation | |
| Hs.2391 | apical protein | | Up-regulated by Androgen Ablation | |
| Hs.109530 | KGF/FGF7 | keratinocyte growth factor | Up-regulated by Androgen | BBRC 220,858,96, Can Res, 54,5474,94 |
| Hs.1104 | TGF beta 1 | | Up-regulated by Androgen | Endocrinology, 137,99,96, Endocrinology, 139,378,98 |
| Hs.75525 | Calreticulin | Calreticulin | Up-regulated by Androgen | Can Res 59,1896,99 |
| Hs.78888 | DBI/ACBP | Diazepam-binding inhibitor/acyl-CoA binding Protein | Up-regulated by Androgen | JBC, 237,19938,98 |
| Hs.41569 | Phosphatidic acid phosphatase type 2a isozyme | | Up-regulated by Androgen | JBC, 273,4660,98 |
| Hs.83190 | Fatty acid synthase | | Up-regulated by Androgen | Can Res, 57,1086,97 |
| Hs.99915 | Androgen Receptor | | Up-regulated by Androgen | Steroids 9,531,96 |
| Hs.2387 | prostate-restricted transglutaminase | | Up-regulated by Androgen | Biochem J 315,901,96 |
| Hs.78996 | PCNA | proliferating cell nuclear antigen | Up-regulated by Androgen | Can Res 56,1539,96 |
| Hs.74456 | GAPDH | | Up-regulated by Androgen | Can Res 55,4234,95 |
| Hs.82004 | E cadherin | | Up-regulated by Androgen | BBRC, 212,624,95 |
| Hs.57710 | AIGF | Androgen-induced growth factor | Up-regulated by Androgen | FEBS lett 363,226,95 |
| Hs.118618 | MIC2 | humanpseudoautosomal gene? | Up-regulated by Androgen | Mol Carcinog, 23,13,98 |
| Hs.18420 | Talin | cytoskeletal protein | Up-regulated by Androgen | FEBS lett 434,66,98 |
| Hs.54502 | clathrin heavy chain | | Up-regulated by Androgen | Endocrinology, 139,2111,98 |
| Hs.73919 | clathrin light chain b | | Up-regulated by Androgen | Endocrinology, 139,2111,98 |
| Hs.76506 | L-plastin | ESTs, Moderately similar to L-PLASTIN [H. sapiens] | Up-regulated by Androgen | Am J Pathol, 150,2009,97 |
| Hs.82173 | EGR alpha | TGFB inducible early growth response | Up-regulated by Androgen | Mol Endocrinol, 9,1610,95 |
| ND | FGF10 | | Up-regulated by Androgen | JBC, 274,12827,99 |
| Hs.107169 | IGFBP5 | | Up-regulated by Androgen | Endocrinology, 140,2372,99 |
| Hs.179665 | p21 | | Up-regulated by Androgen | Mol Endocrinol, 13,376,99 |
| Hs.51117 | BMP-7 | | Up-regulated by Androgen | Prostate, 37,236,98 |
| Hs.73793 | VEGF | vascular endothelial growth factor | Up-regulated by Androgen | Endocrinol, 139,4672,98, BBRC, 251,287,98 |
| Hs.166 | SREBPs | sterol regulatory element binding transcription factor1 | Up-regulated by Androgen | J Steroid Biochem Mol Biol, 65,191,98 |
| Hs.116577 | PDF | prostate differentiation factor | Up-regulated by Androgen | JBC, 273,13760,98 |
| Hs.1905 | prolactin | Prolactin | Up-regulated by Androgen | FEBS J, 11,1297,97 |
| Hs.19192 | CDK2 | | Up-regulated by Androgen | Can Res, 57,4511,97 |

TABLE 5-continued

Genes/ESTs as Defined by Publications:
Including Androgen Signaling, Prostate Specificity, Prostate Cancer Association, and
Nuclear Receptors/Regulators with Potential Interaction with Androgen Receptor

| Cluster ID | Gene Name | Description | References |
|---|---|---|---|
| Hs.95577 | CDK4 | cyclin-dependent kinase 4 | Up-regulated by Androgen | Can Res, 57,4511,97 |
| Hs.183596 | UGT2B17 | uridine diphosphoglucronosyl transferase | Up-regulated by Androgen | Endocrinology, 138,2998,97 |
| Hs.150207 | UGT2B15 | UDP-glucronosyltransferase 2B15 | Up-regulated by Androgen | Can Res 57,4075,97 |
| ND | prostate binding protein C2A (RAT) | | Up-regulated by Androgen | PNAS, 94,12999,97 |
| ND | Probasin (RAT) | | Up-regulated by Androgen | PNAS, 94,12999,97 |
| Hs.7719 | prostatein C3 (RAT) | | Up-regulated by Androgen | PNAS, 94,12999,97 |
| ND | Cystatin related protein 1 (RAT) | | Up-regulated by Androgen | PNAS, 94,12999,97 |
| ND | Cystatin related protein 2 (RAT) | | Up-regulated by Androgen | PNAS, 94,12999,97 |
| Hs.394 | Adrenomedulin (RAT) | | Up-regulated by Androgen | PNAS, 94,12999,97 |
| Hs.77393 | farnesyl diphosphate synthase (farnesyl pyrophosphate synthetase, dimethylallyltranstransferase) | | Up-regulated by Androgen | PNAS, 94,12999,97 |
| Hs.153468 | LDL receptor (Rat) | | Up-regulated by Androgen | PNAS, 94,12999,97 |
| N.D. | Hysto-blood group A transferase (RAT) | | Up-regulated by Androgen | PNAS, 94,12999,97 |
| Hs.196604 | Sex limited protein (RAT) slp | | Up-regulated by Androgen | PNAS, 94,12999,97 |
| ND | prostatic spermine binding protein(RAT) | | Up-regulated by Androgen | Mol Cell Endocrinol, 108,R1,95 |
| Hs.76353 | Protein C Inhibitor | | Up-regulated by Androgen | FEBS lett, 492,263,98 |
| Hs.203602 | enolase alpha | | Up-regulated by Androgen | Can Res, 58,5718,98 |
| Hs.169476 | tubulin alpha | | Up-regulated by Androgen | Can Res, 58,5718,98 |
| Hs.184572 | Cdk1 | | Up-regulated by Androgen | Can Res, 58,5718,98 |
| Hs.107528 | EST | EST similar to androgen-regulated protein FAR-17 | Up-regulated by Androgen | |
| Hs.28309 | UDP-glucose dehydrogenase | | Up-regulated by Androgen | Endocrinology, 140.10.4486.(99) |
| Hs.194270 | secretory component gene | | Up-regulated by Androgen | Mol endocrinol, 13,9,1558,(99) |
| Hs.76136 | Thioredoxin | | Up-regulated by Androgen | J steroid Biochem Mol Biol, 68, 5–6, 203, (99) |
| Hs.3561 | p27 Kip1 | cyclin-dependent kinase inhibitor 1B (p27, Kip1) | Up-regulated by Androgen | Mol Endocrinol, 12,941,98 |
| Hs.1867 | progastricsin (pepsinogen C) | | Up-regulated by Androgen | J.B.C. 271,15175,(99) |
| Hs.97411 | hamster Androgen-dependent Expressed Protein like protein gene | | Up-regulated by Androgen | Genebank |
| Hs.155140 | Protein kinase CK2 | casein kinase 2, alpha 1 polypeptide | Translocated by Androgen | Can Res 59,1146,99 |
| IMAGE.953262 | DD3 | | Prostate Specific | Eur Urol, 35,408,99 |
| Hs.218366 | Prostase | | Prostate Specific | PNAS, 96,3114,99 |
| Hs.20166 | PSCA | prostate stem cell antigen | Prostate Specific | PNAS, 95,1735,98 |
| Hs.171995 | PSA | kallikrein 3, (prostate specific antigen) | Prostate Specific | PNAS, 95,300,98, DNA Cell Biol, 16,627,97 |
| Hs.183752 | PSSPP | prostate-secreted seminal plasma protein, nc50a10, microsemnoprotein beta, PSP94 | Prostate Specific | PNAS, 95,300,98 |
| Hs.1852 | PAP | prostatic acid phosphatase | Prostate Specific | PNAS, 95,300,98 |
| Hs.52871 | SYT | | Prostate Specific | PNAS, 95,300,98 |
| Hs.158309 | Homeobox HOX D13 | | Prostate Specific | PNAS, 95,300,98 |
| Hs.1968 | Semenogelin 1 | | Prostate Specific | PNAS, 95,300,98 |
| Hs.76240 | Adenylate kinase isoenzyme1 | adenylate kinase 1 | Prostate Specific | PNAS, 95,300,98 |
| Hs.184376 | SNAP23 | | Prostate Specific | PNAS, 95,300,98 |

TABLE 5-continued

Genes/ESTs as Defined by Publications:
Including Androgen Signaling, Prostate Specificity, Prostate Cancer Association, and
Nuclear Receptors/Regulators with Potential Interaction with Androgen Receptor

| Cluster ID | Gene Name | Description | | References |
|---|---|---|---|---|
| Hs.82186 | ERBB-3 receptor protein-tyrosin kinase | | Prostate Specific | PNAS, 95,300,98 |
| Hs.180016 | Semenogelin 2 | | Prostate Specific | |
| Hs.1915 | PSMA | folate hydrolase (prostate-specific membrane antigen) 1 | Prostate Specific | |
| Hs.181350 | KLK2 | | Prostate Specific | |
| Hs.73189 | NKX3.1 | | Prostate Specific | |
| IMAGE: 565779 | HPARJ1 | | Prostate Specific | |
| Hs.76053 | p68 RNA helicase | | Potential interaction with AR | MCB, 19,5363,(99) |
| Hs.111323 | ARIP3 | | Potential interaction with AR | JBC, 274,3700,99 |
| Hs.25511 | ARA54 | | Potential interaction with AR | JBC274,8319,99 |
| Hs.28719 | ARA55 | | Potential interaction with AR | JBC, 274,8570,99 |
| HS.999908 | ARA70 | | Potential interaction with AR | PNAS, 93,5517,96 |
| Hs.29131 | TIF2 | transcriptional intermediary factor 2 | Potential interaction with AR | EMBO, 15,3667,96, EMBO, 17,507,98 |
| Hs.66394 | SNURF | ring finger protein 4 | Potential interaction with AR | MCB, 18,5128,98 |
| Hs.75770 | RB | retinoblastoma 1 (including osteosarcoma) | Potential interaction with AR | |
| Hs.74002 | SRC-1 | steroid receptor coactivator 1 | Potential interaction with AR | |
| Hs.155017 | RIP140 | nuclear receptor interacting protein 1 | Potential interaction with AR | EMBO, 14,3741,95, Mol Endocrinol, 12,864,98 |
| Hs.23598 | CBP | CREB binding protein (Rubinstein-Taybi syndrome) | Potential interaction with AR | |
| Hs.25272 | p300 | E1A binding protein p300 | Potential interaction with AR | |
| Hs.78465 | c-JUN | | Potential interaction with AR | |
| Hs.199041 | ACTR | AIBI, mouse GRIPI, pCIP | Potential interaction with AR | M.C.B, 17,2735,97, PNAS, 93,4948,96 |
| Hs.6364 | TIP60 | Human tat interactive protein mRNA, complete cds | Potential interaction with AR | JBC, 274,17599,99 |
| Hs.32587 | SRA | | Potential interaction with AR | Cell, 97,17,99 |
| Hs.155302 | PCAF | | Potential interaction with AR | |
| Hs.10842 | ARA24 | | Potential interaction with AR | |
| Hs.41714 | BAG-1L | | Potential interaction with AR | JBC, 237,11660,98 |
| Hs.82646 | dnaJ, HSP40 | DNAJ PROTEIN HOMOLOG 1 | Potential interaction with AR | |
| Hs.43697 | ERM | ets variant gene 5 (ets-related molecule) | Potential interaction with AR | JBC, 271,23907,96 |
| Hs.75772 | GR | | Potential interaction with AR | JBC, 272,14087,97 |
| Hs.77152 | MCM7 | | Potential interaction with AR | |
| ND | NJ | | Potential interaction with AR | |
| ND | RAF | | Potential interaction with AR | JBC, 269,20622,94 |
| ND | TFIIF | | Potential interaction with AR | PNAS, 94,8485,97 |
| Hs.90093 | hsp70 | | Potential interaction with AR | |
| Hs.206650 | hsp90 | | Potential interaction with AR | |
| Hs.848 | hsp56(FKBP52, FKBP59, HBI)) | | Potential interaction with AR | |
| Hs.143482 | Cyp40(cyclophilin40) | | Potential interaction with AR | |
| | p23 | | Potential interaction with AR | |
| Hs.84285 | ubiquitin-conjugating enzyme | | Potential Interaction with AR | J.B.C. 274,19441(99) |
| Hs.182237 | POU domain, class 2, transcr | | Potential interaction with AR | |
| Hs.1101 | POU domain, class 2, transcr | | Potential interaction with AR | |
| Hs.2815 | POU domain, class 6, transcr | | Potential interaction with AR | |
| IMAGE: 1419981 | | | Potential interaction with AR | |
| Hs.227639 | ARA160 | | Potential interaction with AR | JBC, 274,22373(99) |
| Hs.83623 | CAR-beta | Xist locus | Nuclear receptor gene family | |
| Hs.2905 | PR | | Nuclear receptor gene family | |
| Hs.1790 | MR | mineralocorticoid receptor (aldosterone receptor) | Nuclear receptor gene family | |
| Hs.1657 | ER alpha | | Nuclear receptor gene family | |
| Hs.103504 | ER beta | | Nuclear receptor gene family | |

TABLE 5-continued

Genes/ESTs as Defined by Publications:
Including Androgen Signaling, Prostate Specificity, Prostate Cancer Association, and
Nuclear Receptors/Regulators with Potential Interaction with Androgen Receptor

| Cluster ID | Gene Name | | Description | References |
|---|---|---|---|---|
| Hs.110849 | ERR1 | | Nuclear receptor gene family | |
| Hs.194667 | ERR2 | | Nuclear receptor gene family | |
| Hs.724 | TR a | thyroid hormone receptor, alpha (avian erythroblastic leukemia viral (v-erb-a) oncogene homolog) | Nuclear receptor gene family | |
| Hs.121503 | TR b | | Nuclear receptor gene family | |
| Hs.171495 | RAR b | retinoic acid receptor, beta | Nuclear receptor gene family | |
| Hs.1497 | RAR g | retinoic acid receptor, gamma | Nuclear receptor gene family | |
| Hs.998 | PPAR a | | Nuclear receptor gene family | |
| Hs.106415 | PPAR b | Human peroxisome proliferator activated receptor mRNA, complete cds | Nuclear receptor gene family | |
| Hs.100724 | PPAR g | peroxisome proliferative activated receptor, gamma | Nuclear receptor gene family | |
| Hs.100221 | LXR b | | Nuclear receptor gene family | |
| Hs.81336 | LXR a | liver X receptor, alpha | Nuclear receptor gene family | |
| Hs.171683 | FXR | farnesoid X-activated receptor | Nuclear receptor gene family | |
| Hs.2062 | VDR | vitamin D (1,25-dihydroxyvitamin D3) receptor | Nuclear receptor gene family | |
| Hs.118138 | PXR | | Nuclear receptor gene family | |
| ND | SXR | | Nuclear receptor gene family | |
| ND | BXR | | Nuclear receptor gene family | |
| ND CAR b? | CAR a | | Nuclear receptor gene family | |
| Hs.196601 | RXRA | | Nuclear receptor gene family | |
| Hs.79372 | RXRB | Human retinoid X receptor beta (RXR-beta) mRNA, complete cds | Nuclear receptor gene family | |
| Hs.194730?TR1? | EAR1 | | Nuclear receptor gene family | |
| Hs.204704 | EAR1 beta | | Nuclear receptor gene family | |
| | E75 | | Nuclear receptor gene family | |
| Hs.2156 | ROR alpha | | Nuclear receptor gene family | |
| Hs.198481 | ROR beta | | Nuclear receptor gene family | |
| Hs.133314 | ROR gammma | | Nuclear receptor gene family | |
| Hs.100221 | NER1 | | Nuclear receptor gene family | |
| Hs.54424 | HNF4A | | Nuclear receptor gene family | |
| Hs.202659 | HNF4G | | Nuclear receptor gene family | |
| Hs.108301 | TR2 | | Nuclear receptor gene family | |
| Hs.520 | TR4 | | Nuclear receptor gene family | |
| Hs.144630 | COUP-TF1 | | Nuclear receptor gene family | |
| Hs.1255 | COUP-TF2 | | Nuclear receptor gene family | |
| Hs.155286 | EAR2 | | Nuclear receptor gene family | |
| Hs.1119 | TR3 | hormone receptor (growth factor-inducible nuclear protein N10) | Nuclear receptor gene family | |
| Hs.82120 | NURR1 | IMMEDIATE-EARLY RESPONSE PROTEIN NOT | Nuclear receptor gene family | |
| Hs.97196 | SF1 | | Nuclear receptor gene family | |
| Hs.183123 | FTF | fetoprotein-alpha 1 (AFP) transcription factor | Nuclear receptor gene family | |
| Hs.46433 | DAX1 | | Nuclear receptor gene family | |
| Hs.11930 | SHP | *Homo sapiens* nuclear hormone receptor (shp) gene, 3' end of cds | Nuclear receptor gene family | |

TABLE 5-continued

Genes/ESTs as Defined by Publications:
Including Androgen Signaling, Prostate Specificity, Prostate Cancer Association, and
Nuclear Receptors/Regulators with Potential Interaction with Androgen Receptor

| Cluster ID | Gene Name | | Description | References |
|---|---|---|---|---|
| Hs.83623, IMAGE 1761923, or 1868028, or 1563505, or 1654096 | CAR-beta | | Nuclear receptor gene family | |
| Hs.199078 | Sin3 | | Nuclear receptor co-repressor complex | Nature, 387,43,97, Nature, 387,49,97 |
| Hs.120980 | SMRT | | Nuclear receptor co-repressor complex | Nature, 377,454,95 |
| Hs.144904 | N-CoR | | Nuclear receptor co-repressor complex | Nature, 377,297,95 |
| Hs.188055 | highly homologue gene to N-CoR in prostate and testis | | Nuclear receptor co-repressor complex | |
| Hs.180686 | E6-AP | Angelman syndrome associated protein | Nuclear receptor co-activator complex | MCB, 19,1182,99 |
| Hs.199211? Hs.198296? | hBRM | ESTs, Highly similar to HOMEOTIC GENE REGULATOR [*Drosophila melanogaster*] | Nuclear receptor co-activator complex | |
| Hs.78202 | hBRG1 | | Nuclear receptor co-activator complex | |
| Hs.11861 | TRAP240 | DRIP250, ARCp250 | Nuclear receptor co-activator complex | Mol Cell, 3,361,99 |
| Hs.85313 | TRAP230 | ARCp240, DRIP240 | Nuclear receptor co-activator complex | Mol Cell, 3,361,99 |
| Hs.15589 | TRAP220 | RB18A, PBP, CRSP200, TRIP2, ARCp205, DRIP205 | Nuclear receptor co-activator complex | |
| Hs.21586 | TRAP170 | RGR, CRSP150, DRIP150, ARCp150chromosomeX | Nuclear receptor co-activator complex | |
| Hs.108319 | TRAP150 | ESTs | Nuclear receptor co-activator complex | Mol Cell, 3,361,99 |
| Hs.193017 | CRSP133 | ARCp130, DRIP130 | Nuclear receptor co-activator complex | Nature, 397,6718,99 |
| Hs.23106 | TRAP100 | ARCp100, DRIP100, | Nuclear receptor co-activator complex | |
| ND | DRIP97 | TRAP97 | Nuclear receptor co-activator complex | |
| Hs.24441 | TRAP95 | ESTs | Nuclear receptor co-activator complex | Mol Cell, 3,361,99 |
| ND | TRAP93 | | Nuclear receptor co-activator complex | |
| Hs.31659 | DRIP92 | ARCp92? | Nuclear receptor co-activator complex | |
| Hs.22630 | TRAP80 | ARCp77, CRSP77, DRIP80(77)? | Nuclear receptor co-activator complex | Mol Cell, 3,361,99 |
| Hs.204045 | ARCp70 | CRSP70, DRIP70 | Nuclear receptor co-activator complex | |
| ND | ARCp42 | | Nuclear receptor co-activator complex | |
| ND | ARCp36 | | Nuclear receptor co-activator complex | |
| Hs.184947 | MED6 | ARCp33 | Nuclear receptor co-activator complex | Mol Cell, 3,97,99 |
| Hs.7558 | MED7 | CRSP33, ARCp34, DRIP36 | Nuclear receptor co-activator complex | Nature, 397,6718,99 |
| ND | ARCp32 | | Nuclear receptor co-activator complex | |
| ND | SRB10 | | Nuclear receptor co-activator complex | |
| ND | SRB11 | | Nuclear receptor co-activator complex | |
| ND | MED10 | NUT2 | Nuclear receptor co-activator complex | |
| Hs.27289 | SOH1 | (yeast?) | Nuclear receptor co-activator complex | Mol Cell, 3,97,99 |
| ND | p26 | | Nuclear receptor co-activator complex | |
| ND | p28 | | Nuclear receptor co-activator complex | |
| ND | p36 | | Nuclear receptor co-activator complex | |
| ND | p37 | | Nuclear receptor co-activator complex | |
| ND but 2 IMAGE clones | TRFP | human homologue of *Drosophila* TRF proximal protein | Nuclear receptor co-activator complex | |
| ND | VDR interacting subunit | 180 kDa, HAT activity | Nuclear receptor co-activator complex | Genes Dev, 12,1787,98 |
| Hs.143696, or IMAGE: 2371696 ? | Coactivator associated methyltransferase I | | Nuclear receptor co-activator complex | Science, 284,2174,99 |
| Hs.79387 | SUG1 | TRIP1 | Nuclear receptor co-activator complex | EMBO, 15,110,96 |
| ND | TRUP | | Nuclear receptor co-activator complex | PNAS, 92,9525,95 |
| Hs.28166 | CRSP34 | | Nuclear receptor co-activator complex | Nature, 397,6718,99 |
| Hs.63667 | transcriptional adaptor 3 (A | | Nuclear receptor co-activator complex | |
| Hs.196725 | ESTs, Highly similar to P300 | | Nuclear receptor co-activator complex | |
| Hs.131846 | PCAF associated factor 65 al | | Nuclear receptor co-activator complex | |
| Hs.155635 | ESTs, Moderately similar toPCAF associated factor 65 beta | | Nuclear receptor co-activator complex | |

TABLE 5-continued

Genes/ESTs as Defined by Publications:
Including Androgen Signaling, Prostate Specificity, Prostate Cancer Association, and
Nuclear Receptors/Regulators with Potential Interaction with Androgen Receptor

| Cluster ID | Gene Name | | Description | References |
|---|---|---|---|---|
| Hs.26782 | PCAF associated factor 65 beta | | Nuclear receptor co-activator complex | |
| Hs.118910 | tumor suscitibility protein 101 | | Modifying AR function | Cancer 15,86,689,(99) |
| Hs.82932 | Cyclin D1 | cyclin D1 (PRAD1: parathyroid adenomatosis I) | Modifying AR function | Can Res, 59,2297,99 |
| Hs.173664 | HER2/Neu | v-erb-b2 avian erythroblastic leukemia viral oncogene homolog 2 | Modifying AR function | PNAS, 9,5458,99 |
| Hs.77271 | PKA | protein kinase, cAMP-dependent, catalytic, alpha | Modifying AR function | JBC 274,7777,99 |
| Hs.85112 | IGF1 | insulin-like growth factor 1 (somatomedin C) | Modifying AR function | Can Res, 54,5474,94 |
| Hs.2230 | EGF | | Modifying AR function | Can Res, 54,5474,94 |
| Hs.129841 | MEKK1 | MAPKKK1 | Modifying AR function | Mol Cell Biol, 19,5143,99 |
| Hs.83173 | Cyclin D3 | | Modifying AR function | Can Res, 59,2297,99 |
| Hs.75963 | IGF2 | | Modifying AR function | |
| Hs.89832 | Insulin | | Modifying AR function | |
| Hs.115352 | GH | | Modifying AR function | |
| Hs.1989 | 5 alpha reductase type2 | | Involved in Androgen metabolism | |
| Hs.76205 | Cytochrome P450, subfamily XIA | | Involved in Androgen metabolism | |
| Hs.1363 | Cytochrome P450, subfamily XVII, (steroid 17-alpha-hydroxylase), | | Involved in Androgen metabolism | |
| Hs.477 | Hydroxysteroid (17-beta) dehydrogenase 3 | | Involved in Androgen metabolism | |
| Hs.75441 | Hydroxysteroid (17-beta) dehydrogenase 4 | | Involved in Androgen metabolism | |
| Hs.38586 | Hydroxy-delta-5-steroid dehydrogenase, 3 beta- and steroid delta-isomerase 1 | | Involved in Androgen metabolism | |
| Hs.46319 | Sex hormone-binding globulin | | Involved in Androgen metabolism | |
| Hs.552 | SRD5A1 | | Involved in Androgen metabolism | |
| Hs.50964 | C-CAM | epithelial cell adhesion molecule | Down-regulated by Androgen | Oncogene, 18,3252,99 |
| Hs.7833 | hSP56 | selenium binding protein | Down-regulated by Androgen | Can Res, 58,3150,98 |
| Hs.77432 | EGFR | epidermal growth factor receptor | Down-regulated by Androgen | Endocrinology, 139,1369,98 |
| Hs.1174 | p16 | | Down-regulated by Androgen | Can Res, 57,4511,97 |
| Hs.55279 | maspin | | Down-regulated by Androgen | PNAS, 94,5673,97 |
| Hs.75789 | TDD5 (mouse) | Human mRNA for RTP, complete cds | Down-regulated by Androgen | PNAS, 94,4988,97 |
| Hs.75106 | TRPM-2 | clusterin (testosterone-repressed prostate message 2, apolipoprotein J) | Down-regulated by Androgen | |
| Hs.25640 | rat ventral prostate gene1 | claudin3 | Down-regulated by Androgen | PNAS, 94,12999,97 |
| ND | glutathione S-transferase | | Down-regulated by Androgen | PNAS, 94,12999,97 |
| Hs.25647 | c-fos | v-fos FBJ murine osteosarcoma viral oncogene homolog | Down-regulated by Androgen | PNAS, 94,12999,97 |
| N.D. | matrix carboxyglutamic acid protein (RAT) | | Down-regulated by Androgen | PNAS, 94,12999,97 |
| Hs.2962 | S100P | calcium binding prottein | Down-regulated by Androgen | Prostate 29,350,96 |
| Hs.75212 | omithine decarboxilase | omithine decarboxylase 1 | Down-regulated by Androgen | J Androl, 19,127,98 |
| Hs.84359 | Androge withdrawal apoptosis RVP1 | | Down-regulated by Androgen | |
| Hs.79070 | c-myc | v-myc avian myelocysomastosis viral oncogene homolog | Down-regulated by Androgen | |

TABLE 5-continued

Genes/ESTs as Defined by Publications:
Including Androgen Signaling, Prostate Specificity, Prostate Cancer Association, and
Nuclear Receptors/Regulators with Potential Interaction with Androgen Receptor

| Cluster ID | Gene Name | Description | | References |
|---|---|---|---|---|
| Hs.139033 | partially expressed gene 3 | | Down-regulated by Androgen | Mol Cell Endocrinol 155,69,(99) |
| Hs.20318 | PLU-1 | | Associated with Prostate Cancer | JBC, 274,15633,99 |
| Hs.18910 | POV1(PB39) | unique | Associated with Prostate Cancer | Genomics, 51,282,98 |
| Hs.119333 | caveolin | | Associated with Prostate Cancer | Clin Can Res, 4,1873,98 |
| ND, but 1 IMAGE CLONE | EST | R00540(2.6 kbp) = IMAGE: 123822 | Associated with Prostate Cancer | Urology, 50,302,97 |
| Hs.184906 | PTI-1 | prostate tumor inducing gene, trancated and mutated human elongation factor 1 alpha | Associated with Prostate Cancer | Can Res, 57,18,97, PNAS, 92,6778,95 |
| Hs.74649 | cytochrome c oxidase subunit VI c | | Associated with Prostate Cancer | Can Res, 56,3634,96 |
| Hs.4082 | PCTA-1 | prostate carcinoma tumor antigen, galectin family | Associated with Prostate Cancer | PNAS, 92,7252,96 |
| ND | pp32r1 | | Associated with Prostate Cancer | Nature Medicine, |
| ND | pp32r2 | | Associated with Prostate Cancer | Nature Medicine, 5,275,99 |
| Hs.184945 | GBX2 | | Associated with Prostate Cancer | The prostate journal, 1,61,99 |
| Hs.8867 | Cyr61 | inmmediate early protein | Associated with Prostate Cancer | Prostate, 36,85,98 |
| Hs.77899 | epithelial tropomyosin | actin binding protein | Associated with Prostate Cancer | Can Res, 56,3634,96 |
| Hs.76689 | pp32 | | Associated with Prostate Cancer | Nature Medicine, 5,275,99 |
| Hs.10712 | PTEN | | Associated with Prostate Cancer | |
| Hs.194110 | KAI1 | | Associated with Prostate Cancer | |
| Hs.37003 | H-ras | | Associated with Prostate Cancer | |
| Hs.184050 | K-ras | | Associated with Prostate Cancer | |
| Hs.69855 | N-ras | neuroblastoma RAS viral (v-ras) oncogene homolog | Associated with Prostate Cancer | |
| Hs.220 | TGFbeta receptor1 | | Associated with Prostate Cancer | |
| Hs.77326 | IGFBP3 | insulin-like growth factor binding protein 3 | Associated with Prostate Cancer | |
| Hs.79241 | bcl-2 | | Associated with Prostate Cancer | |
| Hs.159428 | Bax | | Associated with Prostate Cancer | |
| Hs.206511 | bcl-x | | Associated with Prostate Cancer | |
| Hs.86386 | mcl-1 | myeloid cell leukemia sequence 1 (BCL2-related) | Associated with Prostate Cancer | |
| Hs.1846 | p53 | tumor protein p53 (Li-Fraumeni syndrome) | Associated with Prostate Cancer | |
| Hs.38481 | CDK6 | cyclin-dependent kinase 6 | Associated with Prostate Cancer | |
| Hs.118630 | Mxi.1 | | Associated with Prostate Cancer | |
| Hs.184794 | GAGE7 | | Associated with Prostate Cancer | |
| Hs.118162 | fibronectin | | Associated with Prostate Cancer | Am J Pathol 154,1335,99 |
| Hs.128231 | PAGE-1 | | Associated with Prostate Cancer | JBC, 237,17618,98 |
| Hs.75875 | UEV1 | ubiquitin-conjugating enzyme E2 variant 1 | Associated with Prostate Cancer | Am J Pathol 154,1335,99 |
| Hs.75663 | PM5 | Human mRNA for pM5 protein | Associated with Prostate Cancer | Am J Pathol 154,1335,99 |
| Hs.180842 | BBC1 | breast basic conserved gene | Associated with Prostate Cancer | Am J Pathol 154,1335,99 |
| Hs.198024 | JC19 | | Associated with Prostate Cancer | Can Res 57,4075,97 |
| N.D. | GC79 | novel gene | Associated with Prostate Cancer | Can Res 57,4075,97 |
| Hs.77054 | B cell translocation gene 1 | | Associated with Prostate Cancer | Can Res 57,4075,97 |
| Hs.78122 | Regulatory factor X-associated ankyrin-containing protein | | Associated with Prostate Cancer | |
| Hs.3337 | transmembrane 4 superfamily member1 | | Associated with Prostate Cancer | |
| Hs.76698 | TL5 | | Associated with Prostate Cancer | Genebank |
| Hs.3776 | TL7 | | Associated with Prostate Cancer | Genebank |
| Hs.170311 | TL35 | | Associated with Prostate Cancer | Genebank |
| Hs.184914 | Human mRNA for TI-227H | | Associated with Prostate Cancer | |

TABLE 5-continued

Genes/ESTs as Defined by Publications:
Including Androgen Signaling, Prostate Specificity, Prostate Cancer Association, and
Nuclear Receptors/Regulators with Potential Interaction with Androgen Receptor

| Cluster ID | Gene Name | Description | References |
|---|---|---|---|
| Hs.62954 | ferritin, heavy polypeptide | Associated with Prostate Cancer | |
| Hs.71119 | N33 | Associated with Prostate Cancer | Genomics, 35,45(96) |

TABLE 6

Genes/ESTs as defined by publications:
Differentially expresed genes in prostate cancer from CGAP database (NIH)

| Cluster.ID | Gene name |
|---|---|
| Hs.179809 | EST |
| Hs.193841 | EST |
| Hs.99949 | prolactin-induced protein |
| Hs.101307 | EST |
| Hs.111256 | arachidonate 15-lipoxygenase |
| Hs.185831 | EST |
| Hs.115173 | EST |
| Hs.193988 | EST |
| Hs.159335 | EST |
| Hs.191495 | EST |
| Hs.187694 | EST |
| Hs.191848 | EST |
| Hs.193835 | EST |
| Hs.191851 | EST |
| Hs.178512 | EST |
| Hs.222886 | EST |
| Hs.210752 | EST |
| Hs.222737 | EST |
| Hs.105775 | EST |
| Hs.115129 | EST |
| Hs.115671 | EST |
| Hs.116506 | EST |
| Hs.178507 | EST |
| Hs.187619 | EST |
| Hs.200527 | EST |
| Hs.179736 | EST |
| Hs.140362 | EST |
| Hs.209643 | EST |
| Hs.695559 | EST |
| Hs.92323 | MAT8 |
| Hs.178391 | BTK |
| Hs.55999 | EST |
| Hs.171185 | Desmin |
| Hs.54431 | SGP28 |
| Hs.182624 | EST |
| Hs.112259 | T cell receptor gammma |
| Hs.76437 | EST |
| Hs.104215 | EST |
| Hs.75950 | MLCK |
| Hs.154103 | LIM |
| Hs.9542 | JM27 |
| Hs.153179 | FABP5 |
| Hs.195850 | EST |
| Hs.105807 | EST |
| Hs.115089 | EST |
| Hs.116467 | EST |
| Hs.222883 | EST |

TABLE 7

Androgen regulated Genes Defined by CPDR
Genes/ESTs Derived from CPDR-Genome Systems ARG Database

| Cluster | Gene Name | Description |
|---|---|---|
| Hs.152204 | TMPRSS2 | Up-regulated by Androgen |
| Hs.123107 | KLK1 | Up-regulated by Androgen |
| Hs.173334 | elongation factor ell2 | Up-regulated by Androgen |
| Hs.151602 | epithelial V-like antigen | Up-regulated by Androgen |
| Hs.173231 | IGFR1 | Up-regulated by Androgen |
| Hs.75746 | aldehyde dehydrogenase 6 | Up-regulated by Androgen |
| Hs.97708 | EST prostate and testis | Up-regulated by Androgen |
| Hs.94376 | proprotein convertase subtilisin/kexin type 5 | Up-regulated by Androgen |
| AF017635 | Homo sapiens Ste-20 related kinase SPAK mRNA, complete cds 4 {Incyte PD: 60737} | Up-regulated by Androgen |
| Hs.2798 | leukemia inhibitory factor receptor | Up-regulated by Androgen |
| Hs.572 | orosomucoid 1 | Up-regulated by Androgen |
| Hs.35804 | KIAA0032 gene product | Up-regulated by Androgen |
| Hs.114924 | solute carrier family 16 (monocarboxylic acid transporters), member 6 | Up-regulated by Androgen |
| Hs.37096 | zinc finger protein 145 (Kruppel-like, expressed in promyelocytic leukemia) | Up-regulated by Androgen |
| R07295 | sterol O-acyltransferase (acyl-Coenzyme A: cholesterol acyltransferase) 1 {Incyte PD: 2961248} | Up-regulated by Androgen |
| Hs.11899 | 3-hydroxy-3-methylglutaryl-Coenzyme A reductase | Up-regulated by Androgen |
| Hs.216958 | Human mRNA for KIAA0194 gene, partial cds | Up-regulated by Androgen |
| Hs.76901 | for protein disulfide isomerase-related | Up-regulated by Androgen |
| Hs.180628 | dynamin-like protein | Up-regulated by Androgen |
| Hs.81328 | nuclear factor of kappa light polypeptide gene enhancer in B-cells inhibitor, alpha | Up-regulated by Androgen |

TABLE 7-continued

Androgen regulated Genes Defined by CPDR
Genes/ESTs Derived from CPDR-Genome Systems ARG Database

| Cluster | Gene Name | Description |
| --- | --- | --- |
| Hs.159358 | acetyl-Coenzyme A carboxylase alpha | Up-regulated by Androgen |
| N24233 | IMAGE: 262457 | Up-regulated by Androgen |
| Hs.188429 | EST | Up-regulated by Androgen |
| Hs.77508 | glutamate dehydrogenase 1 | Up-regulated by Androgen |
| Hs.12017 | *Homo sapiens* KIAA0439 mRNA | Up-regulated by Androgen |
| Hs.10494 | EST | Up-regulated by Androgen |
| Hs.20843 | EST | Up-regulated by Androgen |
| Hs.153138 | origin recognition complex, subunit 5 (yeast homolog)-like | Up-regulated by Androgen |
| Hs.79136 | Human breast cancer, estrogen regulated LIV-1 protein (LIV-1) mRNA, partial cds | Up-regulated by Androgen |
| Hs.35750 | anthracycline resistance-associated | Up-regulated by Androgen |
| Hs.56729 | lymphocyte-specific protein 1 | Up-regulated by Androgen |
| Hs.17631 | EST | Up-regulated by Androgen |
| Hs.46348 | bradykinin receptor B1 | Up-regulated by Androgen |
| Hs.172851 | arginase, type II | Up-regulated by Androgen |
| Hs.66744 | twist (*Drosophila*) homolog | Up-regulated by Androgen |
| Hs.185973 | membrane fatty acid (lipid) desaturase | Up-regulated by Androgen |
| Hs.26 | ferrochelatase (protoporphyria) | Up-regulated by Androgen |
| Hs.169341 | ESTs, Weakly similar to phosphatidic acid phosphohydrolase type-2c [*H. sapiens*] | Up-regulated by Androgen |
| Hs.119007 | S-phase response (cyclin-related) | Up-regulated by Androgen |
| Hs.76285 | *H. sapiens* gene from PAC 295C6, similar to rat PO44 | Up-regulated by Androgen |
| Hs.167531 | *Homo sapiens* mRNA full length insert cDNA clone EUROIMAGE 195423 | Up-regulated by Androgen |
| Hs.9817 | arg/Abl-interacting protein ArgBP2 | Up-regulated by Androgen |
| Hs.28241 | EST | Down-regulated by Androgen |
| Hs.25925 | *Homo sapiens* clone 23860 mRNA | Down-regulated by Androgen |
| Hs.10319 | UDP glycosyltransferase 2 family, polypeptide B7 | Down-regulated by Androgen |
| Hs.155995 | *Homo sapiens* mRNA for KIAA0643 protein, partial cds | Down-regulated by Androgen |
| Hs.23552 | EST | Down-regulated by Androgen |
| Hs.41693 | DnaJ-like heat shock protein 40 | Down-regulated by Androgen |
| Hs.90800 | matrix metalloproteinase 16 (membrane-inserted) | Down-regulated by Androgen |
| Hs.2996 | sucrase-isomaltase | Down-regulated by Androgen |
| Hs.166019 | regulatory factor X, 3 (influences HLA class II expression) | Down-regulated by Androgen |
| Hs.27695 | midline 1 (Opitz/BBB syndrome) | Down-regulated by Androgen |
| Hs.183738 | chondrocyte-derived ezrin-like protein | Down-regulated by Androgen |
| Hs.75761 | SFRS protein kinase 1 | Down-regulated by Androgen |
| Hs.197298 | NS1-binding protein | Down-regulated by Androgen |
| Hs.149436 | kinesin family member 5B | Down-regulated by Androgen |
| Hs.81875 | growth factor receptor-bound protein 10 | Down-regulated by Androgen |
| Hs.75844 | ESTs, Weakly similar to (defline not available 5257244) [*H. sapiens*] | Down-regulated by Androgen |
| Hs.30464 | cyclin E2 | Down-regulated by Androgen |
| Hs.198443 | inositol 1,4,5-triphosphate receptor, type 1 | Down-regulated by Androgen |
| Hs.177959 | a disintegrin and metalloproteinase domain 2 (fertilin beta) | Down-regulated by Androgen |
| Hs.44197 | *Homo sapiens* mRNA; cDNA DKFZp564D0462 (from clone DKFZp564D0462) | Down-regulated by Androgen |
| Hs.150423 | cyclin-dependent kinase 9 (CDC2-related kinase) | Down-regulated by Androgen |
| Hs.78776 | Human putative transmembrane protein (nma) mRNA, complete cds | Down-regulated by Androgen |
| Hs.25740 | ESTs, Weakly similar to !!!! ALU SUBFAMILY SQ WARNING ENTRY !!!! [*H. sapiens*] | Down-regulated by Androgen |
| Hs.131041 | EST | Down-regulated by Androgen |
| Hs.19222 | ecotropic viral integration site 1 | Down-regulated by Androgen |
| Hs.9879 | EST | Down-regulated by Androgen |
| Hs.118722 | fucosyltransferase 8 (alpha (1,6) fucosyltransferase) | Down-regulated by Androgen |
| Hs.47584 | potassium voltage-gated channel, delayed-rectifier, subfamily S, member 3 | Down-regulated by Androgen |
| Hs.115945 | mannosidase, beta A, lysosomal | Down-regulated by Androgen |
| Hs.171740 | ESTs, Weakly similar to Zic2 protein [M. musculus] | Down-regulated by Androgen |
| Hs.32970 | signaling lymphocytic activation molecule | Down-regulated by Androgen |
| Hs.196349 | EST | Down-regulated by Androgen |
| Hs.182982 | *Homo sapiens* mRNA for KIAA0855 protein, partial cds | Down-regulated by Androgen |
| Hs.72918 | small inducible cytokine A1 (I-309, homologous to mouse Tca-3) | Down-regulated by Androgen |
| Hs.84232 | transcobalamin II; macrocytic anemia | Down-regulated by Androgen |
| Hs.10086 | EST | Down-regulated by Androgen |
| Hs.1327 | Butyrylcholinesterase | Down-regulated by Androgen |
| Hs.166684 | serine/threonine kinase 3 (Ste20, yeast homolog) | Down-regulated by Androgen |
| AA558631 | EST | Down-regulated by Androgen |
| Hs.150403 | dopa decarboxylase (aromatic L-amino acid decarboxylase) | Down-regulated by Androgen |
| Hs.177548 | postmeiotic segregation increased (*S. cerevisiae*) 2 | Down-regulated by Androgen |

TABLE 8

Other Genes Associated with Cancers

| Cluster | Gene name | Description |
|---|---|---|
| Hs.146355 | c-Abl | v-abl Abelson murine leukemia viral oncogene homolog 1 |
| Hs.96055 | E2F1 | |
| Hs.170027 | MDM2 | |
| Hs.1608 | RPA | replication protein A3 (14 kD) |
| Hs.99987 | XPD | ERCC2 |
| Hs.77929 | XPB | ERCC3 |
| Hs.1100 | TBP | TATA box binding protein |
| Hs.60679 | TAFII31 | TATA box binding protein (TBP)-associated factor, RNA polymerase II, G, 32 kD |
| Hs.78865 | TAFII70 | Human TBP-associated factor TAFII80 mRNA, complete cds |
| Hs.178112 | DP1 | deleted in poliposis |
| Hs.119537 | p62 | |
| Hs.48576 | CSB | excision repair cross-complementing rodent repair deficiency, complementation group 5 |
| Hs.73722 | Ref-1 | |
| Hs.194143 | BRCA1 | breast cancer 1, early onset |
| Hs.184760 | CBF | |
| Hs.1145 | WT-1 | Wilms tumor 1 |
| Hs.2021 | Sp1 | |
| Hs.144477 | CK I | |
| Hs.155627 | DNA-PK | |
| Hs.170263 | p53BP1 | Human clone 53BP1 p53-binding protein mRNA, partial cds |
| Hs.44585 | p53BP2 | tumor protein p53-binding protein, 2 |
| Hs.6241 | p85 alpha | PI3 kinase |
| Hs.23707 | p85 beta | PI3 kinase |
| Hs.194382 | ATM | |
| Hs.184948 | BIN1 | |
| Hs.137569 | p51B | p63 |
| Hs.1334 | bmyb | v-myb avian myeloblastosis viral oncogene homolog |
| Hs.81942 | DNA polymerase alpha | polymerase (DNA directed), alpha |
| Hs.180952 | Beta actin | |
| Hs.93913 | IL-6 | interleukin 6 (interferon, beta 2) |
| Hs.190724 | MAP4 | microtubule-associated protein 4 |
| Hs.1384 | MGMT | o-6-methylguanine-DNA methyltransferase |
| Hs.79572 | Cathepsin D | cathepsin D (lysosomal aspartyl protease) |
| Hs.111301 | Collagenase IV | |
| Hs.151738 | Collagenase IV | |
| Hs.51233 | DR5 | |
| Hs.82359 | FAS | |
| Hs.80409 | GADD45 | DNA-damage-inducible transcript 1 |
| Hs.86161 | GML | GPI-anchored molecule like protein |
| Hs.50649 | PIG3 | quinone oxidoreductase homolog |
| Hs.184081 | Siah | seven in absentia (*Drosophila*) homolog 1 |
| Hs.56066 | bFGF | fibroblast growth factor 2 (basic) |
| Hs.205902 | IGF1-R | |
| Hs.21330 | MDR1 | P glycoprotein 1/multiple drug resistance 1 |
| Hs.74427 | PIG11 | *Homo sapiens* Pig11 (PIG11) mRNA, complete cds |
| Hs.76507 | PIG7 | LPS-induced TNF-alpha factor |
| Hs.8141 | PIG8 | |
| Hs.146688 | PIG12 | |
| Hs.104925 | PIG10 | |
| Hs.202673 | PIG6 | |
| Hs.80642 | STAT4 | |
| Hs.72988 | STAT2 | |
| Hs.167503 | STAT5A | |
| Hs.738 | early growth response 1 | |
| Hs.85148 | villin2 | |
| Hs.109012 | MAD | |
| Hs.75251 | DEAD/H box binding protein 1 | |
| Hs.181015 | STAT6 | |
| Hs.199791 | SSI-3 | STAT induced STAT inhibitor 3 |
| Hs.21486 | STAT1 | |
| Hs.142258 | STAT3 | |
| Hs.76578 | PIAS3 | Protein inhibitor of activated STAT3 |
| Hs.44439 | CIS4 | STAT induced STAT inhibitor 4 |
| Hs.50640 | SSI-1 | JAK binding protein |
| Hs.54483 | NMI | N-Myc and STAT interactor |
| Hs.105779 | PIASy | Protein inhibitor of activated STAT |
| Hs.110776 | STATI2 | STAT induced STAT inhibitor 2 |
| Hs.181112 | EST similar to STAT5A | |

TABLE 9

Functional Categories of ARGs

| Tag | T/C | Access # | Name, Description |
|---|---|---|---|
| Transcription Regulators | | | |
| GCCAGCCCAG (SEQ ID NO:13) | 11/1 | H41030 | KAP1/TIF1beta, KRAB-associated protein 1 |
| GTGCAGGGAG (SEQ ID NO:14) | 18/2 | AF071538 | PDEF, eta transcription factor |
| GACAAACATT (SEQ ID NO:15) | 8/1 | NM_003201 | mtTF1, mitochondrial transcription factor 1 |
| ATGACTCAAG (SEQ ID NO:16) | 8/1 | X12794 | ear-2, v-erbA related |
| GAAAAGAAGG (SEQ ID NO:17) | 8/1 | U80669 | Nkx3.1, homeobox |
| CCTGTACCCC (SEQ ID NO:18) | 5/1 | AF072836 | Sox-like transcriptional factor |
| CCTGAACTGG (SEQ ID NO:19) | 1/8 | NM_001273 | CHD4/Mi2-beta, histone acetylase/ deacetylase, chromodomain helicase |
| TGACAGCCCA (SEQ ID NO:20) | 1/7 | U81599 | Hox B13, homeobox |
| RNA Processing and Translational Regulators | | | |
| TACAAAACCA (SEQ ID NO:21) | 12/1 | NM_005381 | NCL, Nucleolin |
| AATTCTCCTA (SEQ ID NO:22) | 8/1 | U41387 | GURDB, nucleolar RNA helicase |
| TGCATATCAT (SEQ ID NO:23) | 8/1 | D89729 | XPO1, exportin 1 |
| CTTGACACAC (SEQ ID NO:24) | 14/2 | AL080102 | EIF5, translation initiation factor 5 |
| TGTCTAACTA (SEQ ID NO:25) | 5/1 | AF078865 | CGI-79, RNA-binding protein |
| GTGGACCCCA (SEQ ID NO:26) | 10/2 | AF190744 | SiahBP1/PUF60, poly-U binding splicing factor |
| ATAAAGTAAC (SEQ ID NO:27) | 1/11 | NM_007178 | UNRIP, unr-interacting protein. |
| TACATTTTCA (SEQ ID NO:28) | 1/7 | X85373 | SNRPG, small nuclear RNP polypeptide G |
| TCAGAACAGT (SEQ ID NO:29) | 1/7 | NM_002092 | GRSF-1, G-rich RNA binding factor 1 |
| CAACTTCAAC (SEQ ID NO:30) | 0/5 | NM_006451 | PAIP1, poly A BP-interacting protein 1 |
| GATAGGTCGG (SEQ ID NO:31) | 0/5 | Z11559 | IREBP1, Iron-responsive element BP 1 |
| CTAAAAGGAG (SEQ ID NO:32) | 2/10 | M15919 | SNRPE, small nuclear RNP polypeptide E |
| Genomic Maintenance and Cell Cycle Regulation | | | |
| GTGGTGCGTG (SEQ ID NO:33) | 10/1 | AF035587 | XRCC2, X-ray repair protein 2 |
| TCCCCGTGGC (SEQ ID NO:34) | 7/1 | D13643 | KIAA0018, Dimunuto-like |
| ATTGATCTTG (SEQ ID NO:35) | 6/1 | NM_002947 | RPA3, Replication protein A 14 kDa subunit |
| AGCTGGTTTC (SEQ ID NO:36) | 16/3 | NM_004879 | PIG8, p53 induced protein |
| CCTCCCCCGT (SEQ ID NO:37) | 10/2 | AF044773 | BAF, barrier-to-autointegration factor |
| ATGTACTCTG (SEQ ID NO:38) | 1/7 | NM_000884 | IMPDH2, IMP dehydrogenase 2 |
| GATGAAATAC (SEQ ID NO:39) | 0/5 | NM_006325 | ARA24, androgen receptor assoc protein 24 |
| GTGCATCCCG (SEQ ID NO:40) | 0/5 | X16312 | Phosvitin/casein kinase II beta subunit |
| Protein Trafficking and Chaperoning | | | |
| GAAATTAGGG (SEQ ID NO:41) | 12/1 | AB020637 | KIAA0830, similar to golgi antigen |
| TTTCTAGGGG (SEQ ID NO:42) | 10/1 | AF15189 | CGI-140, lysosomal alpha B mannosidase |
| CCCAGGGAGA (SEQ ID NO:43) | 7/1 | AF026291 | CCT, chaperonin t-complex polypeptide 1 |
| GTGGCGCACA (SEQ ID NO:44) | 13/2 | S79862 | 26 S protease subunit 5b |

TABLE 9-continued

Functional Categories of ARGs

| Tag | T/C | Access # | Name, Description |
|---|---|---|---|
| TTGCTTTTGT (SEQ ID NO:45) | 15/3 | NM_001660 | ARF4, ADP-ribosylation factor 4 |
| ATGTCCTTTC (SEQ ID NO:46) | 10/2 | NM_005570 | LMAN1, mannose BP involved in EPR/Golgi traffic |
| Energy Metabolism, Apoptosis and Redox Regulators | | | |
| TGTTTATCCT (SEQ ID NO:47) | 13/2 | M14200 | DBI, diazepam binding inhibitor |
| GCTTTGTATC (SEQ ID NO:48) | 6/1 | D16373 | dihydrolipoamide succinyltransferase |
| GTTCCAGTGA (SEQ ID NO:49) | 6/1 | AA653318 | FKBP5, FK506-binding protein 5 |
| TAGCAGAGGC (SEQ ID NO:50) | 6/1 | AA425929 | NDUFB10, NADE dehydrogenase 1 beta subcomplex 10 |
| ACAAATTATG (SEQ ID NO:51) | 5/1 | NM_003375 | VDAC, voltage-dependent anion channel |
| CAGTTTGTAC (SEQ ID NO:52) | 5/1 | NM_000284 | PDHA1, Pyruvate dehydrogenase E1-alpha subunit |
| GATTACTTGC (SEQ ID NO:53) | 5/1 | NM_004813 | PEX16, peroxisomal membrane biogenesis factor |
| GGCCAGCCCT (SEQ ID NO:54) | 5/1 | X15573 | PFKL, 1-phosphofructokinase |
| CAATTGTAAA (SEQ ID NO:55) | 1/10 | NM_004786 | TXNL, thioredoxin-like protein |
| AAAGCCAAGA (SEQ ID NO:56) | 2/15 | NM_001985 | ETFB, electron transfer flavoprotein beta subunit |
| CAACTAATTC (SEQ ID NO:57) | 1/7 | NM_001831 | CLU, Clustrin |
| AAGAGCTAAT (SEQ ID NO:58) | 0/5 | NM_004446 | EPRS, glutamyl-prolyl-tRNA synthetase |
| Signal Transduction | | | |
| CTTTTCAAGA (SEQ ID NO:59) | 9/1 | X59408 | CD46, complement system membrane cofactor |
| GTGTGTAAAA (SEQ ID NO:60) | 9/1 | NM_005745 | BAP31/BAP29 IgD accessory proteins |
| ACAAAATGTA (SEQ ID NO:61) | 8/1 | NM_000856 | GUCY1A3, Guanylate cyclase 1, alpha 3 |
| AAGGTAGCAG (SEQ ID NO:62) | 7/1 | NM_006367 | CAP, Adenylyl cyclase-associated protein |
| GGCGGGGCCA (SEQ ID NO:63) | 7/1 | AB002301 | microtubule assoc. serine/threonine kinase |
| GGCCAGTAAC (SEQ ID NO:64) | 6/1 | AL096857 | similar to BAT2, integrin receptor |
| AACTTAAGAG (SEQ ID NO:65) | 12/2 | AB018330 | calmodulin-dependent protein kinase kinase β |
| AGGGATGGCC (SEQ ID NO:66) | 5/1 | NM_006858 | IL1RL1LG, Putative T1/ST2 receptor |
| CTTAAGGATT (SEQ ID NO:67) | 2/10 | AF151813 | CGI-55 protein |

The "tag to gene" identification is based on the analysis performed by SAGE software and/or "tag to gene" application of the NIH SAGE Website. T/C represent the number of tags for each transcript in androgen treated (T) and control (C) LNCaP libraries. The differences in expression levels of genes identified by tags shown here were statistically significant (p<0.05) as determined by the SAGE software.

REFERENCES

1. Landis S H, Murray T, Bolden S, and Wingo P A: Cancer statistics. CA Cancer J. Clin., 49:8-31, 1999.
2. Pannek J and Partin A W: Prostate-specific Antigen: What is new in 1977. Oncology 11, 1273-1282, 1997.
3. Small E J: Update on the diagnosis and treatment of prostate cancer: Curr. Opin. Oncol., 10:244-252, 1998.
4. Krongrad A, Lai H, and Lai S: Survival after radical prostatectomy. JAMA, 278:44-46, 1997.
5. Garwick, M B and Fair W R: Prostate Cancer, Scientific American, 75-83, 1998.
6. Augustus M, Moul J W, and Srivastava S: The molecular phenotype of the malignant prostate. Molecular pathology of early cancer (in press), 1999.
7. Sakr W A, Macoska J A, Benson P, Benson D J, Wolman S R, Pontes J E, and Crissman: Allelic loss in locally metastatic, multi-sampled prostate cancer. Cancer Res., 54:3273-3277, 1994.
8. Mirchandani D, Zheng J, Miller G L, Ghosh A K, Shibata D K, Cote R J and Roy-Burman P: Heterogeneity in intratumor distribution of p53 mutations in human prostate cancer. Am. J. Path. 147:92-101, 1995.
9. Bauer J J, Moul J W, and McLeod D G: CaP: Diagnosis, treatment, and experience at one tertiary medical center, 1989-1994. Military Medicine, 161:646-653,1996.
10. Moul J W, Gaddipati J, and Srivastava S: 1994. Molecular biology of CaP. Oncogenes and tumor suppressor genes. Current Clinical Oncology: CaP. (Eds. Dawson, N.A. and Vogelzang, N.J.), Wiley-Liss Publications, 19-46.
11. Lalani E-N, Laniado M E and Abel P D: Molecular and cellular biology of prostate cancer. Cancer and Mets. Rev., 16:29-66, 1997.
12. Shi X B, Gumerlock P H, deVere White R W: Molecular Biology of CaP. World J. Urol; 14, 318-328, 1996.
13. Heidenberg H B, Bauer J J, McLeod D G, Moul J W and Srivastava S: The role of p53 tumor suppressor gene in CaP: a possible biomarker? Urology, 48:971-979, 1996.
14. Bova G S and Issacs W B: Review of allelic loss and gain in prostate cancer. World J Urol., 14:338-346, 1996.
15. Issacs W B and Bova G S: Prostate Cancer: The Genetic Basis of Human Cancer. Eds. Vogelstein B, and Kinzler K W, McGraw-Hill Companies, Inc., pp. 653-660, 1998.
16. Heidenberg H B, Sesterhenn I A, Gaddipati J, Weghorst C M, Buzard G S, Moul J W, and Srivastava S: Alterations of the tumor suppressor gene p53 in a high fraction of treatment resistant prostate cancer. J. Urol., 154:414421, 1995.
17. Bauer J J, Sesterhenn I A, Mostofi F K, McLeod D G, Srivastava S, Moul J W: p53 protein expression is an independent prognostic marker in clinically localized prostate cancer patients. Clin. Cancer Res., 1: 1295-1300, 1995.
18. Bauer J J, Sesterhenn I A, Mostofi F K, McLeod D G, Srivastava S, Moul, J W: Elevated levels of apoptosis regulator proteins p53 and bcl-2 are independent prognostic biomarkers in surgically treated clinically localized prostate cancer patients. J. Urol., 1511-1516,1996.
19. Yang G, Stapleton A M, Wheeler T M, Truong L D, Timme T O, Scardino T P, and Thompson T O: Clustered p53 immunostaining. A novel pattern associated with prostate cancer progression. Clin. Cancer Res., 2:399-401, 1996.
20. Cairns P, Okami K, Halachmi S, Halachmi N, Esteller M, Herman J G, Jen J, Isaacs W B, Bova G S, and Sidransky D: Frequent inactivation of PTEN/MMAC1 in primary prostate cancer. Cancer Res, 57:4997-5000, 1997.
21. Suzuki H, Freije D, Nusskern D R, Okami K, Cairns P, Sidransky D, Isaacs W B, and Bova G S: Interfocal heterogeneity of PTEN/MMAC1 gene alterations in multiple metastatic prostate cancer tissues: Cancer Res, 58:204-209, 1998.
22. Jenkins R B, Qian J, Lieber M M and Bostwick D G: Detection of c-myc oncogene amplification and chromosomal abnormalities in metastatic prostatic carcinoma by fluorescence in situ hybridization. Cancer Res, 57:524-531, 1997.
23. Reiter R E, Gu Z, Watabe T., Thomas G, Szigeti K, Davis E, Wahl M, Nisitani S, Yamashiro I, LeBeau M M, Loda M and Witte O N: Prostate stem cell antigen: a cell surface marker overexpressed in prostate cancer. Proc Natl Acad Sci, 95:1735-40, 1998.
24. Visakorpi T, Kallioniemi A H, Syvanen A, Hyytinen E R, Karhu R, Tammela T, Isola J J and Kallioniemi O-P: Genetic changes in primary and recurrent prostate cancer. Cancer Res, 55:342-347, 1995.
25. Cher M L, Bova G S, Moore D H, Small E J, Carroll P A, Pinn S S, Epstein J L, Isaacs W B and Jensen R H: Genetic alterations in untreated metastases and androgen-independent prostate cancer detected by comparative genomic hybridization and allotyping. Cancer Res, 56:3091-3102, 1996.
26. Srikantan V, Sesterhenn I A, David L, Hankins G R, Avallone F A, Livezey J R, Connelly R, Mostofi F K, McLeod D G, Moul J W, Chandrasekharappa, S C, and Srivastava S: Chromosome 6q alterations in human prostate cancers. Int J Cancer (in press), 1999.
27. Smith J R, Freije D, Carpten J D, Gronberg H, et al: Major susceptibility locus for prostate cancer on chromosome 1 suggested by a genome-wide search. Science, 276:1371-1374, 1996.
28. Xu J, Meyers D, Freije D, Issacs S, et al: Evidence for a prostate cancer susceptibility locus on x chromosome. Nat. Genet, 20: 175-179, 1998.
29. Liang, Peng, and Pardee A B: Differential display of eukaryotic messenger RNA by means of the polymerase chain reaction. Science 257:967-971, 1992.
30. Velculescu V E, Zhang L, Vogelstein B, and Kinzler K W: Serial analysis of gene expression Science, 270:484487, 1995.
31. Chena M, Shalon D S, Davis R W, and Brown P O: Quantitative monitoring of gene expression patterns with a complementary DNA microarrays. Science, 270:467-470, 1995.
32. Srikantan V., Zou Z, Davis L D, Livezey J, Sesterhenn I A, Xu L, Mostofi F K, McLeod D G, Moul J W, and Srivastava S: Structure and expression of a novel prostate specific gene PCGEM1. American Assoc. Cancer Res. Meeting, Philadelphia, Pa., 1999.
33. Xu, L, Su Y, Labiche R, McLeod D G, Moul J W and Srivastava S: Probing the androgen regulated genes (ARGs) in prostate cancer cells by serial analysis of gene expression (SAGE). American Assoc. of Cancer Research Meeting, 1999.
34. Huggins, C., Hodges, C. V. Studies on prostate cancer, effects of castration, of estrogens and androgen injection on serum phosphatase in metastatic carcinoma of the prostate. Cancer Res, 1:293-297,1941.

35. Moul J W: Contemporary hormonal management of advanced prostate cancer. Oncology, 12: 499-505, 1998.
36. Veldscholte, J, Ris-Stalpers C, Kulper G G J M, Jenster G, Berre-voets C, Classen E, Van Roooj H C J, Trapman J, Brinkmann A O, Mulder E. A mutation in the ligand binding domain of the androgen receptor of human LNCaP cells affects steroid binding characteristics and response to anti-androgens. Biochem. Biophys. Res. Commun., 173: 534-540, 1990.
37. Newmark J R, Hardy O, Tonb D C, Carter B S, Epstein J I, Isaacs W B, Brown T R, Barrack E R. Androgen receptor gene mutations in human prostate cancer. Proc Natl Acad Sci USA, 89:6319-6323, 1992.
38. Culig Z, Hobisch A, Cronauer M V, Cato A C B, Hittmair A, Radmayr C, Eberie J, Bartsch G, Klocker H. Mutant androgen receptor detected in an advanced stage prostatic carcinoma is activated by adrenal androgens and progesterone. Mol. Endocrinol, 7:1541-1550, 1993.
39. Suzuki H, Sato N, Watabe Y, Masai M, Seino S, Shimazaki S. Androgen receptor gene mutations in human prostate cancer. J Steroid Biochem Mol Biol, 46:759-765, 1993.
40. Gaddipatti J P, McLeod D G, heidenberg H B, Sesterhann I A, Finger M J, Moul J W, Srivastava S. Frequent detection of codon 877 mutation in the androgen receptor gene in advanced prostate cancers. Cancer Res, 54:2861-2864.1994.
41. Peterziel H, Culig Z, Stober J, Hobisch A, Radmayr C, Bartsch G, Klocker, Cato ACB. Mutant androgen receptors in prostate cancer distinguish between amino acid sequence requirements for transactivation and ligand binding. Int J Cancer, 63:544-550, 1995.
42. Taplin M-E, Bubley G J, Shuster T D, Frantz M E, Spooner A E, Ogata G K, Keer H N, Balk S P. Mutation of the androgen receptor gene in metastatic androgen independent prostate cancer. N Engl J Med, 332:1393-1398.
43. Tilley W D, Buchanan G, Hickey T E, Bental J M. Mutation in the androgen receptor gene are associated with progression of human prostate cancer to androgen independence. Clin Cancer Res, 2: 277-285,1994.
44. Visakorpi T, Hyytinen E, Koivisto P, tanner M, Keinanen R, Palmberg C, Tammela T, Isola J, Kallioniemi OP. In vivo amplification of the androgen receptor gene and progression of human prostate cancer. Nature Genet, 9:401-406, 1995.
45. Koivisto P, Kononen J, Palmberg C, Tammela T, Hyytinen E, Isola J, Trapman J, Cleutjens K, Noordzij A, Visakorpi T, Kallioniemi O P. Androgen receptor gene amplification: a possible molecular mechanism for androgen deprivation therapy failure in prostate cancer. Cancer Res, 57:314-318, 1997.
46. Culig Z, Hobisch A, Cronauer M V, Radmayr C, Trapman J, Hittmair A, Bartsch G, Klocker H. Androgen receptor activation in prostate tumor cell lines by insulin-like growth factor-1, keratinocyte growth factor, and epidermal growth factor. Cancer Res, 54:5474-5478, 1994.
47. Yeh S, Chang C. Cloning and characterization of a specific coactivator, ARA70, for the androgen recptor in human prostate cells. Proc Natl Acad Sci USA, 93:5517-5521, 1996.
48. Nagabhushan M, Miller C M, Pretlow T P, Giaconia J M, Edgehouse N L, Schwartz S, Kung H-J, deVere White R W, Gumerlock P H, Resnick M I, Amini S B, Pretlow T G. CWR22: The first human prostate cancer Xenograft with strongly androgen-independent and relapsed strains both in vivo and in soft agar. Cancer Res, 56:3402-4306, 1996.
49. Gregory C W, Hamil K G, Kim D, Hatt S H, Pretlow T G, Mohler J L, French F S. Androgen receptor expression in androgen independent cancer is associated with increased expression of androgen regulated genes. Cancer Res, 58:5718-5724,1998.
50. Noble R L: The development of prostatic adenocarcinoma in Nb rats following prolonged sex hormone administration. Cancer Res, 37:1929-1933,1977.
51. Pollard M: Lobund-Wistar rat model of prostate cancer in man. Prostate, 37:1-4, 1998.
52. Pollard M, Luckert P H, and Snyder D L: The promotional effect of testosterone on induction of prostate cancer in MNU-sensitized L-W rats. Cancer Lett, 45:209-212, 1989.
53. Gann P H, Hennekens C H, Ma J, Longcope C, Stampfer M J: Prospective study of sex hormone levels and risk of prostate cancer J Natl Cancer Inst, 88:1118-1126,1996.
54. Hakimi J M, Schoenberg M P, Rondinelli R H, Piantadosi S, Barrack E R. Androgen receptor variants with short glutamine or glycine repeats may identify unique subpopulations of men with prostate cancer. Clin Cancer Res, 9:1599-1608, 1997.
55. Giovanucci E, Stampfer M J, Krithivas K, Brown M, Brafsky A, Talcott J, Hennekens CH, Kantoff PW. The CAG repeat within the androgen receptor gene and its relationship to prostate cancer. Proc Natl Acad Sci USA, 94:3420-3423,1997.
56. Coetzee G A, Ross R K. Prostate cancer and the androgen receptor. J. Natl Cancer Inst, 86:872-873, 1994.
57. Moul J W. Increased risk of prostate cancer in African men. Mol. Urol, 1:119-127,1997.
58. Chamberlain N L, Driver E D, Miesfeld R L. The length and location of CAG trinucleotide repeats in the androgen receptor N-terminal domain affect transactivation function. Nucleic Acids Res, 22:3181-3186, 1994.
59. Trapman J, Cleutzens K B J M. Androgen regulated gene expression in prostate cancer. Seminars in Canc Biol, 8:29-36,1997.
60. Yuan S, Trachtenberg J, Mills G B, Brown T J, and Keating A: Androgen-induced inhibition of cell proliferation in an androgen-insensitive prostate cancer cell line (PC3) transfected with human androgen receptor complementary DNA. Cancer Res,53: 1304-1311, 1993.
61. Velculescu V E, Zhang L, Vogelstein B, and Kinzler K W: Serial Analysis of Gene Expression. Science, 270, 484-487, 1995
62. Polyak K, Yong X, Zweier J L, Kinzler K W, and Vogelstein B: A model for p53 induced apoptosis. Nature, 389, 300-306, 1997.
63. Hermeking H, Lengauer C, Polyak C, He T-C, Zhang L, Thiagalingam S, Kinzler K W, and Vogelstein B: 14-3-3 is a p53-regulated inhibitor of G2/M progression. Molecular Cell, 1: 3-11, 1997.
64. He T-C, Sparks A B, Rago C, Hermeking H, Zawel L, da Costa L T, Morin P J, Vogelstein B, and Kinzler K W: Identification of c-myc as a target of the APC pathway. Science, 281;1438-1441, 1998.
65. Bieberich, C. J., Fujita, K., He, W. W., and Jay, G.: Prostate-specific and androgen-dependent expression of a novel homeobox gene. J Biol Chem, 271: 31779-31782, 1996.
66. Sciavolino, P. J., Abrams, E. W., Yang, L., Austenberg, L. P., Shen, M. M., and Abate-Shen, C.: Tissue-specific expression of murine Nkx3.1 in the male urogenital sinus. Dev Dyn, 209: 127-138, 1997.
67. He, W. W., Sciavolino, P. J., Wing, J., Augustus, M., Hudson, P., Meissner, S. P., Curtis, R. T., Shell, B. K., Bostwick, D. G., Tindall, D. J., Gelmann, E. P., Abate-Shen, C., and Carter, K. C.: A novel human prostate-specific androgen-regulated homeobox gene (NKX3.1) that maps to 8p21, a region frequently deleted in prostate cancer. Genomics, 43: 69-77, 1997.

68. Prescott J. L., Blok L., and Tindall D. J.: Isolation and androgen regulation of the human homeobox cDNA, NKX3.1. The Prostate, 35: 71-80, 1998.

69. Xu L, Srikantan V, Sesterhenn I A, Augustus M, Sui D, Moul J W, Carter K C and Srivastava S: Evaluation of expression of androgen regulated prostate specific homeobox gene, NKX3.1 in human prostate cancer. Int. Symp. on Biol. of Prostate Growth, Bethesda, 176, 1998; Manuscript submitted to J Urol, 1999.

70. Voeller, H. J, Augustus, M, Madike, V., Bova, G. S., Carter, K. C., and Gelmann, E. P.: Coding region of NKX3.1, a prostate-specific homeobox gene on 8p21, is not mutated in human prostate cancers. Cancer Res, 57: 4455-4459, 1997.

71. Song, K., Wang, Y., and Sassoon, D.: Expression of Hox-7.1 in myoblasts inhibits terminal differentiation and induces cell transformation. Nature, 360: 477-481, 1992.

72. Maulbecker, C. C., and Gruss, P.: The oncogenic potential of deregulated homeobox genes. Cell Growth Differ, 4: 431-441,1993.

73. Krosl, J., Baban, S., Krosl, G., Rozenfeld, S., Largman, C., and Sauvageau, G.: Cellular proliferation and transformation induced by HOXB4 and HOXB3 proteins involves cooperation with PBX1. Oncogene, 16: 3403-3412, 1998.

74. Kaighn M E, Reddel R R, Lechner J F, Peehl D M, Camalier R F, Brash D E, Saffioti U, and Harris C C: Transformation of human neonatal prostate epithelial cells strontium phosphate transfection with plasmid containing SV40 early region genes. Cancer Res, 49: 3050-3056, 1989.

75. Kuettel M R, Thraves P J, Jung M, Varghese S P, Prasad S C, Rhim J S, and Dritschilo A: Radiation-induced neoplastic transformation of human prostate epithelial cells. Cancer Res, 56:5-10,1996.

76. Srivastava S, Wheelock R H P, Eva A, and Aaronson S A: Identification of the protein encoded by novel human diffuse B cell lymphoma oncogene. Proc Natl Acad Sci, USA, 83:8868-8872, 1986.

77. Graziani G, Ron D, Eva A, and Srivastava: The human dbl proto-oncogene product is a cytoplasmic phosphoprotein which is associated with cytoskeletal matrix. Oncogene, 4:823-829, 1989.

78. Srivastava S, Zou Z, Pirollo K, Blattner W, and Chang E S: Germ-line transmission of a mutated p53 gene in a cancer-prone family with Li-Fraumeni syndrome. Nature, 348: 747-749, 1990.

79. Srivastava, S., Wang, S., Tong, Y. A., Hao, Z. M. and Chang, E. H.: Dominant negative effect of a germ-line mutant p53: a step fostering tumorigenesis. Cancer Res, 53:4452, 1993.

80. Gaddipati J P, Mcleod D G, Sesterhenn I A, Hussussian C J, Tong Y A, Seth P, Dracopoli N C, Moul J M, and Srivastava, S: Mutations of p16 gene are rare in prostate cancer. Prostate, 30:188-194, 1997.

81. Bonner R F, Emmert-Buck M, Cole K, Pohida T, Chuaqi R, Goldstein S, and Liotta L A: Laser capture microdissection: molecular analysis of tissue. Science, 278:1481-1483, 1997.

Bastian, B. C., Le Boit, P. E., Hamm, H., Brocker, E. B., and Pinkel, D. (1998). Chromosomal gains and losses in primary cutaneous melanomas detected by comparative genomic hybridization. Cancer Res. 58: 2170-2175.

Bentel, J. M., Tilley, W. D. (1996). Androgen receptors in prostate cancer. J. Endocrinology 151: 1-11.

Brothman, A. R., Peehl, D. M., Patel, A. M., and McNeal, J. E. (1990). Frequency and pattern of karyotypic abnormalities in human prostate cancer. Cancer Res. 50: 3795-3803.

Cuthill, S. (1999). Dominant genetic alterations in immortalization: Role for 20q gain. Genes Chromosomes Cancer 26: 304-311.

Gregory, C. W., Hamil, K. G., Kim, D., Hall, S. H., Pretlow, T. G., Mohler, J. L., and French, F. S. (1998). Androgen receptor expression in androgen-independent prostate cancer is associated with increased expression of androgen-regulated genes. Cancer Res. 58: 5718-5724.

Jarrard, D. F., Sarkar, S., Shi, T., Teager, T. R., Magrane, G., Kinoshita, H., Nassif, N., Meisner, L., Newton, M. A., and Waldman, F. M. (1999). p16/pRb pathway alterations are required for bypassing senescence in human prostate epithelial cells. Cancer Res. 59: 2957-2964.

Jenster G. (1999). The role of the androgen receptor in the development and progression of prostate cancer. Semin. Oncol. 26: 407-421.

Koivisto, P., Kolmer, M., Visakorpi, T., and Kallioniemi O. P. (1996). Androgen receptor gene and hormonal therapy failure of prostate cancer. Am. J. Pathol. 152: 1-9.

Korn, W. M., Yasutake, T., Kuo, W. L., Warren, R. S., Collins, C., Tomita, M., Gray, J., and Waldman, F. M. (1999). Chromosome arm 20q gains and other genomic alterations in colorectal cancer metastatic to liver, as analyzed by comparative genomic hybridization and fluorescence in situ hybridization. Genes Chromosomes Cancer. 25: 82-90.

Lin, B., Ferguson, C., White, J. T., Wang, S., Vessella, R., True, L. D., Hood, L., and Nelson, P. (1999). Prostate-localized and androgen-regulated expression of the membrane-bound serine protease TMPRSS2. Cancer Res. 59: 4180-4184.

Mahlamaki, E. H., Hoglund, M., Gorunova, L., Karhu, R., Dawiskiba, S., Andren-Sandberg, A., Kallioniemi, P. P., and Johansson, B. (1997). Comparative genomic hybridization reveals frequent gains of 20q, 8q, 11q, 12p, and 17q, and losses of 18q, 9p, and 15q in pancreatic cancer. Genes Chromosomes Cancer. 24: 383-391.

Moul J. W. (1998). Contemporary hormonal management of advanced prostate cancer. Oncology, 12: 499-505.

Nagabhushan, M., Miller, C. M., Pretlow, T. P., Ciacomia, J. M., Edgehouse, N. L., Schwarts, S., Kung, H., White, R. W., Gumerlock, P. H., Resnick, M. I., Amini, S. B., and Pretlow, T. G. (1996). CWR22: the first human prostate cancer xenograft with strongly androgen-dependent and relapsed strains both in vivo and in soft agar. Cancer Res. 56: 3042-3046.

Richter, J., Beffa, L., Wagner, U., Schraml, P., Gasser, T. C., Moch, H., Mihatsch, M. J., and Sauter, G. (1998). Patterns of chromosomal imbalances in advanced urinary bladder cancer detected by comparative genomic hybridization. Am. J. Pathol. 153: 1615-1621.

Stubbs, A. P., Abel, P. D., Golding, M., Bhangal, G., Wang, Q., Waxman, J., Stamp, G. W., and Lalani, E. N. (1999). Differentially expressed genes in hormone refractory prostate cancer: association with chromosomal regions involved with genetic aberrations. Am. J. Pathol. 154: 1335-1343.

Tanner, M. M., Tirkkonen, M., Kallioniemi, A., Isola, J., Kuukasjarvi, T., Collins, C., Kowbel, D., Guan, X. Y., Trent, J., and Gray, J. W. (1996). Independent amplification and frequent co-amplification of three nonsyntenic regions on the long arm of chromosome 20 in human breast cancer. Cancer Res. 56: 3441-3445.

Zhang, L., Zhou, W., Velculescu, V. E., Kern, S. E., Hruban, R. H., Hamilton, S. R., Vogelstein, B., And Kinzler, K. W. (1997). Gene expression profiles in normal and cancer cells. Science, 276: 1268-1272.

Douarin, B. L., You, J., Nielsen, A. L., Chambon, P., and Losson, R., Tif1α: a possible link between KRAB zinc finger proteins and nuclear receptors. J. Steroid Biochem. Molec. Biol., 65,43-50 (1998).

Xu, L., Su, Y., Labiche, R., Mcleod, D. G., Moul, J. W., and Srivastava, S., Quantitative Evaluation of the Expression Profile of the Androgen Regulated Genes (ARGs) in Prostate Cancer Cells. AACR annual meeting (1999).

Xu, L., Glass, C. K., and Rosenfeld, M. G., Coactivator and corepressor complexes in nuclear receptor function. Curr. Opin. Genet. Dev., 9, 140-147 (1999).

Miyajima, N., Kadowaki, Y., Fukushige, S., Shirnizu, S., Semba, K., Yamanashi, Y., Matsubara, K., Toyoshima, K., and Yamamoto, T., Identification of two novel members of erbA superfamily by molecular cloning: the gene products of the two are highly related to each other. Nucleic Acids Res., 16, 11057-11074 (1998).

Sreenath, T., Orosz, A., Fujita, K., and Bieberich, C. J., Androgen-independent expression of hoxb-13 in the mouse prostate. Prostate, 41, 203-207 (1999).

Patel, M. S., and Harris, R. A., Mammalian alpha-keto acid dehydrogenase complexes: gene regulation and genetic defects. FASEB J., 9, 1164-1172 (1995).

Ho, L., Wexler, I. D., Liu, T. C., Thekkumkara, T. J., and Patel, M. S., Characterization of cDNAs encoding human pyruvate dehydrogenase alpha subunit. Proc. Nat. Acad. Sci., 86, 5330-5334 (1989).

Ton, C., Hwang, D. M., Dempsey, A. A., and Liew, C. C., Identification and primary structure of five human NADH-ubiquinone oxidoreductase subunits. Biochem. Biophys. Res. Commun., 241, 589-594 (1997).

Blachly-Dyson, E., Baldini, A., Litt, M., Mccabe, E. R. B., and Forte, M., Human genes encoding the voltage-dependent anion channel (VDAC) of the outer mitochondrial membrane: mapping and identification of two new isoforms. Genomics, 20, 62-67 (1994).

Swinnen, J. V., Vercaeren, I., Esquenet, M., Heyns, W., and Verhoeven, G., Androgen regulation of the messenger RNA encoding diazepam-binding inhibitor/acyl-CoA-binding protein in the rat. Mol. Cell Endocrinol., 118, 65-70 (1996).

Knudsen, J., Mandrup, S., Rasmussen, J. T., Andreasen, P. H., Poulsen, F., and Kristiansen, K., The function of acyl-CoA-binding protein (ACBP)/diazepam binding inhibitor (DBI). Mol. Cell Biochem., 123, 129-138 (1993).

Miranda-Vizuete, A., Gustafsson, J. A., and Spyrou, G., Molecular cloning and expression of a cDNA encoding a human thioredoxin-like protein. Biochem. Biophys. Res. Commun., 243, 284-288 (1998).

Cartwright, R., Tambini, C. E., Simpson, P. J., and Thacker, J., The XRCC2 DNA repair gene from human and mouse encodes a novel member of the recA/RAD51 family. Nucleic Acids Res., 26, 3084-3089 (1998).

Umbricht, C. B., Erdile, L. F., Jabs, E. W., and Kelly, T. J., Cloning, overexpression, and genomic mapping of the 14-kDa subunit of human replication protein A. J. Biol. Chem., 268, 6131-6138 (1993).

Gu, Z., Flemington, C., Chittenden, T., and Zambetti, G. P., ei24, a p53 response gene involved in growth suppression and apoptosis. Mol. Cell. Biol., 20, 233-241 (2000).

Srivastava, M., and Pollard, H. B., Molecular dissection of nucleolin's role in growth and cell proliferation: new insights. FASEB J., 13, 1911-1922 (1999).

Page-Mccaw, P. S., Amonlirdviman, K., and Sharp, P. A., Puf60: A U2AF65 homolog that binds the pyrimidine tract. RNA, 5, 1548-1560 (1999).

Qian, Z., and Wilusz, J., Grsf-1: a poly (A)+mRNA binding protein which interacts with a conserved G-rich element. Nucleic Acids Res., 22, 2334-2343 (1994).

Craig, A. W., Haghighat, A., Yu, A. T., and Sonenberg, N., Interaction of polyadenylate-binding protein with the eIF4G homologue PAIP enhances translation. Nature, 392, 520-523 (1998).

Hunt, S. L., Hsuan, J. J., Totty, N., and Jackson, R. J., unr, a cellular cytoplasmic RNA-binding protein with five cold-shock domains, is required for internal initiation of translation of human rhinovirus RNA. Genes Dev., 13, 437-448 (1999).

Velculescu, V. E., Zhang, L., Zhou, W., Vogelstein, J., Basrai, M. A., Bassett, D. E. Jr., Hieter, P., Vogelstein, B., and Kinzler, K. W., Characterization of the yeast transcriptome. Cell, 88, 243-251 (1997).

Polyak, K., Xia, Y., Zweier, J. L., Kinzler, K. W., and Vogelstein, B., A model for p53-induced apoptosis. Nature, 389, 300-305 (1997).

Hermeking, H., Lengauer, C., Polyak, K., He, T. C., Zhang, L., Thiagalingam, S., Kinzler, K. W., and Vogelstein, B. 14-3-3-σ is a p53-regulated inhibitor of G2/M progression. Molecular Cell, 1, 3-11 (1997).

Korinek, V., Barker, N., Morin, P. J., Wichen, D., Weger, R., Kinzler, K. W., Vogelstein, B., and Clevers, H., Constitutive transcriptional activation by a β-Catenin-Tcf complex in $APC^{-/-}$ colon carcinoma. Science, 275, 1784-1787 (1997).

Zhang, L., Zhou, W., Velculescu, V. E., Kern, S. E., Hruban, R. H., Hamilton, S. R., Vogelstein, B., and Kinzler, K. W., Gene expression profiles in normal and cancer cells. Science, 276, 1268-1272 (1997).

Hibi, K., Liu, Q., Beaudry, G. A., Madden, S I., Westra, W. H., Wehage, S. L., Yang, S. C., Heitmiller, R. F., Bertelsen, A. H., Sidransky, D., and Jen, J. Serial analysis of gene expression in non-small cell lung cancer. Cancer Res., 58, 5690-5694 (1998).

Nacht, M., Ferguson, A. T., Zhang, W., Petroziello, J. M., Cook, B. P., Gao, Y. H., Maguire, S., Riley, D., Coppola, G., Landes, G. M., Madden, S. L., and Sukumar, S., Combining serial analysis of gene expression and array technologies to identify genes differentially expressed in breast cancer. Cancer Res., 59, 5464-5470 (1999).

Waard, V., Berg, B. M. M., Veken, J., Schultz-Heienbrok, R., Pannekoek, H., and Zonneveld, A., Serial analysis of gene expression to asssess the endothelial cell response to an atherogenic stimulus. Gene, 226, 1-8 (1999).

Berg, A., Visser, L., and Poppema, S., High expression of the CC chemokine TARC in reed-stemberg cells. A possible explanation for the characteristic T-cell infiltrate in hodgkin" lymphoma. Am. J. Pathol., 154, 1685-1691 (1999).

Iyer, V. R., Eisen, M. B., Ross, D. T., Schuler, G., Moore, T., Lee, J. C. F., Trent, J. M., Staudt, L. M., Hudson, J. Jr., Boguski, M. S., Lashkari, D., Shalon, D., Botstein, D., and Brown, P. O., The trancriptional program in the response of human fibroblasts to serum. Science, 283, 83-87 (1999).

Charpentier, A. H., Bednarek, A. K., Daniel, R. L., Hawkins, K. A., Laflin, K. J., Gaddis, S., Macleod, M. C., and Aldaz, C. M., Effects of estrogen on global gene expression: identification of novel targets of estrogen action. Cancer Res., 60, 5977-5983 (2000).

Ripple, M. O., Henry, W. F., Rago, R. P., and Wilding, G., Prooxidant-antioxidant shift induced by androgen treatment of human prostate carcinoma cells. J. Nat. Cancer Inst., 89, 4048 (1997).

We claim:

1. A method of diagnosing prostate cancer, comprising determining the expression of an androgen-regulated gene in a biological sample comprising prostate cells, wherein the androgen-regulated gene is PMEPA1, wherein expression of the PMEPA1 gene is determined by measuring the level of expression of a PMEPA1 nucleotide sequence comprising SEQ ID NO:2 in the biological sample, and wherein reduced expression of the PMEPA1 gene in the biological sample as compared to a control sample comprising noncancerous prostate cells correlates with an increased probability for the presence of prostate cancer.

2. The method of claim 1, wherein expression of the PMEPA1 gene in the biological sample is reduced at least 1.5 fold as compared to the control sample.

3. The method of claim 1, wherein the level of expression of the PMEPA1 nucleotide sequence is determined after amplifying the PMEPA1 nucleotide sequence in the biological sample.

4. The method of claim 3, wherein the PMEPA1 nucleotide sequence is amplified using a first PCR primer having the nucleotide sequence of SEQ ID NO:77 and a second PCR primer having the nucleotide sequence of SEQ ID NO:78.

5. The method of claim 3, wherein the expression of the PMEPA1 nucleotide sequence is detected using a probe having the nucleotide sequence of SEQ ID NO:79.

6. A method of prognosing the pathologic stage of prostate cancer in a patient, comprising determining the expression of an androgen regulated gene in a biological sample comprising prostate cells, wherein the androgen-regulated gene is PMEPA1, wherein expression of the PMEPA1 gene is determined by measuring the level of expression of a PMEPA1 nucleotide sequence comprising SEQ ID NO:2 in the biological sample, and wherein reduced expression of the PMEPA1 gene in the biological sample as compared to a control sample comprising noncancerous prostate cells correlates with an increased probability for advanced prostate cancer, wherein the advanced prostate cancer is characterized by at least pathological T3 disease.

7. The method of claim 6, wherein the advanced prostate cancer comprises non-organ confined tumors, wherein the tumors are not confined to the prostate gland.

8. The method of claim 7, wherein expression of the PMEPA1 gene in the biological sample is reduced at least 1.5 fold as compared to the control sample.

9. The method of claim 7, wherein the level of expression of the PMEPA1 nucleotide sequence is determined after amplifying the PMEPA1 nucleotide sequence in the biological sample.

10. The method of claim 9, wherein the PMEPA1 nucleotide sequence is amplified using a first PCR primer having the nucleotide sequence of SEQ ID NO:77 and a second PCR primer having the nucleotide sequence of SEQ ID NO:78.

11. The method of claim 9, wherein the expression of the PMEPA1 nucleotide sequence is detected using a probe having the nucleotide sequence of SEQ ID NO:79.

* * * * *